United States Patent
Engeland et al.

(10) Patent No.: US 10,933,106 B2
(45) Date of Patent: Mar. 2, 2021

(54) RNA VIRUSES FOR IMMUNOVIROTHERAPY

(71) Applicants: DEUTSCHES KREBSFORSCHUNG-SZENTRUM, Heidelberg (DE); RUPRECHT-KARLS-UNIVERSITAT HEIDELBERG, Heidelberg (DE)

(72) Inventors: Christine Engeland, Heidelberg (DE); Guy Ungerechts, Heidelberg (DE); Sascha Bossow, Ottowa (CA)

(73) Assignee: DEUTSCHES KREBSFORSCHUNGSZENTRUM, Heidelberg (DE)

( * ) Notice: Subject to any disclaimer, the term of this patent is extended or adjusted under 35 U.S.C. 154(b) by 201 days.

(21) Appl. No.: 15/121,751

(22) PCT Filed: Feb. 24, 2015

(86) PCT No.: PCT/EP2015/053801
§ 371 (c)(1),
(2) Date: Aug. 25, 2016

(87) PCT Pub. No.: WO2015/128313
PCT Pub. Date: Sep. 3, 2015

(65) Prior Publication Data
US 2017/0065650 A1    Mar. 9, 2017

Related U.S. Application Data

(60) Provisional application No. 61/944,353, filed on Feb. 25, 2014.

(51) Int. Cl.
| | | |
|---|---|---|
| *A61K 35/768* | (2015.01) | |
| *C12N 7/00* | (2006.01) | |
| *C12N 15/86* | (2006.01) | |
| *A61K 39/395* | (2006.01) | |

(52) U.S. Cl.
CPC ...... *A61K 35/768* (2013.01); *A61K 39/39558* (2013.01); *C12N 7/00* (2013.01); *C12N 15/86* (2013.01); *C12N 2760/18432* (2013.01); *C12N 2760/18433* (2013.01); *C12N 2760/18441* (2013.01); *C12N 2760/18471* (2013.01)

(58) Field of Classification Search
CPC ............ A61K 35/768; A61K 39/39558; C12N 15/86; C12N 7/00; C12N 2760/18432; C12N 2760/18471; C12N 2760/18441; C12N 2760/18433
USPC ...................... 424/199.1, 212.1, 135.1, 154.1
See application file for complete search history.

(56) References Cited

U.S. PATENT DOCUMENTS

2015/0250837 A1* 9/2015 Nolin ................. C07K 16/2818
424/281.1

OTHER PUBLICATIONS

Grossardt et al. (Jun., 2013) Molecular Therapy, vol. 21 (Suppl. 1), p. S156.*
Grote et al. (2003) Cancer Research, vol. 63, 6463-6468.*
Combredet et al. (2003) J. Virol., vol. 77(21), 11546-11554.*
Pol et al. (2013) Molecular Therapy, vol. 21 (10), pp. 1814-1818.*
Dias et al. (2012) Gene Therapy, vol. 19, 988-998, published online Nov. 10, 2011.*
European Patent Office, Written Opinion of the International Searching Authority, dated Jun. 25, 2015.

* cited by examiner

Primary Examiner — Anne Marie S Wehbe
(74) Attorney, Agent, or Firm — Ice Miller LLP

(57) ABSTRACT

The present invention relates to a recombinant virus of the family Paramyxoviridae, comprising at least one expressible polynucleotide encoding a secreted activator of the immune response, to a polynucleotide encoding the same, and to a kit comprising the same. Moreover, the present invention relates to a method for treating cancer in a subject afflicted with cancer, comprising contacting said subject with a recombinant virus of the family Paramyxoviridae of the invention, and thereby, treating cancer in a subject afflicted with cancer.

Figure 1:
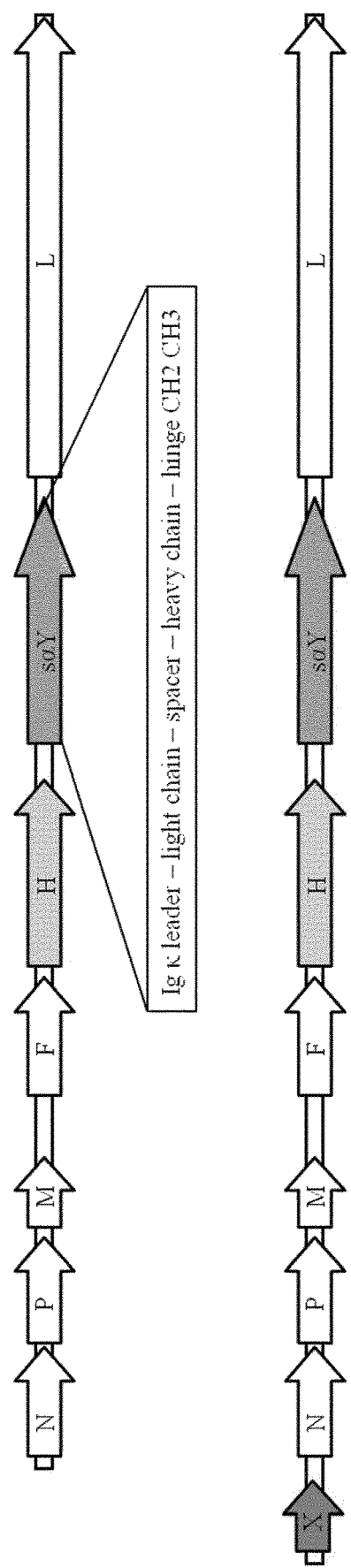

18 Claims, 8 Drawing Sheets
Specification includes a Sequence Listing.

Fig. 4

Fig. 5

RNA VIRUSES FOR IMMUNOVIROTHERAPY

CROSS-REFERENCE TO RELATED APPLICATIONS

The present application is a U.S. national stage of, and claims the priority benefit of, International Patent Application Serial No. PCT/EP2015/053801, filed Feb. 24, 2015 and U.S. Patent Application Ser. No. 61/994,353, filed Feb. 25, 2014, the text and drawings of which are hereby incorporated by reference in their entireties.

The present invention relates to a recombinant virus of the family Paramyxoviridae, comprising at least one expressible polynucleotide encoding a secreted activator of the immune response, to a polynucleotide encoding the same, and to a kit comprising the same. Moreover, the present invention relates to a method for treating cancer in a subject afflicted with cancer, comprising contacting said subject with a recombinant virus of the family Paramyxoviridae of the invention, and thereby, treating cancer in a subject afflicted with cancer.

Oncolytic viruses (OV) which replicate selectively in tumor cells are an emerging modality of cancer treatment. Aside from direct cytopathic effects and lysis of tumor cells, interactions of OV with the immune system can trigger systemic anti-tumor immunity. OV have been modified to express immunomodulatory transgenes to further enhance these effects (Melcher et al., Mol Ther. 2011, 19: 1008-1016). The vaccinia virus JX-594 and herpesvirus talimogene laherpavec (TVEC), both harboring GM-CSF, have shown promising results in clinical phase II and III trials (Heo et al., Nat Med. 2013, 19: 329-336 and Andtbacka et al. J Clin Oncol. 2013, 31, suppl; abstr LBA9008).

RNA viruses, in particular members of the family Paramyxoviridae like, e.g. measles virus, have also shown potential use in oncolysis. Viruses of the family Paramyxoviridae are negative-sense single-stranded RNA viruses and include human pathogens like, e.g. human parainfluenza viruses, mumps virus, human respiratory syncytial virus, and measles virus. From wildtype measles virus, several non-pathogenic strains, including a vaccination strain, have been derived, which have been shown to be still oncolytic. The measles virus vaccine strain has been developed as a vector platform to target multiple tumor entities and several clinical trials are ongoing (Russell et al., Nat Biotechnol. 2012, 30: 658-670). Recently, the capacity of oncolytic MV encoding GM-CSF to support the induction of a specific anti-tumor immune response in terms of a tumor vaccination effect was demonstrated (Grossardt et al. Hum Gene Ther. 2013, 24: 644-654.).

In general, immune response via T cell activation involves the integration of numerous signals at so-called immune checkpoints. Immune checkpoint inhibition is a novel paradigm in cancer immunotherapy. CTLA-4 (Cytotoxic T-Lymphocyte Antigen 4), also known as CD152 (Cluster of differentiation 152) and PD-L1 (Programmed cell death 1 ligand 1, also known as CD274 (cluster of differentiation 274) or B7 homolog 1 (B7-H1)) are key molecules in this process (Chen and Flies, Nat Rev Immunol. 2013, 13: 227-242). CTLA-4 is a co-inhibitory surface molecule on T cells which belongs to the CD28 receptor subfamily. It is induced upon initial recognition of a T cell's cognate antigen and constitutively expressed on regulatory T cells (Tregs) (Rudd et al., Immunol Rev. 2009, 229: 12-26; Walker and Sansom, Nat Rev Immunol. 2011, 11: 852-863). The physiological role of CTLA-4 is regulation of self-tolerance, which is illustrated by the lethal systemic immune hyperactivation phenotype of CTLA-4 knockout mice (Tivol et al., Immunity. 1995, 3: 541-547). As a central mediator of T cell inhibition, CTLA-4 has been implicated in immune tolerance of tumors. CTLA-4 blockade has been shown to enhance antitumor immunity in multiple preclinical and clinical studies (Egen et al., Nature Immunol. 2002, 3: 611-618; Ott et al., Clin Cancer Res. 2013, 19: 5300-5309). Similarly, PD-L1 is a surface glycoprotein which acts as a ligand for the T cell inhibitory factor PD-1. PD-L1 is broadly expressed on immune cells and healthy tissues and is induced by interferon-$\gamma$ (Okazaki and Honjo, Trends Immunol. 2006, 27: 195-201). It mediates fetomaternal tolerance (Guleria et al., J Exp Med. 2005, 202: 231-237) and allograft tolerance after organ transplantation (Tanaka et al., J Immunol. 2007, 179: 5204-5210). In models of autoimmune diseases such as diabetes and encephalomyelitis, PD-L1 knockout leads to an aggravated phenotype (Keir et al., J Exp Med. 2006, 203: 883-895; Latchman et al., Proc Natl Acad Sci USA. 2004, 101: 10691-10696). PD-1/PD-L1 signaling is initiated after chronic antigen exposure, leading to T cell exhaustion (Barber et al., Nature. 2006, 439: 682-687). PD-L1 is overexpressed in various tumor entities and inhibits T cell-mediated anti-tumor immunity (Iwai et al., Proc Natl Acad Sci USA. 2002, 99: 12293-12297).

By antagonizing CTLA-4, PD-1 and PD-L1, anti-tumor immune effectors can be reinvigorated with unprecedented success in metastatic melanoma and other advanced-stage tumors (Hodi et al., N Engl J Med. 2010, 363: 711-723; Topalian et al. N Engl J Med. 2012, 366: 2443-2454; Brahmer et al. N Engl J Med. 2012, 366: 2455-2465). However, immune-related adverse events are frequent and tend to be severe in systemic immunotherapy (Quezada and Peggs, Br J Cancer. 2013, 108: 1560-1565.).

There is, thus, a need in the art for improved cancer therapies, in particular for improved oncolytic viruses.

Accordingly, the present invention relates to a recombinant virus of the family Paramyxoviridae, comprising an expressible polynucleotide encoding a secreted activator of the immune response.

The terms "virus" and "virus of the family Paramyxoviridae" are known to the skilled person. Preferably, the virus of the family Paramyxoviridae is a member of the genus Morbillivirus. More preferably, the virus of the family Paramyxoviridae is a measles virus (MV), still more preferably a MV strain Edmonston A or B, or, most preferably, vaccine strain Schwarz (Edmonston A).

The term "recombinant virus", as used herein, relates to a virus comprising a genome modified by biotechnological means as compared to known, naturally occurring, virus genomes. Preferably, the recombinant virus is a virus comprising a genome modified as compared naturally occurring virus genomes. Preferred biotechnological means for modifying a viral genome are known to the skilled person and include any of the methods of molecular cloning, in particular recombinant DNA techniques including, without limitation, cleavage of DNA by restriction enzymes, ligation of DNA, polymerase chain reaction (PCR), cloning of viral genomes, and the like. It is understood by the skilled person that viruses of the family Paramyxoviridae have a single-stranded (−)-RNA as a genome. Accordingly, the genome of the recombinant virus of the present invention, preferably, is obtained by cloning an expression vector as described herein below comprising an expressible nucleotide sequence encoding said recombinant virus genome, followed by expressing said expressible nucleotide sequence encoding said recombinant virus in a permissive host cell. Alternatively, the recombinant virus genome may also be expressed in non-permissive host cells, e.g., preferably, from rodents or other higher eukaryotes.

As used herein, the term "activator of the immune response" relates to a compound which, when contacted with immune cells, causes at least one type of immune cell to be more active as compared to an immune cell of the same type not contacted with said compound. Preferably, said immune cell is a cell mediating a response increasing a subject's resistance to an antigen, i.e. preferably, said immune cell is not a tolerance-mediating immune cell. Measures of immune cell activity are known to the skilled person and include, preferably, expression of activation markers, production of antibodies, excretion of cytokines, and release of cytotoxins, e.g. perforin, granzymes, and/or granolysin. Preferably, the immune cell activated by the activator of the immune response is a T-cell, more preferably a helper T-cell or a cytotoxic T-cell. Most preferably, the immune cell activated by the activator of the immune response is a helper T-cell or a Treg cell expressing CTLA-4 or a cytotoxic T-cell expressing PD-1.

Preferably, the activator of the immune response is an antagonist of a signaling pathway causing at least one type of immune cell to become inhibited. Accordingly, preferably, the activator of the immune response is a ligand for an immune checkpoint blockade protein. More preferably, the activator of the immune response is a ligand for an immune checkpoint blockade protein. Still more preferably, the activator of the immune response is an inhibitor of BTLA receptor signaling, TIM3 receptor signaling, or, more preferably of CTLA-4 receptor signaling or of PD-1 receptor signaling. It is understood by the skilled person that signaling through a receptor signaling pathway can be inhibited by either preventing the receptor from being activated, or by preventing the signal generated by the activated receptor from being further transmitted. Accordingly, preferably, the activator of the immune response is a CTLA-4 antagonist, a PD-1 antagonist, a CD80 antagonist, a CD86 antagonist, or a PD-L1 antagonist, the term "antagonist" relating to a compound binding to the molecule the effect of which is antagonized and through said binding preventing said molecule from interacting with its native binding partner in a productive, i.e. signaling-inducing, way. Preferred assays for said activity are described herein in the accompanying Examples.

Preferably, the activator of the immune response is an antagonist as described above selected from the list of molecule types consisting of a peptide aptamer, an anticalin, a Designed Ankyrin Repeat Protein (DARPin), an inhibitory peptide, and, preferably, an antibody.

In the context of this invention, a "peptide aptamer" is a peptide specifically binding its interaction partner and having the activity of activating the immune response as specified herein above, preferably, the activity of being an antagonist of CTLA-4, PD-1, CD80, CD86, and/or PD-L1 as specified herein above. Peptide aptamers, preferably, are peptides comprising 8-80 amino acids, more preferably 10-50 amino acids, and most preferably 15-30 amino acids. They can e.g. be isolated from randomized peptide expression libraries in a suitable host system like baker's yeast (see, for example, Klevenz et al., Cell Mol Life Sci. 2002, 59: 1993-1998). A peptide aptamer, preferably, is a free peptide; it is, however, also contemplated by the present invention that a peptide aptamer is fused to a polypeptide serving as "scaffold", meaning that the covalent linking to said polypeptide serves to fix the three-dimensional structure of said peptide aptamer to one specific conformation. More preferably, the peptide aptamer is fused to a transport signal, in particular a peptide export signal.

As used herein, the term "anticalin" relates to an artificial polypeptide derived from a lipocalin specifically binding its interaction partner. Similarly, a "Designed Ankyrin Repeat Protein" or "DARPin", as used herein, is an artificial polypeptide comprising several ankyrin repeat motifs and specifically binding its interaction partner. The anticalins and the DARPins of the present invention have the activity of activating the immune response as specified herein above, preferably, the activity of being an antagonist of CTLA-4, PD-1, CD80, CD86, and/or PD-L1 as specified herein above.

As used herein, the term "inhibitory peptide" relates to any chemical molecule comprising at least one peptide having the activity of activating the immune response as specified herein above, preferably, the activity of being an antagonist of CTLA-4, PD-1, CD80, CD86, and/or PD-L1 as specified herein above. Preferably, the inhibitory peptide comprises a peptide having an amino acid sequence corresponding to an amino acid sequence of at least five, at least six, at least seven, at least eight, at least nine, at least ten, at least eleven, at least twelve, at least 13, at least 14, or at least 15 consecutive amino acids comprised in a CTLA-4, a PD-1, a CD80, a CD86, and/or a PD-L1 polypeptide. Preferably, the inhibitory peptide comprises a peptide having an amino acid sequence corresponding to an amino acid sequence of 5 to 200, more preferably 6 to 100, even more preferably 7 to 50, or, most preferably, 8 to 30 consecutive amino acids comprised in a CTLA-4, a PD-1, a CD80, a CD86, and/or a PD-L1 polypeptide. Moreover, also encompassed are variants of the aforementioned inhibitory peptides. Such variants have at least the same essential biological activity as the specific inhibitory peptides. Moreover, it is to be understood that a variant as referred to in accordance with the present invention shall have an amino acid sequence which differs due to at least one amino acid substitution, deletion and/or addition, wherein the amino acid sequence of the variant is still, preferably, at least 50%, 60%, 70%, 80%, 85%, 90%, 92%, 95%, 97%, 98%, or 99% identical with the amino sequence of the specific inhibitory peptides. The degree of identity between two amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining, preferably over the whole length of the peptide, the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman (1981), by the homology alignment algorithm of Needleman and Wunsch (1970), by the search for similarity method of Pearson and Lipman (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Variants referred to above may be allelic variants or any other species specific homologs, paralogs, or orthologs. Moreover, the variants referred to herein include fragments of the specific inhibitory peptides or the aforementioned types of variants as long as these fragments and/or variants have the essential biological activity as referred to above. Such fragments may be or be derived from, e.g., degradation products or splice variants of the inhibitory peptides. Further included are variants which differ due to posttranslational modifications such as phosphorylation, glycosylation, ubiquitinylation, sumoylation or myristylation.

Preferably, the inhibitory peptide comprises further amino acids which may serve e.g. as immunogens, as a tag for purification or detection or as a linker. In a preferred embodiment of the inhibitory peptide of the present invention, said inhibitory peptide further comprises an immunogenic peptide. The term "immunogenic peptide" refers to a stretch of amino acids which is added to or introduced into the inhibitory peptide of the invention. Preferably, the immunogenic peptide shall be added C- or N-terminally to the inhibitory peptide of the present invention. In another preferred embodiment of the inhibitory peptide of the present invention, said inhibitory peptide further comprises a detectable tag. The term "detectable tag" refers to a stretch of amino acids which are added to or introduced into the inhibitory peptide of the invention. Preferably, the tag shall be added C- or N-terminally to the inhibitory peptide of the present invention. The said stretch of amino acids shall allow for detection of the inhibitory peptide by an antibody which specifically recognizes the tag or it shall allow for forming a functional conformation, such as a chelator or it shall allow for visualization by fluorescent tags. Preferred tags are the Myc-tag, FLAG-tag, 6-His-tag, HA-tag, GST-tag or GFP-tag. These tags are all well known in the art. More preferably, the inhibitory peptide comprises further amino acids which may serve as mediators of cell entry, i.e., preferably, the inhibitory peptide further comprises at least one cell-penetrating peptide (CPP). CPPs are well known in the art and include, e.g., Penetratins, HIV-tat-related peptides, Transportans, and the like, see, e.g. Nasrollahi et al., Chem Biol Drug Des. 2012, 80: 639-646.

As used herein, the term "antibody" relates to a soluble immunoglobulin from any of the classes IgA, IgD, IgE, IgG, or IgM, having the activity of activating the immune response as specified herein above, preferably, the activity of being an antagonist of CTLA-4, PD-1, CD80, CD86, and/or PD-L1 as specified herein above. Antibodies against said polypeptides can be prepared by well known methods using a purified polypeptide or a suitable fragment derived therefrom as an antigen. A fragment which is suitable as an antigen may be identified by antigenicity determining algorithms well known in the art. Such fragments may be obtained either from one of the polypeptides of the invention by proteolytic digestion, may be a synthetic peptide, or may be recombinantly expressed. Preferably, the peptide used as an antigen is located at or close to the interaction site in one of the C80/CTLA-4, CD86/CTLA-4, and PD-L1/PD-1 receptor complexes. Suitability of an antibody thus generated as an activator of the immune response can be tested by the assay as described herein in the Examples. Preferably, the antibody of the present invention is a monoclonal antibody, a human or humanized antibody or primatized, chimerized or fragment thereof. More preferably, the antibody is a single chain antibody or an antibody fragment, such as Fab, scFab. Also comprised as antibodies of the present invention are a bispecific antibody, a synthetic antibody, or a chemically modified derivative of any of these. Preferably, the antibody of the present invention shall specifically bind (i.e. does not cross react with other polypeptides or peptides) to a polypeptide as specified above. Specific binding can be tested by various well known techniques. Antibodies or fragments thereof can be obtained by using methods which are described, e.g., in Harlow and Lane "Antibodies, A Laboratory Manual", CSH Press, Cold Spring Harbor, 1988. Monoclonal antibodies can be prepared by the techniques originally described in Köhler and Milstein, Nature. 1975. 256: 495; and Galfré, Meth. Enzymol. 1981, 73: 3, which comprise the fusion of mouse myeloma cells to spleen cells derived from immunized mammals.

Preferably, the activator of the immune response as described herein above is a polypeptide expressible from a single transcription unit. Accordingly, preferably, the activator of the immune response is a polypeptide or a fusion polypeptide. More preferably, the activator of the immune response is a single chain antibody or a single chain Fab polypeptide. Still more preferably, the activator of the immune response is an antagonistic anti-CTLA-4 single chain antibody, most preferably comprising the amino acid sequence of SEQ ID NO:1, preferably encoded by a polynucleotide comprising the nucleic acid sequence of SEQ ID NO:2; or an antagonistic anti-PD-L1 antibody, most preferably comprising the amino acid sequence of SEQ ID NO:3, preferably encoded by a polynucleotide comprising the nucleic acid sequence of SEQ ID NO:4.

The term "secreted", as used herein, relates to a compound being transferred from the interior of a host cell to the exterior of said host cell by a mechanism intrinsic to said host cell. Preferably, in case the activator of the immune response is a peptide or polypeptide, said secretion is mediated by a, preferably eukaryotic, signal peptide mediating import of said peptide or polypeptide into the lumen of the endoplasmic reticulum and, more preferably, by the absence of retention signals. Signal peptides causing secretion of peptides or polypeptides are known in the art. Preferably, the signal peptide is or comprises an Ig leader sequence. More preferably, the signal peptide is or comprises a human Ig leader sequence. Still more preferably, the signal peptide is or comprises a matching leader sequence, i.e. a leader sequence selected from the same Ig kappa subgroup as the variable light chain of the antibody, preferably, of the single-chain antibody. Most preferably, the signal peptide is or comprises an amino acid sequence of SEQ ID NO: 5.

The term "expressible polynucleotide", as used herein, relates to a polynucleotide operatively linked to at least one expression control sequence causing transcription of the nucleic acid sequence comprised in said polynucleotide to occur, preferably in eukaryotic cells or isolated fractions thereof, preferably into a translatable mRNA or into a viral genome. Regulatory elements ensuring expression in eukaryotic cells, preferably mammalian cells, are well known in the art. They, preferably, comprise regulatory sequences ensuring initiation of transcription and, optionally, poly-A signals ensuring termination of transcription and stabilization of the transcript. Additional regulatory elements may include transcriptional as well as translational enhancers. Preferably, the aforesaid at least one expression control sequence is an expression control sequence of a (−)strand RNA virus, more preferably of a Paramyxovirus as described herein above, most preferably of an MV. Thus, preferably, the at least one expression control sequence comprises a (−)strand RNA viral regulatory sequence ensuring initiation of transcription (consensus "gene start signal", preferably consensus MV "gene start signal") and termination signals (consensus "gene stop signal", preferably, consensus MV "gene stop signal") ensuring termination of transcription and stabilization of the transcript. It is known in the art that production of viral particles in permissive host cells can be initiated by transfecting into said permissive host cells one or more expressible DNA constructs encoding (i) a recombinant viral genome, (ii) the viral L gene, (iii) the viral P gene and (iv) the viral N gene. It is also understood by the skilled person that, once a viral genome and the aforesaid viral genes were expressed in said host cell, replication and assembly of viral particles occurs in the cytoplasm of the host cell and is, therefore, solely dependent on viral regulatory signals. Preferably, the expressible polynucleotide comprises the nucleic acid sequence of SEQ ID NO:2, encoding a polypeptide comprising SEQ ID NO:1, or comprises the nucleic acid sequence of SEQ ID NO:4, encoding a polypeptide comprising SEQ ID NO:3.

The term "polynucleotide", as used in accordance with the present invention, encompasses variants of the aforementioned specific polynucleotides. Moreover, it is to be understood that the polypeptides having amino acid sequences of the polypeptides of the present invention may also be encoded due to the degenerated genetic code by more than one species of polynucleotide. The polynucleotide variants, preferably, comprise a nucleic acid sequence characterized in that the sequence can be derived from the aforementioned specific nucleic acid sequences by at least one nucleotide substitution, addition and/or deletion whereby the variant nucleic acid sequence shall still encode a peptide or polypeptide having the activity as specified herein. Variants also encompass polynucleotides comprising a nucleic acid sequence which is capable of hybridizing to the aforementioned specific nucleic acid sequences, preferably, under stringent hybridization conditions. These stringent conditions are known to the skilled worker and can be found in Current Protocols in Molecular Biology, John Wiley & Sons, N. Y. (1989), 6.3.1-6.3.6. A preferred example for stringent hybridization conditions are hybridization conditions in 6× sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA:DNA hybrids are preferably for example 0.1×SSC and 20° C. to 45° C., preferably between 30° C. and 45° C. The hybridization conditions for DNA:RNA hybrids are preferably, for example, 0.1×SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above. Alternatively, polynucleotide variants are obtainable by PCR-based techniques such as mixed oligonucleotide primer-based amplification of DNA, i.e. using degenerated primers against conserved domains of the polypeptides or peptides of the present invention. Conserved domains of the polypeptides or peptides of the present invention may be identified by a sequence comparison of the nucleic acid sequence of the polynucleotide or of the amino acid sequence of the polypeptides as specified above. Suitable PCR conditions are well known in the art. As a template, DNA or cDNA from appropriate cells may be used. Further, variants include polynucleotides comprising nucleic acid sequences which are at least 70%, at least 75%, at least 80%, at least 85%, at least 90%, at least 95%, at least 98% or at least 99% identical to the nucleic acid sequences detailed above. The percent identity values are, preferably, calculated over the entire amino acid or nucleic acid sequence region. A series of programs based on a variety of algorithms is available to the skilled worker for comparing different sequences as described herein above. A polynucleotide comprising a fragment of any of the aforementioned nucleic acid sequences and encoding a polypeptide or peptide comprising or consisting of the domains conferring the biological activities of a polypeptide of the present invention is also encompassed as a polynucleotide of the present invention. The polynucleotide of the present invention shall be provided, preferably, either as an isolated polynucleotide (i.e. isolated from its natural context) or in genetically modified form. The polynucleotide, preferably, is DNA including cDNA, or RNA. The term encompasses single as well as double stranded polynucleotides. Also included by the term polynucleotide, preferably, are chemically modified polynucleotides including naturally occurring modified polynucleotides such as glycosylated or methylated polynucleotides or artificially modified ones such as biotinylated polynucleotides. The polynucleotides of the present invention either essentially consist of the aforementioned nucleic acid sequences or comprise the aforementioned nucleic acid sequences. Thus, they may contain further nucleic acid sequences as well.

The term "polynucleotide encoding a recombinant virus", as used herein, relates to a polynucleotide comprising a nucleic acid sequence or nucleic acid sequences required for generating a virus particle or a virus-like particle in a host cell. It is understood by the skilled person that a virus is constituted by a polynucleotide genome and at least one kind of capsid polypeptide. Accordingly, the polynucleotide encoding a recombinant virus of the present invention, preferably, comprises a recombinant virus genome. As will be understood by the skilled person, in case the polynucleotide encoding a recombinant virus is comprised in a virus according to the present invention, the polynucleotide is (−)strand RNA. It is also understood by the skilled person that in case the polynucleotide is DNA comprised in a host cell, at least an RNA-dependent RNA polymerase activity will additionally be required to produce viral particles from said DNA polynucleotide, as described herein above and below in the Examples. Preferably, the polynucleotide encoding a recombinant virus comprises or consists of the nucleic acid sequence of SEQ ID NO: 6, 7, 8, or 9. As annotated herein, the sequence of the DNA copy of negative-strand (−)RNA viruses is annotated in the usual 5'→3'-orientation; this corresponds to the viral sequence in antigenomic (+)RNA orientation with respect to the natural 3'→5'-orientation of negative-strand (−)RNA viruses.

The term "cytokine" is known to the skilled person and relates to any one of a group of peptides released by cells and affecting the state or behaviour of other or the same cells.

Preferably, the cytokine is a chemokine, an interferon, an interleukin, a lymphokine, or a tumor necrosis factor. More preferably, the cytokine is GM-CSF (Genbank Acc NO: AAA52121.1 GI:181146, preferably encoded by Genbank Acc NO: M10663.1 GI:181145) or Interleukin-12 (p35 subunit, Genbank Acc NO: AAD16432.1 GI:4323579; p40 subunit, Genbank Acc NO: AAG32620.1 GI:11192035.)

As used herein, the term "host cell" relates to a vertebrate cell. Preferably, the cell is a mammalian cell, more preferably, a mouse, rat, cat, dog, hamster, guinea pig, sheep, goat, pig, cattle, or horse cell. Still more preferably, the host cell is a primate cell. Most preferably, the host cell is a human cell. Preferably, the host cell is a tumor cell, more preferably a cancer cell.

Advantageously, it was found in the work underlying the present invention that measles virus can be engineered to express polypeptides destined for secretion and that these polypeptides are efficiently secreted during viral replication in the cell. Moreover, it was found that by administering measles virus expressing a secreted molecule preventing shutdown signaling to T-cells, the immune response to cancer cells can be improved and, in particular, tolerance induction by the tumor microenvironment can be alleviated. In contrast to methods of the prior art, no systemic treatment with the activator of the immune system is required.

The definitions made above apply mutatis mutandis to the following. Additional definitions and explanations made further below also apply for all embodiments described in this specification mutatis mutandis.

The present invention further relates to a polynucleotide encoding the recombinant virus of the family Paramyxoviridae according to the present invention.

The present invention also relates to a medicament comprising the recombinant virus of the family Paramyxoviridae of the present invention and at least one pharmacologically acceptable excipient.

The terms "medicament" and "pharmaceutical composition", as used herein, relate to the compounds of the present invention and optionally one or more pharmaceutically acceptable carrier, i.e. excipient. The compounds of the present invention can be formulated as pharmaceutically acceptable salts. Acceptable salts comprise acetate, methylester, HCl, sulfate, chloride and the like. The pharmaceutical compositions are, preferably, administered topically or systemically. Suitable routes of administration conventionally used for drug administration are oral, intravenous, or parenteral administration as well as inhalation. A preferred route of administration is intra-tumoral administration. However, depending on the nature and mode of action of a compound, the pharmaceutical compositions may be administered by other routes as well. For example, polynucleotide compounds may be administered in a gene therapy approach by using viral vectors or viruses or liposomes.

Moreover, the compounds can be administered in combination with other drugs either in a common pharmaceutical composition or as separated pharmaceutical compositions wherein said separated pharmaceutical compositions may be provided in form of a kit of parts. The compounds are, preferably, administered in conventional dosage forms prepared by combining the drugs with standard pharmaceutical carriers according to conventional procedures. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables.

The excipient(s) must be acceptable in the sense of being compatible with the other ingredients of the formulation and being not deleterious to the recipient thereof. The excipient employed may be, for example, a solid, a gel or a liquid carrier. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pa. The diluent(s) is/are selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

A therapeutically effective dose refers to an amount of the compounds to be used in a pharmaceutical composition of the present invention which prevents, ameliorates or treats the symptoms accompanying a disease or condition referred to in this specification. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The dosage regimen will be determined by the attending physician and other clinical factors; preferably in accordance with any one of the above described methods. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment. A typical dose can be, for example, in the range of 1 to 1000 µg for a polypeptide or polynucleotide, or $10^4$-$10^8$ viral particles for a virus or a virus-like particle; however, doses below or above this exemplary range are envisioned, especially considering the aforementioned factors. Progress can be monitored by periodic assessment. The pharmaceutical compositions and formulations referred to herein are administered at least once in order to treat or ameliorate or prevent a disease or condition recited in this specification. However, the said pharmaceutical compositions may be administered more than one time, for example from one to four times daily up to a non-limited number of days. Specific pharmaceutical compositions are prepared in a manner well known in the pharmaceutical art and comprise at least one active compound referred to herein above in admixture or otherwise associated with a pharmaceutically acceptable carrier or diluent. For making those specific pharmaceutical compositions, the active compound(s) will usually be mixed with a carrier or the diluent, or enclosed or encapsulated in a capsule, sachet, cachet, paper or other suitable containers or vehicles. The resulting formulations are to be adapted to the mode of administration, i.e. in the forms of tablets, capsules, suppositories, solutions, suspensions or the like. Dosage recommendations shall be indicated in the prescribers or users instructions in order to anticipate dose adjustments depending on the considered recipient.

The present invention further relates to a method for treating cancer in a subject afflicted with cancer, comprising
a) contacting said subject with a recombinant virus of the family Paramyxoviridae according to the present invention, and
b) thereby, treating cancer in a subject afflicted with cancer.

The method of treatment of the present invention, preferably, may comprise steps in addition to those explicitly mentioned above. For example, further steps may relate, e.g., to localizing a tumor and/or diagnosing cancer for step a), or administration of additional medication for step b). Moreover, one or more of said steps may be performed by automated equipment. The method of the present invention, preferably, is an in vivo method of treatment.

The term "treatment" refers to an amelioration of the diseases or disorders referred to herein or the symptoms accompanied therewith to a significant extent. Said treating as used herein also includes an entire restoration of the health with respect to the diseases or disorders referred to herein. It is to be understood that treating as used in accordance with the present invention may not be effective in all subjects to be treated. However, the term shall require that a statistically significant portion of subjects suffering from a disease or disorder referred to herein can be successfully treated. Whether a portion is statistically significant can be determined without further ado by the person skilled in the art using various well known statistic evaluation tools, e.g., determination of confidence intervals, p-value determination, Student's t-test, Mann-Whitney test etc. Preferred confidence intervals are at least 90%, at least 95%, at least 97%, at least 98% or at least 99%. The p-values are, preferably, 0.1, 0.05, 0.01, 0.005, or 0.0001. Preferably, the treatment shall be effective for at least 60%, at least 70%, at least 80%, or at least 90% of the subjects of a given cohort or population. Preferably, treating cancer is reducing tumor burden in a subject.

As used herein, the term "subject" relates to a vertebrate. Preferably, the subject is a mammal, more preferably, a mouse, rat, cat, dog, hamster, guinea pig, sheep, goat, pig, cattle, or horse. Still more preferably, the subject is a primate. Most preferably, the subject is a human. Preferably, the subject is afflicted with a disease caused or aggravated by an insufficient response of the immune response of said subject, more preferably, the subject is afflicted with cancer.

The term "cancer", as used herein, relates to a disease of an animal, including man, characterized by uncontrolled growth by a group of body cells ("cancer cells"). This uncontrolled growth may be accompanied by intrusion into and destruction of surrounding tissue and possibly spread of cancer cells to other locations in the body. Preferably, also included by the term cancer is a relapse.

Preferably, the cancer is selected from the list consisting of acute lymphoblastic leukemia, acute myeloid leukemia, adrenocortical carcinoma, aids-related lymphoma, anal cancer, appendix cancer, astrocytoma, atypical teratoid, basal cell carcinoma, bile duct cancer, bladder cancer, brain stem glioma, breast cancer, burkitt lymphoma, carcinoid tumor, cerebellar astrocytoma, cervical cancer, chordoma, chronic lymphocytic leukemia, chronic myelogenous leukemia, colon cancer, colorectal cancer, craniopharyngioma, endometrial cancer, ependymoblastoma, ependymoma, esophageal cancer, extracranial germ cell tumor, extragonadal germ cell tumor, extrahepatic bile duct cancer, gallbladder cancer, gastric cancer, gastrointestinal stromal tumor, gestational trophoblastic tumor, hairy cell leukemia, head and neck cancer, hepatocellular cancer, hodgkin lymphoma, hypopharyngeal cancer, hypothalamic and visual pathway glioma, intraocular melanoma, kaposi sarcoma, laryngeal cancer, medulloblastoma, medulloepithelioma, melanoma, merkel cell carcinoma, mesothelioma, mouth cancer, multiple endocrine neoplasia syndrome, multiple myeloma, mycosis fungoides, nasal cavity and paranasal sinus cancer, nasopharyngeal cancer, neuroblastoma, non-hodgkin lymphoma, non-small cell lung cancer, oral cancer, oropharyngeal cancer, osteosarcoma, ovarian cancer, ovarian epithelial cancer, ovarian germ cell tumor, ovarian low malignant potential tumor, pancreatic cancer, papillomatosis, paranasal sinus and nasal cavity cancer, parathyroid cancer, penile cancer, pharyngeal cancer, pheochromocytoma, pituitary tumor, pleuropulmonary blastoma, primary central nervous system lymphoma, prostate cancer, rectal cancer, renal cell cancer, retinoblastoma, rhabdomyosarcoma, salivary gland cancer, sézary syndrome, small cell lung cancer, small intestine cancer, soft tissue sarcoma, squamous cell carcinoma, squamous neck cancer, testicular cancer, throat cancer, thymic carcinoma, thymoma, thyroid cancer, urethral cancer, uterine sarcoma, vaginal cancer, vulvar cancer, waldenstrom macroglobulinemia, and wilms tumor. More preferably, the cancer is a solid cancer, a metastasis, or a relapse thereof. Most preferably, the cancer is a solid superficial tumor derived from head and neck cancer, malignant melanoma or cutaneous T cell lymphoma.

The present invention further relates to an in vitro method for activating immune cells in a sample comprising cancer cells and immune cells, comprising
a) contacting said sample comprising cancer cells and immune cells with a recombinant virus of the family Paramyxoviridae according to the present invention, and
b) thereby, activating immune cells comprised in said sample.

The method for activating immune cells may comprise steps in addition to those explicitly mentioned above. For example, further steps may relate, e.g., to providing the recombinant virus of the family Paramyxoviridae for step a), administering further activating compounds, e.g. cytokines, to the immune cells in step b), or separating immune cells from cancer cells after step b). Moreover, one or more of said steps may be performed by automated equipment.

The present invention also relates to a recombinant virus of the family Paramyxoviridae according to the present invention for use in medical treatment.

Moreover, the present invention relates to a recombinant virus of the family Paramyxoviridae for use in treatment of inappropriate cell proliferation.

The term "inappropriate cell proliferation" relates to any proliferation of cells of a subject which is not appropriate to the physiological state of said subject and/or to the tissue context of said cells. Preferably, inappropriate cell proliferation is caused or aggravated by an inhibition of the immune system, more preferably of T-cells. More preferably, inappropriate cell proliferation is cancer.

The present invention further relates to a kit comprising at least the recombinant virus of the family Paramyxoviridae housed in a container.

The term "kit", as used herein, refers to a collection of the aforementioned components. Preferably, said components are combined with additional components, preferably within an outer container. The outer container, also preferably, comprises instructions for carrying out a method of the present invention. Examples for such the components of the kit as well as methods for their use have been given in this specification. The kit, preferably, contains the aforementioned components in a ready-to-use formulation. Preferably, the kit may additionally comprise instructions, e.g., a user's manual for applying the recombinant virus of the family Paramyxoviridae with respect to the applications provided by the methods of the present invention. Details are to be found elsewhere in this specification. Additionally, such user's manual may provide instructions about correctly using the components of the kit. A user's manual may be provided in paper or electronic form, e.g., stored on CD or CD ROM. The present invention also relates to the use of said kit in any of the methods according to the present invention.

Summarizing the findings of the present invention, the following embodiments are preferred:

Embodiment 1

A recombinant virus of the family Paramyxoviridae, comprising at least one expressible polynucleotide encoding a secreted activator of the immune response.

Embodiment 2

The recombinant virus of the family Paramyxoviridae of embodiment 1, wherein said recombinant virus is a recombinant Morbillivirus, preferably, a recombinant measles virus (MV).

Embodiment 3

The recombinant MV of embodiment 2, wherein the recombinant MV is derived from MV strain Edmonston A or B, preferably vaccine strain Schwarz (Edmonston A).

Embodiment 4

The recombinant virus of the family Paramyxoviridae of any one of embodiments 1 to 3, wherein the secreted activator of the immune response is a ligand for an immune checkpoint blockade protein.

Embodiment 5

The recombinant virus of the family Paramyxoviridae of any one of embodiments 1 to 4, wherein the secreted activator of the immune response is a secreted antagonistic single-chain antibody against CTLA-4.

Embodiment 6

The recombinant virus of the family Paramyxoviridae of any one of embodiments 1 to 5, wherein the secreted activator of the immune response is a secreted antagonistic single-chain antibody against CTLA-4 comprising the amino acid sequence of SEQ ID NO:1.

Embodiment 7

The recombinant virus of the family Paramyxoviridae of any one of embodiments 1 to 6, wherein the at least one expressible polynucleotide encoding a secreted activator of the immune response comprises the nucleic acid sequence of SEQ ID NO:2.

Embodiment 8

The recombinant virus of the family Paramyxoviridae of any one of embodiments 1 to 4, wherein the secreted activator of the immune response is a secreted antagonistic single-chain antibody against PD-L1.

Embodiment 9

The recombinant virus of the family Paramyxoviridae of any one of embodiments 1 to 4, wherein the secreted activator of the immune response is a secreted antagonistic single-chain antibody against PD-L1 comprising the amino acid sequence of SEQ ID NO:3.

Embodiment 10

The recombinant virus of the family Paramyxoviridae of any one of embodiments 1 to 4, wherein the at least one expressible polynucleotide encoding a secreted activator of the immune response comprises the nucleic acid sequence of SEQ ID NO:4.

Embodiment 11

The recombinant virus of the family Paramyxoviridae of any one of embodiments 1 to 10, wherein the at least one expressible polynucleotide encoding a secreted activator of the immune response is comprised in the polynucleotide encoding the recombinant virus of the family Paramyxoviridae.

Embodiment 12

The recombinant virus of the family Paramyxoviridae of any one of embodiments 1 to 11, further comprising a second expressible polynucleotide encoding a second secreted activator of the immune response.

Embodiment 13

The recombinant virus of the family Paramyxoviridae of any one of embodiments 1 to 12, wherein said second expressible polynucleotide encoding a secreted activator of the immune response is a cytokine or a second antagonist of an inhibitory factor of a T-cell or an antagonist of a negative immune regulator of the tumor-immune microenvironment.

Embodiment 14

A polynucleotide encoding the recombinant virus of the family Paramyxoviridae according of any one of embodiments 1 to 13.

Embodiment 15

The polynucleotide of embodiment 14, wherein said polynucleotide comprises the nucleic acid sequence of SEQ ID NO: 6, 7, 8, or/and 9.

Embodiment 16

A medicament comprising the recombinant virus of the family Paramyxoviridae of any one of embodiments 1 to 13 and/or the polynucleotide of embodiment 14 or 15, and at least one pharmacologically acceptable excipient.

Embodiment 17

A method for treating cancer in a subject afflicted with cancer, comprising
a) contacting said subject with a recombinant virus of the family Paramyxoviridae according of any one of embodiments 1 to 13 and/or with a polynucleotide according to embodiment 14 or 15, and
b) thereby, treating cancer in a subject afflicted with cancer.

Embodiment 18

The method of embodiment 17, wherein said cancer is a solid cancer, a metastasis, or a relapse thereof.

Embodiment 19

The method of embodiment 17 or 18, wherein treating cancer is reducing tumor burden.

Embodiment 20

The method of any one of embodiments 17 to 19, wherein said cancer is malignant melanoma, head and neck cancer, hepatocellular carcinoma, pancreatic carcinoma, prostate cancer, renal cell carcinoma, gastric carcinoma, colorectal carcinoma, lymphomas or leukemias.

Embodiment 21

An in vitro method for treating activating immune cells in a sample comprising cancer cells and immune cells, comprising
a) contacting said sample comprising cancer cells and immune cells with a recombinant virus of the family Paramyxoviridae of any one of embodiments 1 to 13 and/or with a polynucleotide according to embodiment 14 or 15, and
b) thereby, activating immune cells comprised in said sample.

Embodiment 22

A recombinant virus of the family Paramyxoviridae according to any one of embodiments 1 to 13 for use in medical treatment.

Embodiment 23

A recombinant virus of the family Paramyxoviridae according to any one of embodiments 1 to 13 and/or a polynucleotide according to embodiment 14 or 15 for use in treatment of inappropriate cell proliferation.

Embodiment 24

The recombinant virus of the family Paramyxoviridae for use of embodiment 24, wherein treatment of inappropriate cell proliferation is cancer treatment.

Embodiment 25

Kit comprising at least the recombinant virus of the family Paramyxoviridae according to any one of embodiments 1 to 13 and/or with a polynucleotide according to embodiment 14 or 15 housed in a container.

All references cited in this specification are herewith incorporated by reference with respect to their entire disclosure content and the disclosure content specifically mentioned in this specification.

FIGURE LEGENDS

FIG. 1 shows a schematic representation of recombinant Measles Virus (MV) genomes. Top panel: MV encoding a secretable antibody (s$\alpha$Y) for immune checkpoint modulation bottom panel: MV encoding a secretable antibody for immune checkpoint modulation and a second additional immunomodulatory transgene (X).

Figure 2:
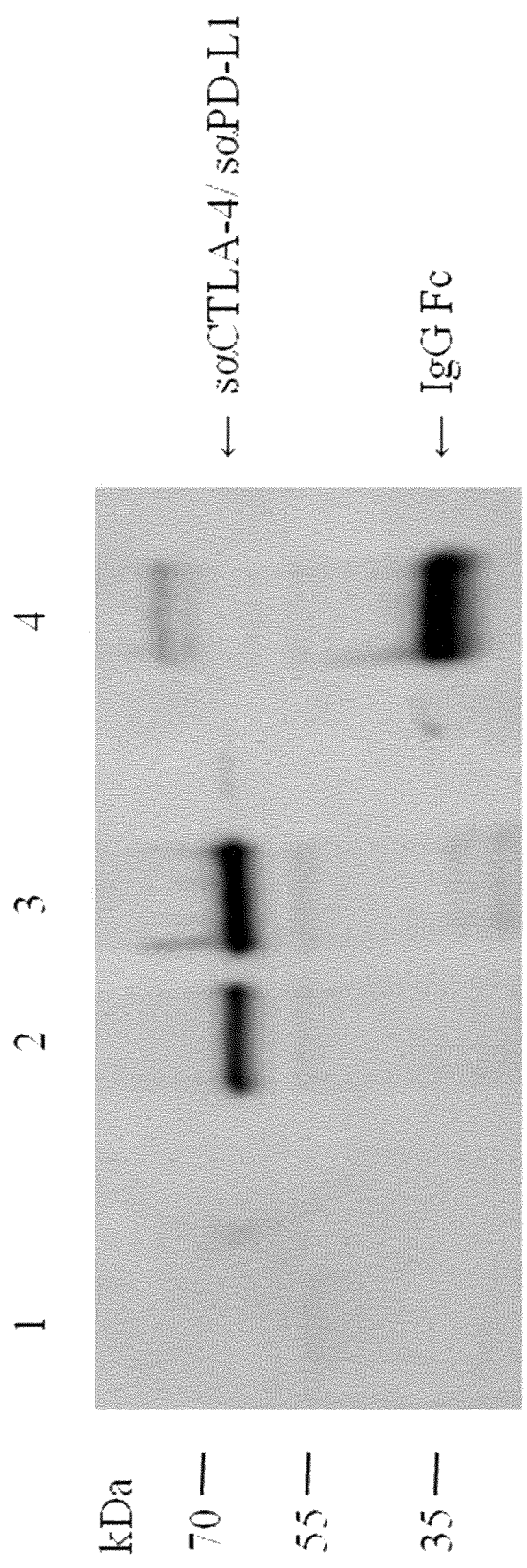

FIG. 2 shows a Western Blot of culture supernatants of cells infected with MV-s$\alpha$Y variants. These data demonstrate that the encoded antibodies against CTLA-4 and PD-L1, respectively, are synthesized in full-length and secreted. Lane 1: MV-EGFP (control virus expressing EGFP); lane 2: MV H-s$\alpha$CTLA-4; lane 3: MV H-s$\alpha$PD-L1; lane 4: MV H-IgG Fc (control, expressing only the antibody constant region)

Figure 3:
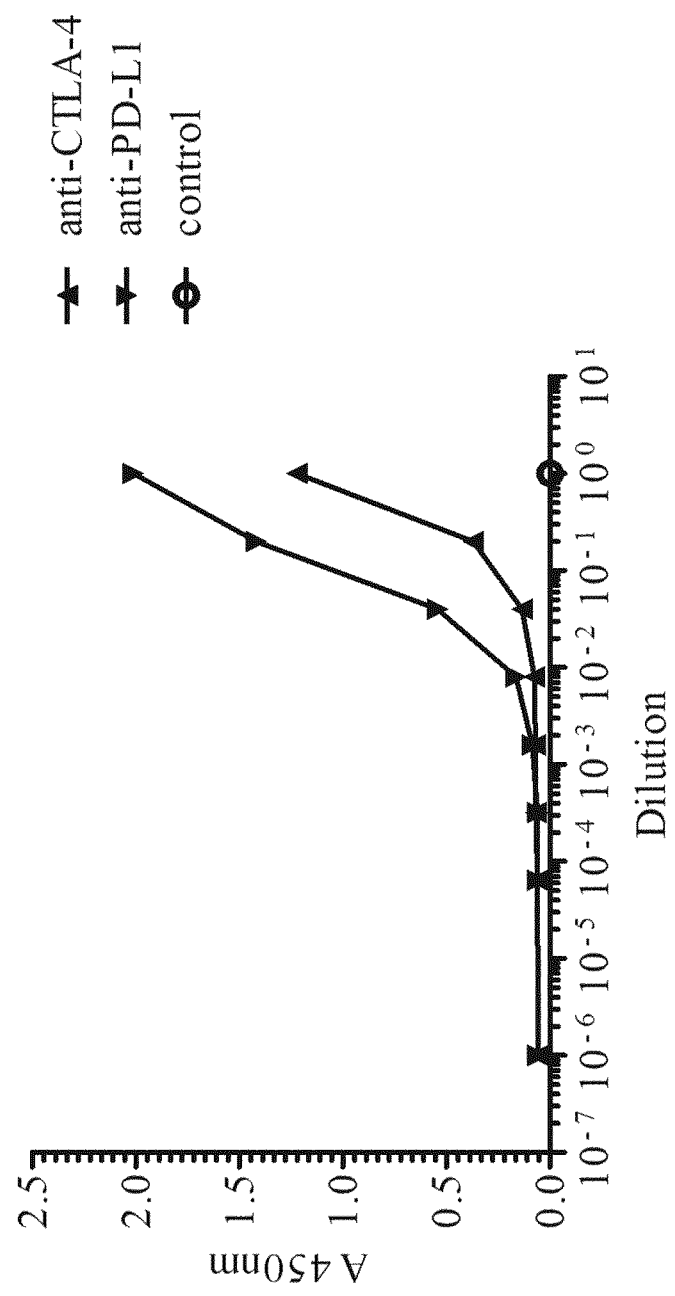

FIG. 3 shows an ELISA for the binding of the MV-encoded secretable antibody to its respective antigen. Optical density is given as adsorption values at 450 nm vs. dilutions of culture supernatants of cells infected with the MV-s$\alpha$Y variants. These data demonstrate specific recognition of and binding to the cognate antigen (s$\alpha$CTLA-4 to CTLA-4 and s$\alpha$PD-L1 to PD-L1, respectively) without cross-reactions (circle: control). Triangle up: s$\alpha$CTLA-4 to CTLA-4; triangle down: s$\alpha$PD-L1 to PD-L1, respectively, open circle: negative control.

Figure 4:
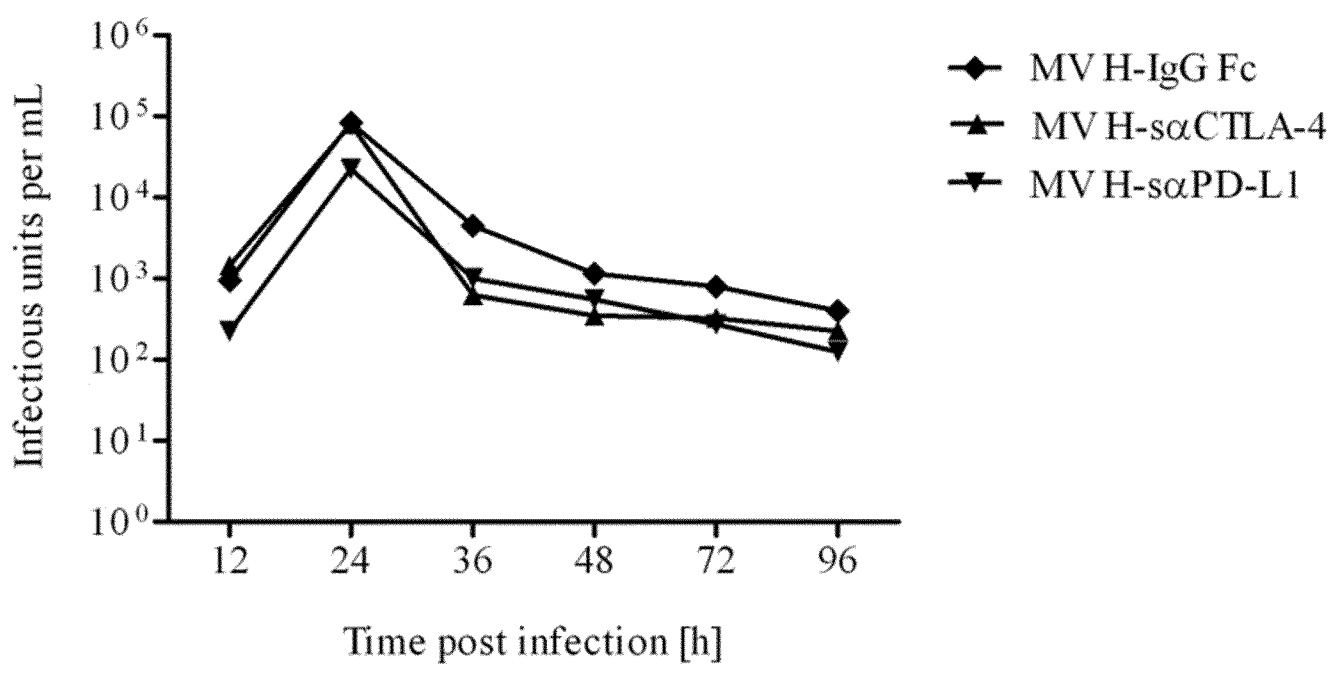

FIG. 4 shows in vitro growth kinetics of recombinant MV-s$\alpha$Y variants in an infected human melanoma cell line. Titers of progeny particles are given as infectious units per ml at the indicated time points for each group. These data demonstrate equal kinetics of both variants which are comparable to the control. Triangle up: MV H-s$\alpha$CTLA-4; triangle down: MV H-s$\alpha$PD-L1; diamond: MV H-IgG Fc (control, expressing only the antibody constant region).

Figure 5:
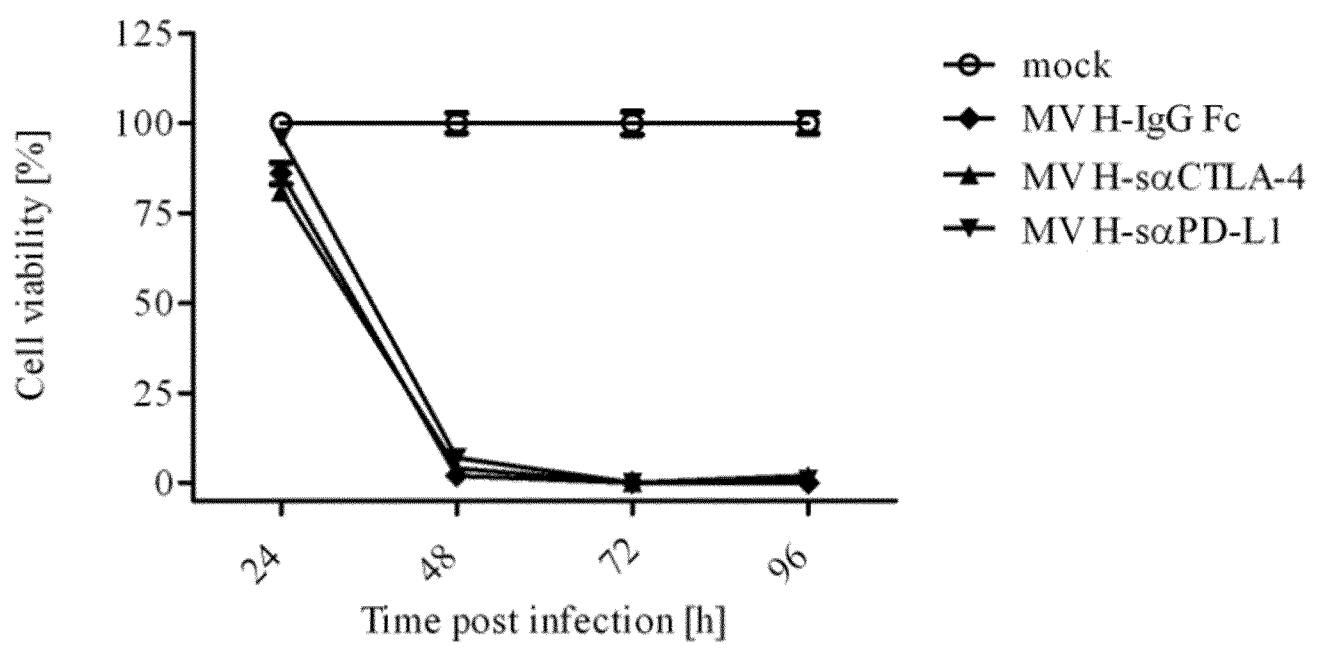

FIG. 5 shows an in vitro cytotoxicity assay (XTT) of human melanoma cell line recombinant MV-s$\alpha$Y variants. Medium cell viability and standard deviations are given as percentage at the indicated time points for each group (mock treated cells defining 100% viability). These data demonstrate equal potential of both variants to lyse tumor cells. Triangle up: MV H-s$\alpha$CTLA-4; triangle down: MV H-s$\alpha$PD-L1; diamond: MV H-IgG Fc (control, expressing only the antibody constant region).

Figure 6:
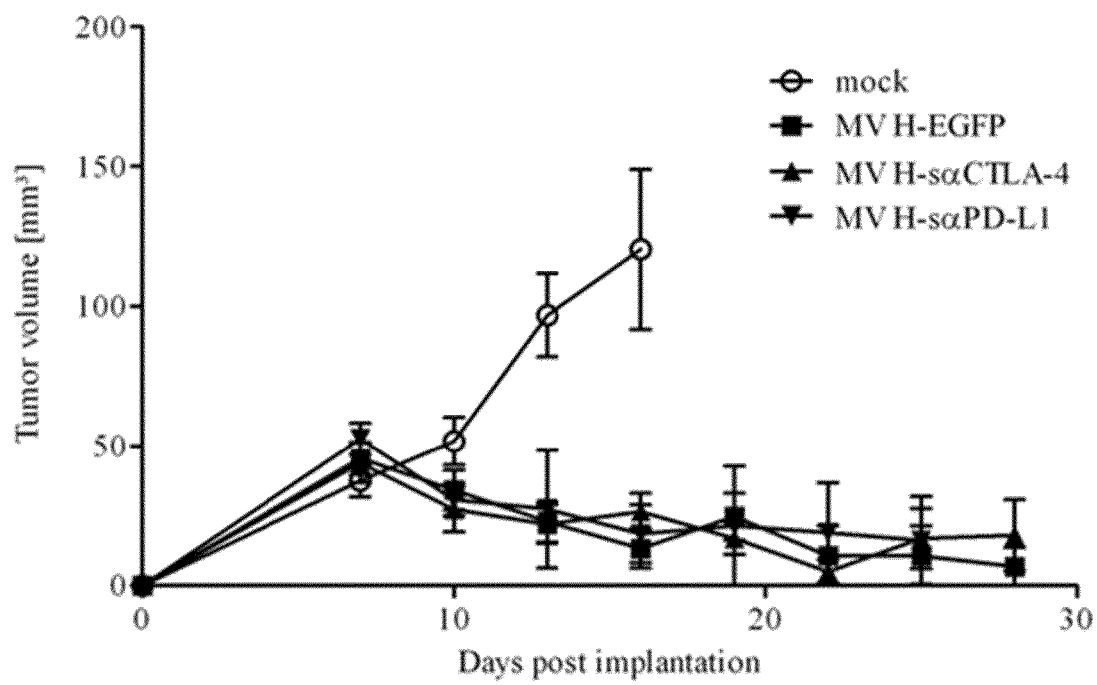
Figure 6:
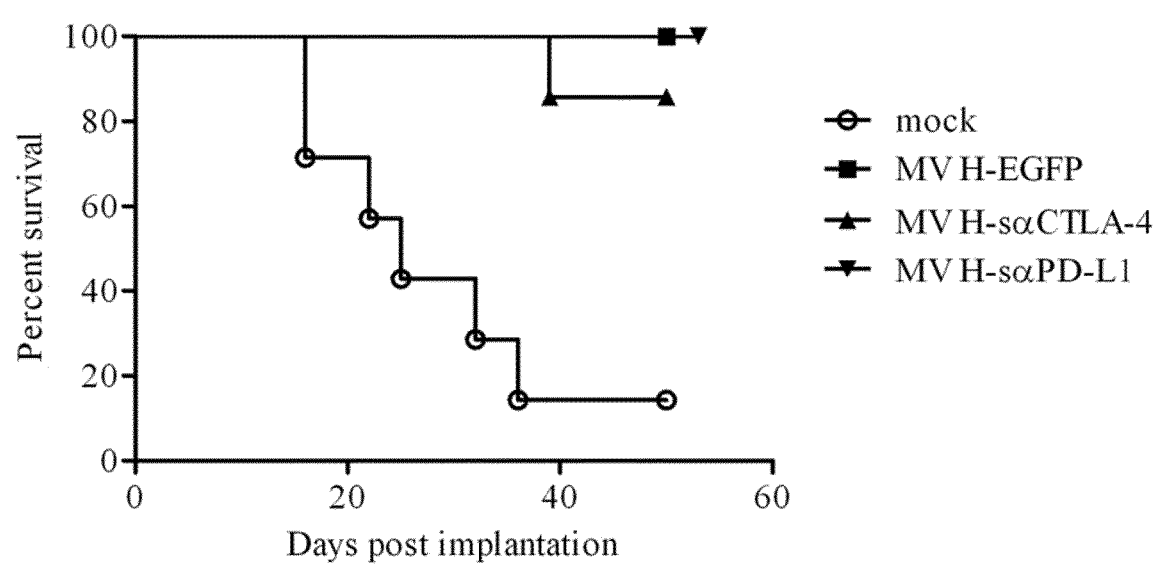

FIG. 6 shows in vivo anti-tumor activity of the recombinant MV-s$\alpha$Y variants against human melanoma in a subcutaneous murine xenograft model. Top panel: tumor volume growth curve ($mm^3$) of treated animal vs. time after implantation (medium volume and standard deviation per group). Square: MV H-EGFP, triangle up: MV H-s$\alpha$CTLA-4, triangle down: MV H-s$\alpha$PD-L1. Bottom panel: Kaplan-Meier plot showing the fraction of treated animals surviving vs. time after implantation of melanoma cells. In this immunodeficient model, MV encoding s$\alpha$CTLA-4 or s$\alpha$PD-L1 were as efficient as a parental control virus for oncolysis of human melanoma.

Figure 7:
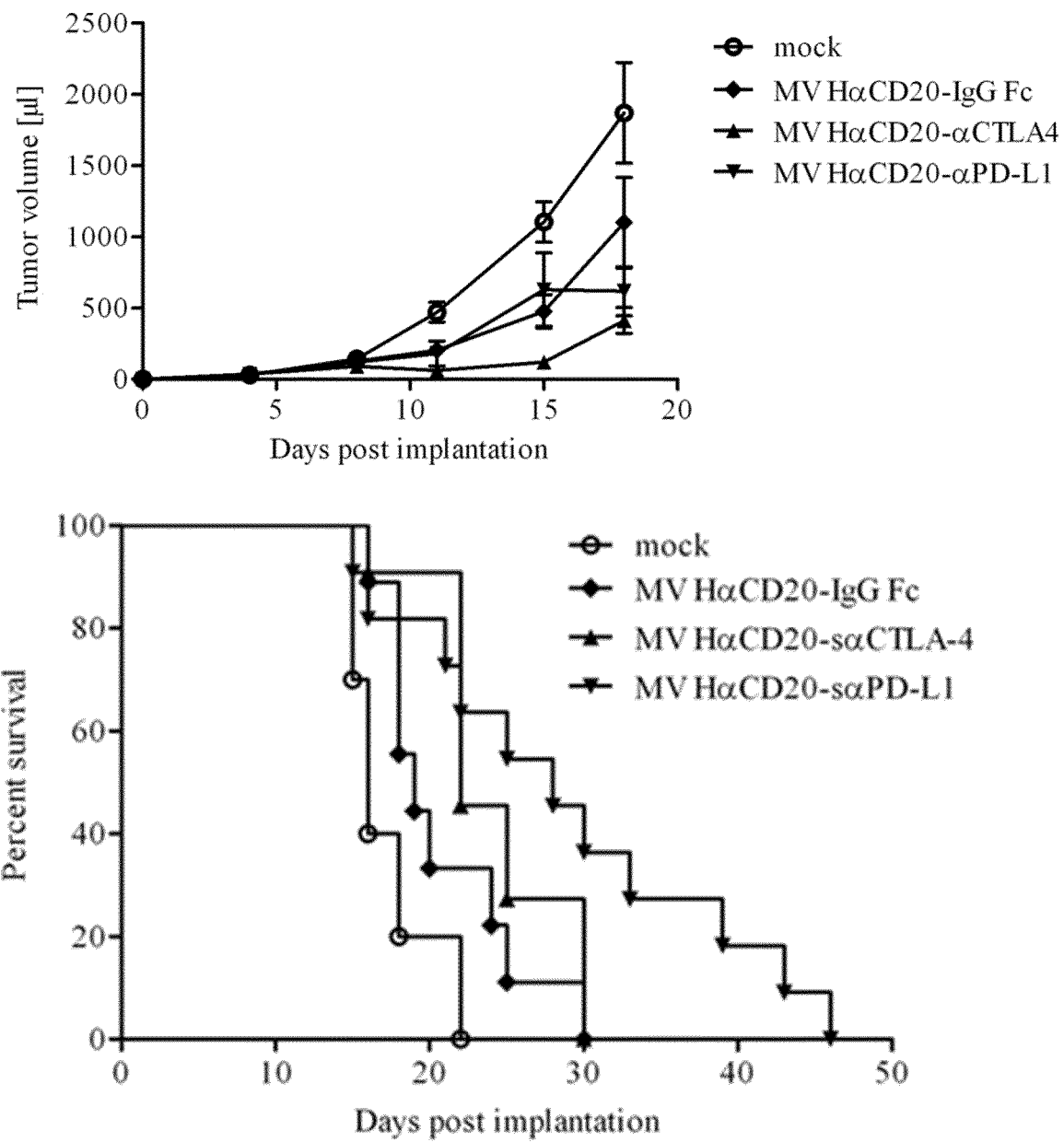

FIG. 7 shows therapeutic effects of the recombinant MV-s$\alpha$Y variants in an immunocompetent model of murine melanoma. Control virus, diamond; MV H$\alpha$CD20-s$\alpha$CTLA-4, triangle up; MV H$\alpha$CD20-s$\alpha$PD-L1, triangle down. Top panel: tumor volume growth curve ($mm^3$) of treated animal vs. time after implantation (medium volume and standard deviation per group), bottom panel: Kaplan- Meier plot showing the fraction of treated animals surviving vs. time after implantation of melanoma cells. Treatment with MV-sαCTLA-4 as well as with MV-sαPD-L1 led to a significant delay of tumor progression, treatment with MV-sαPD-L1 led to a significant prolongation of median overall survival.

Figure 8:
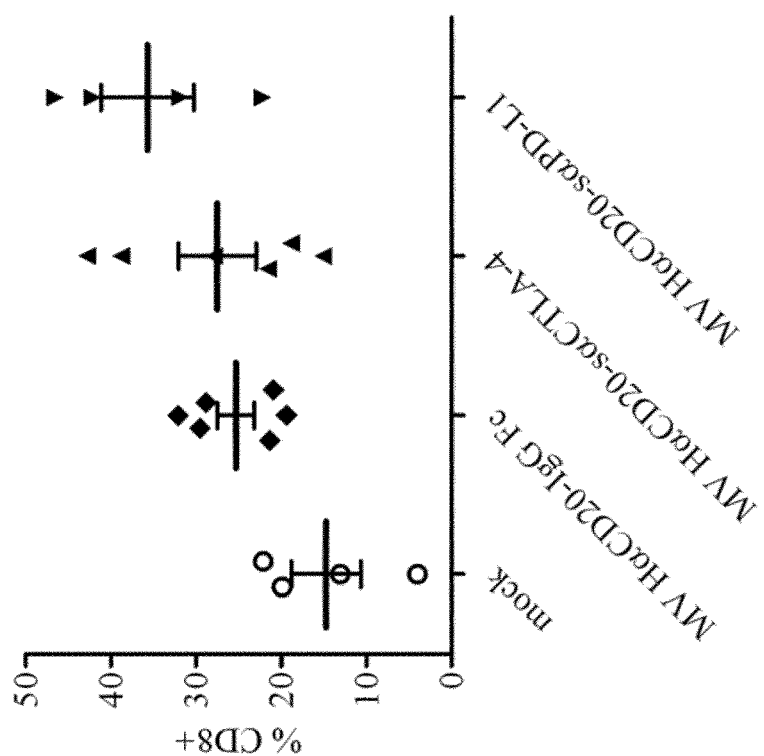
Figure 8:
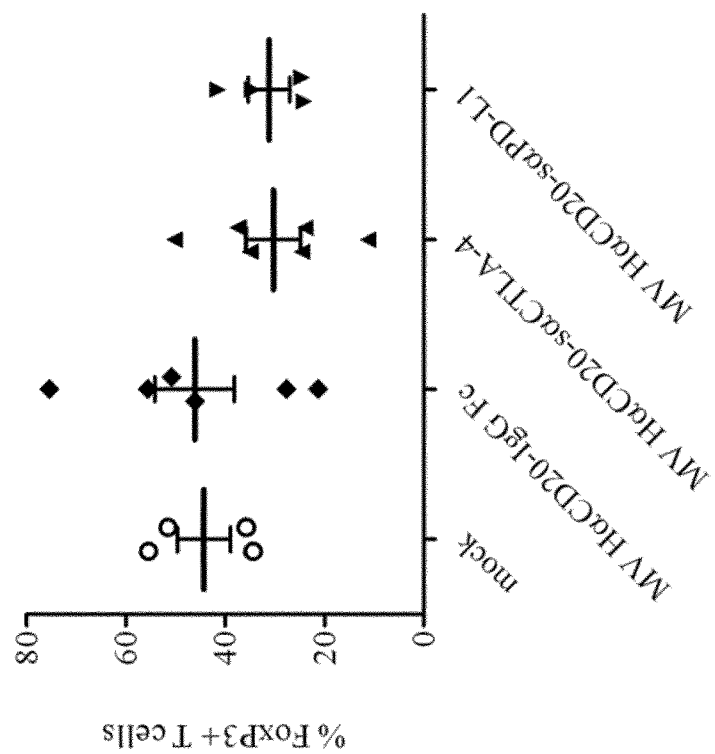

FIG. 8 shows FACS analyses of murine lymphocytes reflecting in vivo effects of the recombinant MV-sαY variants on tumor-infiltrating lymphocytes after treatment of immunocompetent mice bearing syngeneic melanoma tumors. The FACS analyses demonstrate equal downregulation of regulatory T cells (FOXP3+, left panel) for both variants and a differentiated regulation of cytotoxic T cells (CD8+, right panel). MV HαCD20-IgG Fc (control virus), diamond; MV HαCD20-sαCTLA-4, triangle up; MV HαCD20-sαPD-L1, triangle down. Mock treated animals received carrier fluid only (circle).

The following Examples shall merely illustrate the invention. They shall not be construed, whatsoever, to limit the scope of the invention.

EXAMPLE 1. GENERATION OF RECOMBINANT MEASLES VIRUSES

Construction of Recombinant MV Genomes in DNA Plasmids

The genome of the measles vaccine strain Schwarz (Genbank Acc NO: AF266291.1 GI:9181912) was cloned into a pUC19-based plasmid. For later generation of viral particles from a DNA plasmid in a transfected mammalian host cell line, the 5'-end of the MV leader was fused to the CMV minimal promoter, and the 3'-end of the MV trailer is followed by the Hepatitis Delta virus ribozyme sequence and a eukaryotic polyA signal (note: with respect to the natural 3'→5'-orientation of negative-strand (−)RNA viruses, the sequence of the DNA copy is annotated in the usual 5 '→3'-orientation; this corresponds to the viral sequence in antigenomic (+)RNA orientation; the same condition applies for the cloned viral genome with respect to the direction of the CMV promoter-driven transcription through RNA polymerase II). An additional MV-specific transcription unit (ATU) was inserted into the 3'-untranslated region (UTR) of the H gene. The H-ATU consists of viral transcription control elements—a copy of gene end signal from the N gene and gene start signal of the P gene—and the unique cloning site MauBI for insertion of transgenic open reading frames (ORF).

The coding sequences for the claimed immunomodulatory transgenes were cloned into a mammalian expression vector, providing a secretion signal and a HA-tag at the N-terminus as well as a myc-tag at the C-terminus. The respective ORFs were excised as 5 '-MluI 3'-AscI fragments and inserted into the MV H-ATU plasmid via the compatible MauBI site, leading to the novel vectors (FIG. 1). Due to technical reasons, in later infection experiments of murine cells, the H protein was replaced by the fully re-targeted HαCD20 (Ungerechts et al., Cancer Res. 2007, 67: 10939-10947). Thus, transgenic murine cells expressing CD20 can be infected via re-targeted MV.

Generation and Propagation of Recombinant MV

Recombinant MV particles were generated from cDNA constructs according to Martin et al. (J Virol. 2006; 80: 5708-5715) with slight modifications. Vero cells (5×10⁵ per 6-well) were transfected with 5 μg of the recombinant MV plasmid, together with 500 ng N, 100 ng P and 500 ng L expression plasmids using FugeneHD at a ratio of 3:1. Four to six days after transfection, cell culture supernatants were transferred onto fresh cells. To prepare virus stocks, Vero cells (African green monkey, normal kidney) were infected at a MOI of 0.03 and incubated at 37° C. for 36 to 48 hours. Viral particles were harvested by one freeze/thaw cycle and centrifugation from their cellular substrate resuspended in Opti-MEM (Invitrogen). Virus preparations can be further purified by GMP-complying protocols for ultracentrifugation or tangential flow filtration. All following infection experiments were performed with viral stocks from the third passage. Titers were determined by 50% tissue culture infectious dose ($TCID_{50}$) titration on Vero cells. For generation and propagation of fully re-targeted viruses, all procedures were done analogously using Vero-αHis cells (Nakamura et al., Nat Biotechnol 2005; 23: 209-214).

EXAMPLE 2. CHARACTERIZATION OF CLONED SECRETABLE ANTIBODIES

MV-Mediated Expression of Secretable Antibodies

Human melanoma cells Mel888 were seeded into a six-well plate (1.5×10⁵ per well) and infected with variant viruses at MOI of 1. Twenty-four hours after infection, supernatants were collected and passed through a 0.2 μm filter. Antibodies were precipitated using Protein A Sepharose and detected by immunoblot with an anti-HA antibody (FIG. 2). Arrows indicate full-length antibodies against CTLA-4 and PD-L1 (~60 kDa) and the IgG Fc (~30 kDa) domain, respectively. These data demonstrate that the encoded antibodies against CTLA-4 and PD-L1, respectively, are synthesized in full-length and secreted.

Binding of Secretable Antibodies to their Respective Cognate Antigens

Vero cells were seeded in six-well plates (2×10⁵ cells per well) and infected at MOI of 3 with the indicated viruses. 36 hours after infection, cell culture supernatants were collected and passed through a 0.2 μm filter. Nunc Maxisorp 96-well plates were coated with 100 ng recombinant protein each of CTLA-4 and PD-L1, respectively. Wells were blocked with FBS and a dilution series of equal volumes of supernatants of cells equally treated and infected with MV H-sαY variants were added to the ELISA plates (FIG. 3). After 2 h incubation and washing, the secreted antibodies sαCTLA-4 and sαPD-L1 were detected with anti-HA-Biotin, HRP-Streptavidin and TMB as substrate. Supernatants from MV H-sαCTLA-4 were used as a control for binding to PD-L1 and vice versa (circles). These data demonstrate specific recognition of and binding to the cognate antigen mediated by the respective secretable antibody without cross-reactions.

EXAMPLE 3. GROWTH KINETICS OF THE RECOMBINANT MV IN VITRO

To determine viral growth kinetics in one-step growth curves, human melanoma cells Mel888 were seeded into a six-well plate (1×10⁵ per well) and infected with the indicated MV vectors at an MOI of 3. At designated time points, cells were harvested and progeny viral particles were determined by titration assays (FIG. 4). These data demonstrate equal kinetics of both variants in target melanoma cells and that encoding of secretable full-length antibodies by the MV vector does not impair viral replication.

EXAMPLE 4. CYTOTOXICITY OF THE RECOMBINANT MV IN VITRO

To address the cytolytic effect of MV vectors encoding secretable anti-CTLA-4 and anti-PD-L1 antibodies against human melanoma cells, in vitro infection experiments were performed with Sk-Mel28 and Mel888 cells for qualitative evaluation via microscopic inspection. Syncytia formation on human cell lines was delayed compared to the simian producer cell line Vero. Nevertheless, by 48 hours after infection MV H-sαCTLA-4 and MV H-sαPD-L1 had spread across the entire cell layer. Cytopathic effects were as pronounced as those caused by the control virus MV-EGFP.

Cytopathic effects of oncolytic MV on human and murine melanoma cell lines were quantified by cell viability assays. Human melanoma cells Mel888 were seeded into a six-well plate ($1\times10^5$ per well) and infected with the indicated MV vectors at an MOI of 1. At designated time points after infection, cell viability was determined using the colorimetric XTT assay (FIG. 5). Viability of mock treated cells was defined as 100%. Both recombinant MV H-sαY variants rapidly lysed melanoma cells, leading to complete cell killing after 48 hours, demonstrating equal potential of both variants to lyse tumor cells.

EXAMPLE 5. IN VIVO ANTI-TUMOR ACTIVITY OF THE RECOMBINANT MV IN A XENOGRAFT MODEL

Oncolytic efficacy of MV expressing secretable antibodies was assessed in a xenograft model of human melanoma (FIG. 6). $5\times10^6$ Mel888 cells were implanted subcutaneously into the right flank region of NOD/SCID mice. When tumors reached an average volume of 50 $mm^3$, mice received intratumoral injections of $2\times10^6$ cell infectiuos units (ciu) per dose on five consecutive days applying MV H-EGFP (control virus), MV H-sαCTLA-4 or MV H-sαPD-L1. Mock treated animals received carrier fluid only. Tumor volumes were determined every third day using a caliper. Mice were sacrificed when tumor volumes exceeded 1500 $mm^3$ or when tumor ulceration occurred.

MV treatment led to a significant delay in tumor progression (FIG. 6, top panel). On day 19 after implantation (seven days after the last treatment), mock treated mice had a mean tumor volume of 115 μl, while the mean tumor volume in mice treated with MV was 25 μl (square: MV H-EGFP), 20 μl (triangle up: MV H-sαCTLA-4) and 21 μl (triangle down: MV H-sαPD-L1), respectively. Mean tumor volumes and standard error bars for each group are shown.

MV treatment led to a significant survival benefit (FIG. 6, bottom panel). Median overall survival was 24 days for mock controls, whereas all but one of the MV-treated mice survived over 50 days after tumor implantation. Complete tumor remission and long-term survival was observed in 85% of treated animals.

In this immunodeficient model, MV encoding sαCTLA-4 or sαPD-L1 were both as efficient as a parental control virus for oncolysis of human melanoma.

EXAMPLE 6. IN VIVO THERAPEUTIC EFFECTS IN AN IMMUNOCOMPETENT MURINE MELANOMA MODEL

Therapeutic efficacy of immunovirotherapy in vivo was assessed in a syngeneic immunocompetent murine melanoma model (FIG. 7). $1\times10^6$ B16-CD20 cells (transgenic mouse melanoma cell line expressing CD20 ectopically for CD20-targeted MV infection) were implanted subcutaneously into the right flank region of C57BL/6 mice. When tumors reached an average volume of 50 $mm^3$, mice received intratumoral injections of $2\times10^6$ ciu per dose on five consecutive days applying MV HαCD20-IgG Fc (control virus, diamond, n=9), MV HαCD20-sαCTLA-4 (triangle up, n=11) or MV HαCD20-sαPD-L1 (triangle down, n=11). Mock treated animals received carrier fluid only (circle, n=10).

Treatment with MV expressing the secretable antibody variants led to a delay in tumor progression in both cases (FIG. 7, top panel). Tumor volumes on day 15 after implantation revealed a significantly lower tumor volume in mice treated with MV-sαCTLA-4 compared to mock and MV-IgG Fc controls ($p<0.0001$ and $p=0.036$ in paired students' t-test, respectively). In case of mice treated with MV-sαPD-L1, a subgroup of mice experienced tumor remission.

While reduced tumor volumes at early time points did not prolong overall survival (FIG. 7, bottom panel) in mice treated with MV-sαCTLA-4, mice responding to MV-sαPD-L1 also survived longer compared to mock and IgG Fc controls ($p=0.0047$ and $p=0.031$ in log rank test, respectively).

EXAMPLE 7. IN VIVO EFFECTS OF THE RECOMBINANT MV ON TUMOR-INFILTRATING LYMPHOCYTES

To investigate possible mechanisms of immunomodulatory effects by MV-mediated checkpoint blockade, tumor-infiltrating lymphocytes were characterized by flow cytometry (FIG. 8). Immunomodulatory effects were assessed in a syngeneic immunocompetent murine melanoma model. $1\times10^6$ B16-CD20 cells (transgenic mouse melanoma cell line expressing CD20 ectopically for CD20-targeted MV infection) were implanted subcutaneously into the right flank region of C57BL/6 mice. When tumors reached an average volume of 50 $mm^3$, mice received intratumoral injections of $2\times10^6$ ciu per dose on five consecutive days applying MV HαCD20-IgG Fc (control virus, diamond), MV HαCD20-sαCTLA-4 (triangle up) or MV HαCD20-sαPD-L1 (triangle down). Mock treated animals received carrier fluid only (circle). Twenty-four hours after the last treatment, mice were sacrificed and tumors were explanted. Single-cell suspensions of tumors were stained with antibodies specific for CD45.2, CD3, CD8, CD4 and CD25. Cells were fixed, permeabilized and stained with a FoxP3-specific antibody. Tumor-infiltrating lymphocytes were analyzed by flow cytometry of the stained samples using AriaII and FACS DIVA Software. Left panel: The Abundance of CD3+ CD4+ CD25+ FoxP3+ regulatory T cells as percentage of all CD3+ T cells is shown for each treatment group. Right panel: The Abundance of CD3+ CD8+ cytotoxic T cells as percentage of all T cells is shown for each treatment group.

Treatment with MV H-sαCTLA-4 and MV H-sαPD-L1 led to a favorable immune profile with lower abundance of negative regulatory T cells and, particularly in the case of MV H-sαPD-L1, to a higher abundance of cytotoxic T cells in treated tumors. The data suggest that MV-mediated blockade of CTLA-4 as well as of PD-L1 leads to beneficial reduction of regulatory T cells, whereas only PD-L1 inhibition led to a statistically significant increase in cytotoxic T cells.

The invention claimed is:

1. A polynucleotide encoding a recombinant virus of the family Paramyxoviridae, the polynucleotide comprising the nucleic acid sequence of SEQ ID NO: 6, 7, 8, and/or 9, wherein the recombinant virus comprises at least one expressible polynucleotide encoding a secreted activator of the immune response.

2. The polynucleotide of claim 1, wherein said recombinant virus is a recombinant Morbillivirus.

3. The polynucleotide of claim 2, wherein said recombinant Morbillivirus is a recombinant measles virus (MV).

4. The polynucleotide of claim 3, wherein the recombinant MV is derived from vaccine strain Schwarz (Edmonston A).

5. The polynucleotide of claim 1, wherein the secreted activator of the immune response is a ligand for an immune checkpoint blockade protein.

6. The polynucleotide of claim 1, wherein the secreted activator of the immune response is a secreted antagonistic single-chain antibody against CTLA 4.

7. The polynucleotide of claim 6, wherein the secreted antagonistic single-chain antibody against CTLA-4 comprises the amino acid sequence of SEQ ID NO:1.

8. The polynucleotide of claim 1, wherein the secreted activator of the immune response is a secreted antagonistic single-chain antibody against PD-L1.

9. The polynucleotide of claim 8, wherein the secreted antagonistic single-chain antibody against PD-L1 comprises the amino acid sequence of SEQ ID NO:3.

10. The polynucleotide of claim 1, further comprising a second expressible polynucleotide encoding a second secreted activator of the immune response.

11. The polynucleotide of claim 10, wherein said second expressible polynucleotide encoding a secreted activator of the immune response is a cytokine or a second antagonist of an inhibitory factor of a T-cell or an antagonist of a negative immune regulator of the tumor-immune microenvironment.

12. A method for treating cancer in a subject afflicted with cancer, comprising
 a) contacting said subject with the polynucleotide according to claim 1, and
 b) thereby, treating cancer in a subject afflicted with cancer.

13. The method of claim 12, wherein said cancer is a solid cancer, a metastasis, or a relapse thereof.

14. The method of claim 12, wherein treating cancer is reducing tumor burden.

15. The method of claim 12, wherein said cancer is malignant melanoma, head and neck cancer, hepatocellular carcinoma, pancreatic carcinoma, prostate cancer, renal cell carcinoma, gastric carcinoma, colorectal carcinoma, lymphomas or leukemias.

16. A kit comprising at least the polynucleotide of claim 1 housed in a container.

17. A medicament comprising the polynucleotide of claim 1, and at least one pharmacologically acceptable excipient.

18. An in vitro method for activating immune cells in a sample comprising cancer cells and immune cells, comprising
- a) contacting said sample comprising cancer cells and immune cells with the polynucleotide according to claim 1, and
- b) thereby, activating immune cells comprised in said sample.

* * * * *

SEQUENCE LISTING

<160> NUMBER OF SEQ ID NOS: 9

<210> SEQ ID NO 1
<211> LENGTH: 499
<212> TYPE: PRT
<213> ORGANISM: Artificial
<220> FEATURE:
<223> OTHER INFORMATION: Single-chain anti-human CTLA-4 antibody,
      secreted; contains homologous secretion signal from human IgG
      variable kappa subgroup III, L6

<400> SEQUENCE: 1

```
Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Gly Ser Ser Tyr Leu Ala Trp Tyr Gln Gln Lys Pro Gly Gln Ala
    50                  55                  60

Pro Arg Leu Leu Ile Tyr Gly Ala Phe Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Ser Pro Trp Thr Phe Gly Gln Gly Thr Lys Val Glu Ile Lys
        115                 120                 125

Arg Gly Gly Gly Gly Ser Gly Gly Gly Gly Ser Gly Gly Gly Gly Ser
    130                 135                 140

Gln Val Gln Leu Val Glu Ser Gly Gly Val Val Gln Pro Gly Arg
145                 150                 155                 160

Ser Leu Arg Leu Ser Cys Ala Ala Ser Gly Phe Thr Phe Ser Ser Tyr
                165                 170                 175

Thr Met His Trp Val Arg Gln Ala Pro Gly Lys Gly Leu Glu Trp Val
            180                 185                 190

Thr Phe Ile Ser Tyr Asp Gly Asn Asn Lys Tyr Tyr Ala Asp Ser Val
        195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Ile Tyr Tyr Cys
225                 230                 235                 240

Ala Arg Thr Gly Trp Leu Gly Pro Phe Asp Tyr Trp Gly Gln Gly Thr
                245                 250                 255

Leu Val Thr Val Ser Ser Val Asp Glu Ala Lys Ser Cys Asp Lys Thr
            260                 265                 270

His Thr Cys Pro Pro Cys Pro Ala Pro Glu Leu Leu Gly Gly Pro Ser
        275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350
```

```
Ser Val Leu Thr Val Leu His Gln Asp Trp Leu Asn Gly Lys Glu Tyr
        355                 360                 365

Lys Cys Lys Val Ser Asn Lys Ala Leu Pro Ala Pro Ile Glu Lys Thr
370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
            405                 410                 415

Leu Val Lys Gly Phe Tyr Pro Ser Asp Ile Ala Val Glu Trp Glu Ser
                420                 425                 430

Asn Gly Gln Pro Glu Asn Tyr Lys Thr Thr Pro Pro Val Leu Asp
            435                 440                 445

Ser Asp Gly Ser Phe Phe Leu Tyr Ser Lys Leu Thr Val Asp Lys Ser
        450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495

Val Asp Asn

<210> SEQ ID NO 2
<211> LENGTH: 1500
<212> TYPE: DNA
<213> ORGANISM: Artificial
<220> FEATURE:
<223> OTHER INFORMATION: coding sequence for sectreted single-chain
      anti-human CTLA-4 antibody;  contains homologous secretion signal
      from human IgG variable kappa subgroup III, L6

<400> SEQUENCE: 2
atggaaaccc cagcacagct tctcttcctc ctgctgctct ggctcccaga taccactgga      60
gagattgtgc tgacgcaatc ccctgggact ctctcccttt ccctggcga acgggctaca     120 ctgtcctgca gagcttcaca gagcgttggg tccagctatc tcgcctggta ccagcagaaa    180
ccaggccaag caccacgcct gctcatctat ggtgcctta gcagagccac tggcataccc     240
gataggttca gcggctcagg cagcggtaca gacttcacgc tgaccattag ccggctggaa    300
cccgaggatt tcgcagtgta ctattgccag cagtatggga ctctccgtg acatttggc      360 caagggacaa aggtggagat aagcgcggt ggtggtggat caggtggagg cggaagtgga    420
ggtggcggat cccaggtaca gctggtcgag tctggtggcg cgtagtgca acccggaaga    480 agtttgcgac tgtcatgcgc agcttctggg tttaccttca gctcctatac aatgcactgg    540
gtcaggcagg ctccagggaa aggcctggag tgggtcacct tcatctctta cgacgggaac    600
aacaagtact acgcggattc agtgaaagga cggtttacca tctcccgcga caattccaag    660 aatacctgt atctccagat gaacagcttg agagccgaag ataccgccat ctactactgt     720
gccaggactg gatggcttgg ccttttgac tactggggcc agggtactct ggtgactgtt     780
agttcagtcg acgaggccaa atcttgtgac aaaactcaca catgcccacc gtgcccagca    840
cccgaactcc tgggggggacc gtcagtcttc ctcttccccc caaaacccaa ggacaccctc    900
atgatctccc ggacccctga ggtcacatgc gtggtggtgg acgtgagcca cgaagaccct    960
gaggtcaagt tcaactggta cgtggacggc gtggaggtgc ataatgccaa gacaaagccg   1020
cgggaggagc agtacaacag cacgtaccgt gtggtcagcg tcctcaccgt cctgcaccag   1080
gactggctga atggcaagga gtacaagtgc aaggtctcca acaaagccct cccagccccc   1140
```

```
atcgagaaaa ccatctccaa agccaagggg cagccccgag aaccacaggt gtacaccctg    1200
cccccatccc gggatgagct gaccaagaac caggtcagcc tgacctgcct ggtcaaaggc    1260
ttctatccca gcgacatcgc cgtggagtgg gagagcaatg gcagccgga gaacaactac     1320 aagaccacgc ctcccgtgct ggactccgac ggctccttct tcctctacag caagctcacc    1380
gtggacaaga gcaggtggca gcaggggaac gtcttctcat gctccgtgat gcatgaggct    1440
ctgcacaacc actacacgca gaagagcctc tccctgtctc cgggtaaagt cgacaattag   1500
```

<210> SEQ ID NO 3
<211> LENGTH: 502
<212> TYPE: PRT
<213> ORGANISM: Artificial
<220> FEATURE:
<223> OTHER INFORMATION: single-chain anti-human PD-L1, secreted;
      contains homologous secretion signal from human IgG variable kappa
      subgroup III, L6

<400> SEQUENCE: 3

```
Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Ala Thr Leu Ser
                20                  25                  30

Leu Ser Pro Gly Glu Arg Ala Thr Leu Ser Cys Arg Ala Ser Gln Ser
            35                  40                  45

Val Ser Ser Tyr Leu Ala Trp Tyr Gln Gln Lys Pro Gly Gln Ala Pro
        50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Thr Phe Gly Gln Gly Thr Lys Val Glu Ile Lys Arg Gly
        115                 120                 125

Gly Gly Gly Ser Gly Gly Gly Ser Gly Gly Gly Ser Gln Val
    130                 135                 140

Gln Leu Val Gln Ser Gly Ala Glu Val Lys Lys Pro Gly Ser Ser Val
145                 150                 155                 160

Lys Val Ser Cys Lys Thr Ser Gly Asp Thr Phe Ser Thr Tyr Ala Ile
                165                 170                 175

Ser Trp Val Arg Gln Ala Pro Gly Gln Gly Leu Glu Trp Met Gly Gly
            180                 185                 190

Ile Ile Pro Ile Phe Gly Lys Ala His Tyr Ala Gln Lys Phe Gln Gly
        195                 200                 205

Arg Val Thr Ile Thr Ala Asp Glu Ser Thr Ser Thr Ala Tyr Met Glu
    210                 215                 220

Leu Ser Ser Leu Arg Ser Glu Asp Thr Ala Val Tyr Phe Cys Ala Arg
225                 230                 235                 240

Lys Phe His Phe Val Ser Gly Ser Pro Phe Gly Met Asp Val Trp Gly
                245                 250                 255

Gln Gly Thr Thr Val Thr Val Ser Ser Val Asp Glu Ala Lys Ser Cys
            260                 265                 270

Asp Lys Thr His Thr Cys Pro Pro Cys Pro Ala Pro Glu Leu Leu Gly
        275                 280                 285
```

Gly Pro Ser Val Phe Leu Phe Pro Pro Lys Pro Lys Asp Thr Leu Met
            290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Lys Leu Thr Val
450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys Val Asp Asn
            500

<210> SEQ ID NO 4
<211> LENGTH: 1509
<212> TYPE: DNA
<213> ORGANISM: Artificial
<220> FEATURE:
<223> OTHER INFORMATION: coding sequence for secreted single-chain
      anti-human PD-L1; contains homologous secretion signal from human
      IgG variable kappa subgroup III, L6

<400> SEQUENCE: 4
atggaaaccc agcacagct tctcttcctc ctgctgctct ggctcccaga taccactgga      60
gagattgtcc tgacacagag cccagctaca ctttccctgt ctccgggcga aagagcaacc    120
ctctcttgca gggctagcca gtctgtcagc tcttatctcg cctggtatca gcagaaacca    180
ggccaggctc ccagactgct gatctacgac gctagcaatc gcgccactgg cataccagca    240
cgcttttcag gtccggcag tggtaccgac ttcaccctga ccatctcctc actggaacct    300
gaggactttg ccgtgtatta ctgtcaacag cggagtaact ggcccacctt tgggcagggc    360
actaaggtgg agatcaaacg cggtggtggt ggatcaggtg gaggcggaag tggaggtggc    420
ggatcccagg tgcaactggt acagagcggc gcagaagtga agaaacccgg tcctcagtg    480 aaggtcagtt gcaagacatc cggggacacc ttctcaacgt atgccattag ctgggttaga    540
caggctcctg gtcaagggct tgagtggatg ggaggtatca ttcccatatt cgggaaagcg    600
cattatgccc agaagttcca aggcagggtc accatcactg ccgatgaatc cacaagtact    660
gcctacatgg agttgagctc cttgcgtagc gaggatactg cggtgtactt tgtgcacgg    720 aagtttcact tcgtttcagg gagcccttc gggatggatg tttggggaca gggtacaacg    780

```
gtgacagtat ccagcgtcga cgaggccaaa tcttgtgaca aaactcacac atgcccaccg    840
tgcccagcac ccgaactcct gggggggaccg tcagtcttcc tcttcccccc aaaacccaag    900
gacaccctca tgatctcccg gacccctgag gtcacatgcg tggtggtgga cgtgagccac    960
gaagaccctg aggtcaagtt caactggtac gtggacggcg tggaggtgca taatgccaag   1020
acaaagccgc gggaggagca gtacaacagc acgtaccgtg tggtcagcgt cctcaccgtc   1080
ctgcaccagg actggctgaa tggcaaggag tacaagtgca aggtctccaa caaagccctc   1140
ccagccccca tcgagaaaac catctccaaa gccaaggggc agccccgaga accacaggtg   1200
tacaccctgc ccccatcccg ggatgagctg accaagaacc aggtcagcct gacctgcctg   1260
gtcaaaggct tctatcccag cgacatcgcc gtggagtggg agagcaatgg gcagccggag   1320
aacaactaca agaccacgcc tcccgtgctg gactccgacg gctccttctt cctctacagc   1380
aagctcaccg tggacaagag caggtggcag caggggaacg tcttctcatg ctccgtgatg   1440
catgaggctc tgcacaacca ctacacgcag aagagcctct ccctgtctcc gggtaaagtc   1500
gacaattaa                                                           1509
```

<210> SEQ ID NO 5
<211> LENGTH: 20
<212> TYPE: PRT
<213> ORGANISM: Homo sapiens

<400> SEQUENCE: 5

```
Glu Thr Pro Ala Gln Leu Leu Phe Leu Leu Leu Leu Trp Leu Pro Asp
1               5                   10                  15

Thr Thr Gly Glu
            20
```

<210> SEQ ID NO 6
<211> LENGTH: 17472
<212> TYPE: DNA
<213> ORGANISM: Artificial
<220> FEATURE:
<223> OTHER INFORMATION: MeV Schwarz virus genome encoding downstream of H optimized cDNA for secretable (human) antibody anti-human CTLA-4 WITHOUT tags; contains homologous secretion signal from human IgG variable kappa subgroup III, L6

<400> SEQUENCE: 6

```
accaaacaaa gttgggtaag gatagttcaa tcaatgatca tcttctagtg cacttaggat     60
tcaagatcct attatcaggg acaagagcag gattagggat atccgagatg gccacacttt    120
taaggagctt agcattgttc aaaagaaaca aggacaaacc acccattaca tcaggatccg    180
gtggagccat cagaggaatc aaacacatta ttatagtacc aatccctgga gattcctcaa    240
ttaccactcg atccagactt ctggaccggt tggtgaggtt aattggaaac ccggatgtga    300
gcgggcccaa actaacaggg gcactaatag gtatattatc cttatttgtg gagtctccag    360
gtcaattgat tcagaggatc accgatgacc ctgacgttag cataaggctg ttagaggttg    420
tccagagtga ccagtcacaa tctggcctta ccttcgcatc aagaggtacc aacatggagg    480
atgaggcgga ccaatacttt tcacatgatg atccaattag tagtgatcaa tccaggttcg    540
gatggttcgg gaacaaggaa atctcagata ttgaagtgca agaccctgag ggattcaaca    600
tgattctggg taccatccta gcccaaattt gggtcttgct cgcaaaggcg gttacggccc    660
cagacacggc agctgattcg gagctaagaa ggtggataaa gtacacccaa caaagaaggg    720
tagttggtga atttagattg gagagaaaat ggttggatgt ggtgaggaac aggattgccg    780
```

```
aggacctctc cttacgccga ttcatggtcg ctctaatcct ggatatcaag agaacacccg      840
gaaacaaacc caggattgct gaaatgatat gtgacattga tacatatatc gtagaggcag      900
gattagccag ttttatcctg actattaagt ttgggataga aactatgtat cctgctcttg      960
gactgcatga atttgctggt gagttatcca cacttgagtc cttgatgaac ctttaccagc     1020
aaatggggga aactgcaccc tacatggtaa tcctggagaa ctcaattcag aacaagttca     1080
gtgcaggatc atacccctctg ctctggagct atgccatggg agtaggagtg gaacttgaaa    1140
actccatggg aggtttgaac tttggccgat cttactttga tccagcatat tttagattag     1200
ggcaagagat ggtaaggagg tcagctggaa aggtcagttc cacattggca tctgaactcg     1260
gtatcactgc cgaggatgca aggcttgttt cagagattgc aatgcatact actgaggaca     1320
agatcagtag agcggttgga cccagacaag cccaagtatc atttctacac ggtgatcaaa     1380
gtgagaatga gctaccgaga ttggggggca aggaagatag gagggtcaaa cagagtcgag     1440
gagaagccag ggagagctac agagaaaccg ggcccagcag agcaagtgat gcgagagctg     1500
cccatcttcc aaccggcaca ccctagaca ttgacactgc aacggagtcc agccaagatc      1560
cgcaggacag tcgaaggtca gctgacgccc tgcttaggct gcaagccatg gcaggaatct     1620
cggaagaaca aggctcagac acggacaccc ctatagtgta caatgacaga aatcttctag     1680
actaggtgcg agaggccgag ggccagaaca acatccgcct accatccatc attgttataa     1740
aaaacttagg aaccaggtcc acacagccgc cagcccatca accatccact cccacgattg     1800
gagccaatgg cagaagagca ggcacgccat gtcaaaaacg gactgaaatg catccgggct     1860
ctcaaggccg agcccatcgg ctcactggcc atcgaggaag ctatggcagc atggtcagaa     1920
atatcagaca acccaggaca ggagcgagcc acctgcaggg aagagaaggc aggcagttcg     1980
ggtctcagca aaccatgcct ctcagcaatt ggatcaactg aaggcggtgc acctcgcatc     2040
cgcggtcagg gacctggaga gagcgatgac gacgctgaaa cttttgggaat ccccccaaga    2100 aatctccagg catcaagcac tgggttacag tgttattacg tttatgatca cagcggtgaa     2160
gcggttaagg gaatccaaga tgctgactct atcatggttc aatcaggcct tgatggtgat     2220
agcaccctct caggaggaga caatgaatct gaaaacagcg atgtggatat tggcgaacct     2280
gataccgagg gatatgctat cactgaccgg ggatctgctc ccatctctat ggggttcagg     2340
gcttctgatg ttgaaactgc agaaggaggg gagatccacg agctcctgag actccaatcc     2400
agaggcaaca actttccgaa gcttgggaaa actctcaatg ttcctccgcc cccggacccc     2460
ggtagggcca gcacttccgg gacacccatt aaaaagggca cagacgcgag attagcctca     2520
tttggaacgg agatcgcgtc tttattgaca ggtggtgcaa cccaatgtgc tcgaaagtca     2580
ccctcggaac catcagggcc aggtgcacct gcggggaatg tccccgagtg tgtgagcaat     2640
gccgcactga tacaggagtg gacacccgaa tctggtacca caatctcccc gagatcccag     2700
aataatgaag aagggggaga ctattatgat gatgagctgt tctctgatgt ccaagatatt     2760
aaaacagcct tggccaaaat acacgaggat aatcagaaga taatctccaa gctagaatca     2820
ctgctgttat tgaagggaga agttgagtca attaagaagc agatcaacag gcaaaatatc     2880
agcatatcca ccctgaagg acacctctca agcatcatga tcgccattcc tggacttggg     2940
aaggatccca acgacccac tgcagatgtc gaaatcaatc ccgacttgaa acccatcata     3000
ggcagagatt caggccgagc actggccgaa gttctcaaga aacccgttgc cagccgacaa     3060
ctccaaggaa tgacaaatgg acggaccagt tccagaggac agctgctgaa ggaatttcag     3120
```

```
ctaaagccga tcgggaaaaa gatgagctca gccgtcgggt tgttcctga caccggccct    3180 gcatcacgca gtgtaatccg ctccattata aaatccagcc ggctagagga ggatcggaag    3240
cgttacctga tgactctcct tgatgatatc aaaggagcca atgatcttgc caagttccac    3300
cagatgctga tgaagataat aatgaagtag ctacagctca acttacctgc caaccccatg    3360
ccagtcgacc caactagtac aacctaaatc cattataaaa aacttaggag caaagtgatt    3420
gcctcccaag gtccacaatg acagagacct acgacttcga caagtcggca tgggacatca    3480
aagggtcgat cgctccgata caacccacca cctacagtga tggcaggctg gtgccccagg    3540
tcagagtcat agatcctggt ctaggcgaca ggaaggatga atgctttatg tacatgtttc    3600 tgctggggt tgttgaggac agcgattccc tagggcctcc aatcgggcga gcatttgggt    3660
tcctgccctt aggtgttggc agatccacag caaagcccga aaaactcctc aaagaggcca    3720
ctgagcttga catagttgtt agacgtacag cagggctcaa tgaaaaactg gtgttctaca    3780
acaacacccc actaactctc ctcacacctt ggagaaaggt cctaacaaca gggagtgtct    3840
tcaacgcaaa ccaagtgtgc aatgcggtta atctgatacc gctcgatacc cgcagaggt    3900 tccgtgttgt ttatatgagc atcacccgtc tttcggataa cgggtattac accgttccta    3960
gaagaatgct ggaattcaga tcggtcaatg cagtggcctt caacctgctg gtgacccta    4020 ggattgacaa ggcgataggc cctgggaaga tcatcgacaa tacagagcaa cttcctgagg    4080
caacatttat ggtccacatc gggaacttca ggagaaagaa gagtgaagtc tactctgccg    4140
attattgcaa aatgaaaatc gaaaagatgg gcctggtttt tgcacttggt gggatagggg    4200
gcaccagtct tcacattaga agcacaggca aaatgagcaa gactctccat gcacaactcg    4260
ggttcaagaa gaccttatgt tacccgctga tggatatcaa tgaagacctt aatcgattac    4320
tctggaggag cagatgcaag atagtaagaa tccaggcagt tttgcagcca tcagttcctc    4380
aagaattccg catttacgac gacgtgatca taaatgatga ccaaggacta ttcaaagttc    4440
tgtagaccgt agtgcccagc aatgcccgaa acgaccccc ctcacaatga cagccagaag    4500
gcccggacaa aaaagccccc tccgaaagac tccacggacc aagcgagagg ccagccagca    4560
gccgacggca agcgcgaaca ccaggcggcc ccagcacaga acagccctga cacaaggcca    4620
ccaccagcca ccccaatctg catcctcctc gtgggacccc cgaggaccaa ccccaaggc    4680 tgcccccgat ccaaaccacc aaccgcatcc ccaccacccc cgggaaagaa accccagca    4740 attggaaggc ccctcccct cttcctcaac acaagaactc cacaaccgaa ccgcacaagc    4800
gaccgaggtg acccaaccgc aggcatccga ctccctagac agatcctctc tccccggcaa    4860
actaaacaaa acttagggcc aaggaacata cacacccaac agaacccaga ccccggccca    4920
cggcgccgcg cccccaaccc ccgacaacca gaggagcccc caaccaatc ccgccggctc    4980 ccccggtgcc cacaggcagg gacaccaacc cccgaacaga cccagcaccc aaccatcgac    5040
aatccaagac gggggggccc ccccaaaaaa aggcccccag gggccgacag ccagcaccgc    5100
gaggaagccc acccaccca cacacgacca cggcaaccaa accagaaccc agaccaccct    5160
gggccaccag ctcccagact cggccatcac cccgcagaaa ggaaaggcca caacccgcgc    5220
accccagccc cgatccggcg gggagccacc caacccgaac cagcacccaa gagcgatccc    5280
cgaaggaccc ccgaaccgca aaggacatca gtatcccaca gcctctccaa gtccccggt    5340 ctcctcctct tctcgaaggg accaaaagat caatccacca cacccgacga cactcaactc    5400 cccacccta aaggagacac cgggaatccc agaatcaaga ctcatccaat gtccatcatg    5460
ggtctcaagg tgaacgtctc tgccatattc atggcagtac tgttaactct ccaaacaccc    5520
```

```
accggtcaaa tccattgggg caatctctct aagatagggg tggtaggaat aggaagtgca    5580
agctacaaag ttatgactcg ttccagccat caatcattag tcataaaatt aatgcccaat    5640
ataactctcc tcaataactg cacgagggta gagattgcag aatacaggag actactgaga    5700
acagttttgg aaccaattag agatgcactt aatgcaatga cccagaatat aagaccggtt    5760
cagagtgtag cttcaagtag gagacacaag agatttgcgg gagtagtcct ggcaggtgcg    5820
gccctaggcg ttgccacagc tgctcagata acagccggac ttgcacttca ccagtccatg    5880
ctgaactctc aagccatcga caatctgaga gcgagcctgg aaactactaa tcaggcaatt    5940
gagacaatca gacaagcagg gcaggagatg atattggctg ttcagggtgt ccaagactac    6000
atcaataatg agctgatacc gtctatgaac caactatctt gtgatttaat cggccagaag    6060
ctcgggctca aattgctcag atactataca gaaatcctgt cattatttgg ccccagttta    6120
cgggacccca tatctgcgga gatatctatc caggctttga gctatgcgct tggaggagac    6180
atcaataagg tgttagaaaa gctcggatac agtggaggtg atttactggg catcttagag    6240
agcggaggaa taaaggcccg ataactcac gtcgacacag agtcctactt cattgtcctc    6300
agtatagcct atccgacgct gtccgagatt aaggggggtga ttgtccaccg gctagagggg    6360
gtctcgtaca acataggctc tcaagagtgg tataccactg tgcccaagta tgttgcaacc    6420
caagggtacc ttatctcgaa ttttgatgag tcatcgtgta cttcatgcc agaggggact    6480 gtgtgcagcc aaaatgcctt gtacccgatg agtcctctgc tccaagaatg cctccggggg    6540
tacaccaagt cctgtgctcg tacactcgta tccgggtctt ttgggaaccg gttcattta    6600 tcacaaggga acctaatagc caattgtgca tcaatccttt gcaagtgtta cacaacagga    6660
acgatcatta atcaagaccc tgacaagatc ctaacataca ttgctgccga tcactgcccg    6720
gtagtcgagg tgaacggcgt gaccatccaa gtcgggagca ggaggtatcc agacgctgtg    6780
tacttgcaca gaattgacct cggtcctccc atatcattgg agaggttgga cgtagggaca    6840
aatctgggga atgcaattgc taagttggag gatgccaagg aattgttgga gtcatcggac    6900
cagatattga ggagtatgaa aggtttatcg agcactagca tagtctacat cctgattgca    6960
gtgtgtcttg gagggttgat agggatcccc gctttaatat gttgctgcag ggggcgttgt    7020
aacaaaaagg gagaacaagt tggtatgtca agaccaggcc taaagcctga tcttacggga    7080
acatcaaaat cctatgtaag gtcgctctga tcctctacaa ctcttgaaac acaaatgtcc    7140
cacaagtctc ctcttcgtca tcaagcaacc accgcaccca gcatcaagcc cacctgaaat    7200
tatctccggc ttccctctgg ccgaacaata tcggtagtta atcaaaactt agggtgcaag    7260
atcatccaca atgtcaccac aacgagaccg gataaatgcc ttctacaaag ataaccccca    7320
tcccaaggga agtaggatag tcattaacag agaacatctt atgattgata gaccttatgt    7380
tttgctggct gttctgtttg tcatgttttct gagcttgatc gggttgctag ccattgcagg    7440
cattagactt catcgggcag ccatctacac cgcagagatc cataaagcc tcagcaccaa    7500 tctagatgta actaactcaa tcgagcatca ggtcaaggac gtgctgacac cactcttcaa    7560
aatcatcggt gatgaagtgg gcctgaggac acctcagaga ttcactgacc tagtgaaatt    7620
aatctctgac aagattaaat tccttaatcc ggataggag tacgacttca gagatctcac    7680
ttggtgtatc aacccgccag agagaatcaa attggattat gatcaatact gtgcagatgt    7740
ggctgctgaa gagctcatga atgcattggt gaactcaact ctactggaga ccagaacaac    7800
caatcagttc ctagctgtct caaagggaaa ctgctcaggg cccactacaa tcagaggtca    7860
```

```
attctcaaac atgtcgctgt ccctgttaga cttgtattta ggtcgaggtt acaatgtgtc    7920
atctatagtc actatgacat cccagggaat gtatggggga acttacctag tggaaaagcc    7980
taatctgagc agcaaaaggt cagagttgtc acaactgagc atgtaccgag tgtttgaagt    8040
aggtgttatc agaaatccgg gtttgggggc tccggtgttc catatgacaa actatcttga    8100
gcaaccagtc agtaatgatc tcagcaactg tatggtggct ttgggggagc tcaaactcgc    8160
agcccttcgt cacggggaag attctatcac aattccctat cagggatcag ggaaaggtgt    8220
cagcttccag ctcgtcaagc taggtgtctg gaaatcccca accgacatgc aatcctgggt    8280
ccccttatca acggatgatc cagtgataga caggctttac ctctcatctc acagaggtgt    8340
tatcgctgac aatcaagcaa atgggctgt cccgacaaca cgaacagatg acaagttgcg    8400
aatggagaca tgcttccaac aggcgtgtaa gggtaaaatc caagcactct gcgagaatcc    8460
cgagtgggca ccattgaagg ataacaggat tccttcatac ggggtcttgt ctgttgatct    8520
gagtctgaca gttgagctta aaatcaaaat tgcttcggga ttcgggccat tgatcacaca    8580
cggttcaggg atggacctat acaaatccaa ccacaacaat gtgtattggc tgactatccc    8640
gccaatgaag aacctagcct taggtgtaat caacacattg gagtggatac cgagattcaa    8700
ggttagtccc tacctcttca ctgtcccaat taaggaagca ggcgaagact gccatgcccc    8760
aacatacta cctgcggagg tggatggtga tgtcaaactc agttccaatc tggtgattct    8820
acctggtcaa gatctccaat atgttttggc aacctacgat acttccaggg ttgaacatgc    8880
tgtggtttat tacgtttaca gcccaagccg ctcatttct tactttatc cttttaggtt    8940
gcctataaag ggggtccca tcgaattaca agtggaatgc ttcacatggg accaaaaact    9000
ctggtgccgt cacttctgtg tgcttgcgga ctcagaatct ggtggacata tcactcactc    9060
tgggatggtg ggcatgggag tcagctgcac agtcaccccgg gaagatgaa ccaatcgcag    9120
atagggctgc tagtgaacca atcacatgat gtcacccaga catcaggcat acccactagt    9180
catccatcat tgttataaaa aacttaggaa ccaggtccac acagctcgag tcgcgcgtgc    9240
caccatggaa accccagcac agcttctctt cctcctgctg ctctggctcc cagataccac    9300
tggagagatt gtgctgacgc aatcccctgg gactctctcc cttccctg gcgaacgggc    9360
tacactgtcc tgcagagctt cacagagcgt tgggtccagc tatctcgcct ggtaccagca    9420
gaaaccaggc caagcaccac gcctgctcat ctatggtgcc tttagcagag ccactggcat    9480
acccgatagg ttcagcggct caggcagcgg tacagacttc acgctgacca ttagccggct    9540
ggaacccgag gatttcgcag tgtactattg ccagcagtat gggagctctc cgtggacatt    9600
tggccaaggg acaaaggtgg agattaagcg cggtggtggt ggatcaggtg gaggcggaag    9660
tggaggtggc ggatcccagg tacagctggt cgagtctggt ggcggcgtag tgcaacccgg    9720
aagaagtttg cgactgtcat gcgcagcttc tgggtttacc ttcagctcct atacaatgca    9780
ctgggtcagg caggctccag ggaaaggcct ggagtgggtc accttcatct cttacgacgg    9840
gaacaacaag tactacgcgg attcagtgaa aggacggttt accatctccc gcgacaattc    9900
caagaatacc ctgtatctcc agatgaacag cttgagagcc gaagataccg ccatctacta    9960
ctgtgccaga actggatggc ttgggccttt tgactactgg ggccagggta tctctggtgac   10020
tgttagttca gtcgacgagg ccaaatcttg tgacaaaact cacacatgcc caccgtgccc   10080
agcacccgaa ctcctggggg gaccgtcagt cttcctcttc ccccaaaac ccaaggacac    10140
cctcatgatc tcccggaccc ctgaggtcac atgcgtggtg gtggacgtga gccacgaaga   10200
ccctgaggtc aagttcaact ggtacgtgga cggcgtggag gtgcataatg ccaagacaaa   10260
```

```
gccgcgggag gagcagtaca acagcacgta ccgtgtggtc agcgtcctca ccgtcctgca    10320
ccaggactgg ctgaatggca aggagtacaa gtgcaaggtc tccaacaaag ccctcccagc    10380
ccccatcgag aaaaccatct ccaaagccaa ggggcagccc cgagaaccac aggtgtacac    10440
cctgccccca tcccgggatg agctgaccaa gaaccaggtc agcctgacct gcctggtcaa    10500
aggcttctat cccagcgaca tcgccgtgga gtgggagagc aatgggcagc cggagaacaa    10560
ctacaagacc acgcctcccg tgctggactc cgacggctcc ttcttcctct acagcaagct    10620
caccgtggac aagagcaggt ggcagcaggg gaacgtcttc tcatgctccg tgatgcatga    10680
ggctctgcac aaccactaca cgcagaagag cctctccctg tctccgggta agtcgacaa     10740 ttaggcgcgc gttctagtgt gaaatagaca tcagaattaa gaaaaacgta gggtccaagt    10800
ggttccccgt tatggactcg ctatctgtca accagatctt ataccctgaa gttcacctag    10860
atagcccgat agttaccaat aagatagtag ccatcctgga gtatgctcga gtccctcacg    10920
cttacagcct ggaggaccct acactgtgtc agaacatcaa gcaccgccta aaaaacggat    10980
tttccaacca aatgattata acaatgtgg aagttgggaa tgtcatcaag tccaagctta     11040
ggagttatcc ggcccactct catattccat atccaaattg taatcaggat ttatttaaca    11100
tagaagacaa agagtcaacg aggaagatcc gtgaactcct caaaaagggg aattcgctgt    11160
actccaaagt cagtgataag gttttccaat gcttaaggga cactaactca cggcttggcc    11220
taggctccga attgagggag gacatcaagg agaaagttat taacttggga gtttacatgc    11280
acagctccca gtggtttgag ccctttctgt tttggtttac agtcaagact gagatgaggt    11340
cagtgattaa atcacaaacc catacttgcc ataggaggag acacacacct gtattcttca    11400
ctggtagttc agttgagttg ctaatctctc gtgaccttgt tgctataatc agtaaagagt    11460
ctcaacatgt atattacctg acatttgaac tggttttgat gtattgtgat gtcatagagg    11520
ggaggttaat gacagagacc gctatgacta ttgatgctag gtatacagag cttctaggaa    11580
gagtcagata catgtggaaa ctgatagatg gtttcttccc tgcactcggg aatccaactt    11640
atcaaattgt agccatgctg gagcctcttt cacttgctta cctgcagctg agggatataa    11700
cagtagaact cagaggtgct ttccttaacc actgctttac tgaaatacat gatgttcttg    11760
accaaaacgg gttttctgat gaaggtactt atcatgagtt aactgaagct ctagattaca    11820
ttttcataac tgatgacata catctgacag gggagatttc tcattttttc agaagtttcg    11880
gccaccccag acttgaagca gtaacggctg ctgaaaatgt taggaaatac atgaatcagc    11940
ctaaagtcat tgtgtatgag actctgatga aggtcatgc catattttgt ggaatcataa     12000
tcaacggcta tcgtgacagg cacggaggca gttggccacc gctgaccctc ccctgcatg     12060 ctgcagacac aatccggaat gctcaagctt caggtgaagg gttaacacat gagcagtgcg    12120
ttgataactg gaaatctttt gctggagtga aatttggctg ctttatgcct cttagcctgg    12180
atagtgatct gacaatgtac ctaaaggaca aggcacttgc tgctctccaa agggaatggg    12240
attcagttta cccgaaagag ttcctgcgtt acgaccctcc caagggaacc gggtcacgga    12300
ggcttgtaga tgttttcctt aatgattcga gctttgaccc atatgatgtg ataatgtatg    12360
ttgtaagtgg agcttacctc catgaccctg agttcaacct gtcttacagc ctgaaagaaa    12420
aggagatcaa ggaaacaggt agacttttg ctaaaatgac ttacaaaatg agggcatgcc     12480
aagtgattgc tgaaaatcta atctcaaacg ggattggcaa atattttaag gacaatggga    12540
tggccaagga tgagcacgat ttgactaagg cactccacac tctagctgtc tcaggagtcc    12600
```

```
ccaaagatct caaagaaagt cacagggggg ggccagtctt aaaaacctac tcccgaagcc    12660
cagtccacac aagtaccagg aacgtgagag cagcaaaagg gtttataggg ttccctcaag    12720
taattcggca ggaccaagac actgatcatc cggagaatat ggaagcttac gagacagtca    12780
gtgcatttat cacgactgat ctcaagaagt actgccttaa ttggagatat gagaccatca    12840
gcttgtttgc acagaggcta aatgagattt acggattgcc ctcattttc cagtggctgc     12900 ataagaggct tgagacctct gtcctgtatg taagtgaccc tcattgcccc cccgaccttg    12960
acgcccatat cccgttatat aaagtcccca atgatcaaat cttcattaag taccctatgg    13020
gaggtataga agggtattgt cagaagctgt ggaccatcag caccattccc tatctatacc    13080
tggctgctta tgagagcgga gtaaggattg cttcgttagt gcaagggac aatcagacca      13140 tagccgtaac aaaaagggta cccagcacat ggccctacaa ccttaagaaa cgggaagctg    13200
ctagagtaac tagagattac tttgtaattc ttaggcaaag gctacatgat attggccatc    13260
acctcaaggc aaatgagaca attgtttcat cacattttt tgtctattca aaaggaatat     13320
attatgatgg gctacttgtg tcccaatcac tcaagagcat cgcaagatgt gtattctggt    13380
cagagactat agttgatgaa caagggcag catgcagtaa tattgctaca acaatggcta      13440
aaagcatcga gagaggttat gaccgttacc ttgcatattc cctgaacgtc ctaaaagtga    13500
tacagcaaat tctgatctct cttggcttca caatcaattc aaccatgacc cgggatgtag    13560
tcatacccct cctcacaaac aacgacctct taataaggat ggcactgttg cccgctccta    13620
ttggggggat gaattatctg aatatgagca ggctgtttgt cagaaacatc ggtgatccag    13680
taacatcatc aattgctgat ctcaagagaa tgattctcgc ctcactaatg cctgaagaga    13740
ccctccatca agtaatgaca caacaaccgg gggactcttc attcctagac tgggctagcg    13800
acccttactc agcaaatctt gtatgtgtcc agagcatcac tagactcctc aagaacataa    13860
ctgcaaggtt tgtcctgatc catagtccaa acccaatgtt aaaaggatta ttccatgatg    13920
acagtaaaga agaggacgag ggactggcgg cattcctcat ggacaggcat attatagtac    13980
ctagggcagc tcatgaaatc ctggatcata gtgtcacagg ggcaagagag tctattgcag    14040
gcatgctgga taccacaaaa ggcttgattc gagccagcat gaggaagggg gggttaacct    14100
ctcgagtgat aaccagattg tccaattatg actatgaaca attcagagca gggatggtgc    14160
tattgacagg aagaaagaga aatgtcctca ttgacaaaga gtcatgttca gtgcagctgg    14220
cgagagctct aagaagccat atgtgggcga ggctagctcg aggacggcct atttacggcc    14280
ttgaggtccc tgatgtacta gaatctatgc gaggccacct tattcggcgt catgagacat    14340
gtgtcatctg cgagtgtgga tcagtcaact acggatggtt ttttgtcccc tcgggttgcc    14400
aactggatga tattgacaag gaaacatcat ccttgagagt cccatatatt ggttctacca    14460
ctgatgagag aacagacatg aagcttgcct tcgtaagagc cccaagtcga tccttgcgat    14520
ctgctgttag aatagcaaca gtgtactcat gggcttacgg tgatgatgat agctcttgga    14580
acgaagcctg gttgttggct aggcaaaggg ccaatgtgag cctggaggag ctaagggtga    14640
tcactcccat ctcaacttcg actaatttag cgcataggtt gagggatcgt agcactcaag    14700
tgaaatactc aggtacatcc cttgtccgag tgcgaggta ccacaatc tccaacgaca       14760 atctctcatt tgtcatatca gataagaagg ttgatactaa ctttatatac caacaaggaa    14820
tgcttctagg gttgggtgtt ttagaaacat tgtttcgact cgagaaagat accggatcat    14880
ctaacacggt attacatctt cacgtcgaaa cagattgttg cgtgatcccg atgatagatc    14940
atcccaggat acccagctcc cgcaagctag agctgagggc agagctatgt accaacccat    15000
```

```
tgatatatga taatgcacct ttaattgaca gagatgcaac aaggctatac acccagagcc   15060
ataggaggca ccttgtggaa tttgttacat ggtccacacc ccaactatat cacattttag   15120
ctaagtccac agcactatct atgattgacc tggtaacaaa atttgagaag gaccatatga   15180
atgaaatttc agctctcata ggggatgacg atatcaatag tttcataact gagtttctgc   15240
tcatagagcc aagattattc actatctact tgggccagtg tgcggccatc aattgggcat   15300
ttgatgtaca ttatcataga ccatcaggga aatatcagat gggtgagctg ttgtcatcgt   15360
tcctttctag aatgagcaaa ggagtgttta aggtgcttgt caatgctcta agccacccaa   15420
agatctacaa gaaattctgg cattgtggta ttatagagcc tatccatggt ccttcacttg   15480
atgctcaaaa cttgcacaca actgtgtgca acatggttta cacatgctat atgacctacc   15540
tcgacctgtt gttgaatgaa gagttagaag agttcacatt tctcttgtgt gaaagcgacg   15600
aggatgtagt accggacaga ttcgacaaca tccaggcaaa acacttatgt gttctggcag   15660
atttgtactg tcaaccaggg acctgcccac caattcgagg tctaagaccg gtagagaaat   15720
gtgcagttct aaccgaccat atcaaggcag aggctatgtt atctccagca ggatcttcgt   15780
ggaacataaa tccaattatt gtagaccatt actcatgctc tctgacttat ctccggcgag   15840
gatcgatcaa acagataaga ttgagagttg atccaggatt cattttcgac gccctcgctg   15900
aggtaaatgt cagtcagcca aagatcggca gcaacaacat ctcaaatatg agcatcaagg   15960
ctttcagacc cccacacgat gatgttgcaa aattgctcaa agatatcaac acaagcaagc   16020
acaatcttcc catttcaggg ggcaatctcg ccaattatga aatccatgct ttccgcagaa   16080
tcgggttgaa ctcatctgct tgctacaaag ctgttgagat atcaacatta attaggagat   16140
gccttgagcc aggggaggac ggcttgttct tgggtgaggg atcgggttct atgttgatca   16200
cttataaaga gatacttaaa ctaaacaagt gcttctataa tagtggggtt tccgccaatt   16260
ctagatctgg tcaaagggaa ttagcaccct atccctccga agttggcctt gtcgaacaca   16320
gaatgggagt aggtaatatt gtcaaagtgc tctttaacgg gaggcccgaa gtcacgtggg   16380
taggcagtgt agattgcttc aatttcatag ttagtaatat ccctacctct agtgtggggt   16440
ttatccattc agatatagag accttgcctg acaaagatac tatagagaag ctagaggaat   16500
tggcagccat cttatcgatg gctctgctcc tgggcaaaat aggatcaata ctggtgatta   16560
agcttatgcc tttcagcggg gattttgttc agggattat aagttatgta gggtctcatt   16620
atagagaagt gaaccttgta taccctagat acagcaactt catctctact gaatcttatt   16680
tggttatgac agatctcaag gctaaccggc taatgaatcc tgaaaagatt aagcagcaga   16740
taattgaatc atctgtgagg acttcacctg gacttatagg tcacatccta tccattaagc   16800
aactaagctg catacaagca attgtgggag acgcagttag tagaggtgat atcaatccta   16860
ctctgaaaaa acttacacct atagagcagg tgctgatcaa ttgcgggttg gcaattaacg   16920
gacctaagct gtgcaaagaa ttgatccacc atgatgttgc ctcagggcaa gatggattgc   16980
ttaattctat actcatcctc tacagggagt tggcaagatt caaagacaac caaagaagtc   17040 aacagggat gttccacgct taccccgtat tggtaagtag caggcaacga gaacttatat   17100
ctaggatcac ccgcaaattc tggggcaca ttcttcttta ctccgggaac aaaaagttga   17160
taaataagtt tatccagaat ctcaagtccg gctatctgat actagactta caccagaata   17220
tcttcgttaa gaatctatcc aagtcagaga aacagattat tatgacgggg ggtttgaaac   17280
gtgagtgggt ttttaaggta acagtcaagg agaccaaaga atggtataag ttagtcggat   17340
```

| | |
|---|---|
| acagtgccct gattaaggac taattggttg aactccggaa ccctaatcct gccctaggtg | 17400 |
| gttaggcatt atttgcaata tattaaagaa aactttgaaa atacgaagtt tctattccca | 17460 |
| gctttgtctg gt | 17472 |

<210> SEQ ID NO 7
<211> LENGTH: 17484
<212> TYPE: DNA
<213> ORGANISM: Artificial
<220> FEATURE:
<223> OTHER INFORMATION: MeV Schwarz virus genome encoding downstream of H optimized cDNA for secretable (human) antibody anti-human PD-L1 WITHOUT tags, contains homologous secretion signal from human IgG variable kappa subgroup III, L6

<400> SEQUENCE: 7

| | |
|---|---|
| accaaacaaa gttgggtaag gatagttcaa tcaatgatca tcttctagtg cacttaggat | 60 |
| tcaagatcct attatcaggg acaagagcag gattagggat atccgagatg ccacacttt | 120 |
| taaggagctt agcattgttc aaaagaaaca aggacaaacc acccattaca tcaggatccg | 180 |
| gtggagccat cagaggaatc aaacacatta ttatagtacc aatccctgga gattcctcaa | 240 |
| ttaccactcg atccagactt ctggaccggt tggtgaggtt aattggaaac ccggatgtga | 300 |
| gcgggcccaa actaacaggg gcactaatag gtatattatc cttatttgtg gagtctccag | 360 |
| gtcaattgat tcagaggatc accgatgacc ctgacgttag cataaggctg ttagaggttg | 420 |
| tccagagtga ccagtcacaa tctggcctta ccttcgcatc aagaggtacc aacatggagg | 480 |
| atgaggcgga ccaatacttt tcacatgatg atccaattag tagtgatcaa tccaggttcg | 540 |
| gatggttcgg gaacaaggaa atctcagata ttgaagtgca agaccctgag ggattcaaca | 600 |
| tgattctggg taccatccta gcccaaattt gggtcttgct cgcaaaggcg gttacggccc | 660 |
| cagacacggc agctgattcg gagctaagaa ggtggataaa gtacacccaa caagaaggg | 720 |
| tagttggtga atttagattg gagagaaaat ggttggatgt ggtgaggaac aggattgccg | 780 |
| aggacctctc cttacgccga ttcatggtcg ctctaatcct ggatatcaag agaacacccg | 840 |
| gaaacaaacc caggattgct gaaatgatat gtgacattga tacatatatc gtagaggcag | 900 |
| gattagccag ttttatcctg actattaagt ttgggataga aactatgtat cctgctcttg | 960 |
| gactgcatga atttgctggt gagttatcca cacttgagtc cttgatgaac ctttaccagc | 1020 |
| aaaatgggga aactgcaccc tacatggtaa tcctggagaa ctcaattcag aacaagttca | 1080 |
| gtgcaggatc ataccctctg ctctggagct atgccatggg agtaggagtg aacttgaaa | 1140 |
| actccatggg aggtttgaac tttggccgat cttactttga tccagcatat tttagattag | 1200 |
| ggcaagagat ggtaaggagg tcagctggaa aggtcagttc acattggcat ctgaactcg | 1260 |
| gtatcactgc cgaggatgca aggcttgttt cagagattgc aatgcatact actgaggaca | 1320 |
| agatcagtag agcggttgga cccagacaag cccaagtatc atttctacac ggtgatcaaa | 1380 |
| gtgagaatga gctaccgaga ttgggggggca aggaagatag gagggtcaaa cagagtcgag | 1440 |
| gagaagccag ggagagctac agagaaaccg ggcccagcag agcaagtgat gcgagagctg | 1500 |
| cccatcttcc aaccggcaca cccctagaca ttgacactgc aacggagtcc agccaagatc | 1560 |
| cgcaggacag tcgaaggtca gctgacgccc tgcttaggct gcaagccatg caggaatct | 1620 |
| cggaagaaca aggctcagac acggacaccc ctatagtgta caatgacaga aatcttctag | 1680 |
| actaggtgcg agaggccgag ggccagaaca acatccgcct accatccatc attgttataa | 1740 |
| aaaacttagg aaccaggtcc acacagccgc cagcccatca accatccact cccacgattg | 1800 |

```
gagccaatgg cagaagagca ggcacgccat gtcaaaaacg gactggaatg catccgggct   1860
ctcaaggccg agcccatcgg ctcactggcc atcgaggaag ctatggcagc atggtcagaa   1920
atatcagaca acccaggaca ggagcgagcc acctgcaggg aagagaaggc aggcagttcg   1980
ggtctcagca aaccatgcct ctcagcaatt ggatcaactg aaggcggtgc acctcgcatc   2040
cgcggtcagg gacctggaga gagcgatgac gacgctgaaa ctttgggaat ccccccaaga   2100
aatctccagg catcaagcac tgggttacag tgttattacg tttatgatca cagcggtgaa   2160
gcggttaagg gaatccaaga tgctgactct atcatggttc aatcaggcct tgatggtgat   2220
agcaccctct caggaggaga caatgaatct gaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
agaggcaaca actttccgaa gcttgggaaa actctcaatg ttcctccgcc cccggacccc   2460
ggtagggcca gcacttccgg gacacccatt aaaaagggca cagacgcgag attagcctca   2520
tttggaacgg agatcgcgtc tttattgaca ggtggtgcaa cccaatgtgc tcgaaagtca   2580
ccctcggaac catcagggcc aggtgcacct gcggggaatg tccccgagtg tgtgagcaat   2640
gccgcactga tacaggagtg gacacccgaa tctggtacca caatctcccc gagatcccag   2700
aataatgaag aagggggaga ctattatgat gatgagctgt tctctgatgt ccaagatatt   2760
aaaacagcct tggccaaaat acacgaggat aatcagaaga taatctccaa gctagaatca   2820
ctgctgttat tgaagggaga agttgagtca attaagaagc agatcaacag gcaaaatatc   2880
agcatatcca ccctgaagg cacctctca agcatcatga tcgccattcc tggacttggg   2940
aaggatccca acgaccccac tgcagatgtc gaaatcaatc ccgacttgaa acccatcata   3000
ggcagagatt caggccgagc actggccgaa gttctcaaga acccgttgc cagccgacaa   3060 ctccaaggaa tgacaaatgg acggaccagt tccagaggac agctgctgaa ggaatttcag   3120
ctaaagccga tcgggaaaaa gatgagctca gccgtcgggt tgttcctga caccggccct   3180 gcatcacgca gtgtaatccg ctccattata aaatccagcc ggctagagga ggatcggaag   3240
cgttacctga tgactctcct tgatgatatc aaaggagcca atgatcttgc caagttccac   3300
cagatgctga tgaagataat aatgaagtag ctacagctca acttacctgc caaccccatg   3360
ccagtcgacc caactagtac aacctaaatc cattataaaa aacttaggag caaagtgatt   3420
gcctcccaag gtccacaatg acagagacct acgacttcga caagtcggca tgggacatca   3480
aagggtcgat cgctccgata caacccacca cctacagtga tggcaggctg gtgccccagg   3540
tcagagtcat agatcctggt ctaggcgaca ggaaggatga atgctttatg tacatgtttc   3600
tgctgggggt tgttgaggac agcgattccc tagggcctcc aatcgggcga gcatttgggt   3660
tcctgccctt aggtgttggc agatccacag caaagcccga aaaactcctc aaagaggcca   3720
ctgagcttga catagttgtt agacgtacag cagggctcaa tgaaaaactg tgttctaca   3780 acaacacccc actaactctc ctcacacctt ggagaaaggt cctaacaaca gggagtgtct   3840
tcaacgcaaa ccaagtgtgc aatgcggtta atctgatacc gctcgatacc ccgcagaggt   3900
tccgtgttgt ttatatgagc atcacccgtc tttcggataa cggtattac accgttccta   3960 gaagaatgct ggaattcaga tcggtcaatg cagtggcctt caacctgctg gtgacccta   4020 ggattgacaa ggcgataggc cctgggaaga tcatcgacaa tacagagcaa cttcctgagg   4080
caaacattat ggtccacatc gggaacttca ggagaaagaa gagtgaagtc tactctgccg   4140
attattgcaa aatgaaaatc gaaagatgg gcctggtttt tgcacttggt gggataggg   4200
```

```
gcaccagtct tcacattaga agcacaggca aaatgagcaa gactctccat gcacaactcg    4260
ggttcaagaa gaccttatgt tacccgctga tggatatcaa tgaagacctt aatcgattac    4320
tctggaggag cagatgcaag atagtaagaa tccaggcagt tttgcagcca tcagttcctc    4380
aagaattccg catttacgac gacgtgatca taaatgatga ccaaggacta ttcaaagttc    4440
tgtagaccgt agtgcccagc aatgcccgaa acgaccccc ctcacaatga cagccagaag    4500
gcccggacaa aaaagccccc tccgaaagac tccacggacc aagcgagagg ccagccagca    4560
gccgacggca agcgcgaaca ccaggcggcc ccagcacaga acagccctga cacaaggcca    4620
ccaccagcca ccccaatctg catcctcctc gtgggacccc cgaggaccaa cccccaaggc    4680
tgcccccgat ccaaaccacc aaccgcatcc ccaccacccc cgggaaagaa accccccagca    4740 attggaaggc ccctcccct cttcctcaac acaagaactc cacaaccgaa ccgcacaagc    4800
gaccgaggtg acccaaccgc aggcatccga ctccctagac agatcctctc tccccggcaa    4860
actaaacaaa acttagggcc aaggaacata cacacccaac agaacccaga ccccggccca    4920
cggcgccgcg cccccaaccc ccgacaacca gagggagccc ccaaccaatc ccgccggctc    4980
ccccggtgcc cacaggcagg gacaccaacc cccgaacaga cccagcaccc aaccatcgac    5040
aatccaagac gggggggccc cccaaaaaa aggcccccag gggccgacag ccagcaccgc    5100
gaggaagccc acccacccca cacgaccaa cggcaaccaa accagaaccc agaccaccct    5160
gggccaccag ctcccagact cggccatcac cccgcagaaa ggaaaggcca caacccgcgc    5220
accccagccc cgatccggcg gggagccacc caacccgaac cagcacccaa gagcgatccc    5280
cgaaggaccc ccgaaccgca aaggacatca gtatcccaca gcctctccaa gtccccccggt   5340 ctcctcctct tctcgaaggg accaaaagat caatccacca cacccgacga cactcaactc    5400
cccaccccta aaggagacac cgggaatccc agaatcaaga ctcatccaat gtccatcatg    5460
ggtctcaagg tgaacgtctc tgccatattc atggcagtac tgttaactct ccaaacaccc    5520
accggtcaaa tccattgggg caatctctct aagataggg tggtaggaat aggaagtgca    5580
agctacaaag ttatgactcg ttccagccat caatcattag tcataaaatt aatgcccaat    5640
ataactctcc tcaataactg cacgagggta gagattgcag aatacaggag actactgaga    5700
acagttttgg aaccaattag agatgcactt aatgcaatga cccagaatat aagaccggtt    5760
cagagtgtag cttcaagtag gagacacaag agatttgcgg gagtagtcct ggcaggtgcg    5820
gccctaggcg ttgccacagc tgctcagata acagccggca ttgcacttca ccagtccatg    5880
ctgaactctc aagccatcga caatctgaga gcgagcctgg aaactactaa tcaggcaatt    5940
gagacaatca gacaagcagg gcaggagatg atattggctg ttcagggtgt ccaagactac    6000
atcaataatg agctgatacc gtctatgaac caactatctt gtgatttaat cggccagaag    6060
ctcgggctca aattgctcag atactataca gaaatcctgt cattatttgg ccccagttta    6120
cgggacccca tatctgcgga gatatctatc caggctttga gctatgcgct tggaggagac    6180
atcaataagg tgttagaaaa gctcggatac agtggaggtg atttactggg catcttagag    6240 agcgaggaa taaaggcccg gataactcac gtcgacacag agtcctactt cattgtcctc    6300
agtatagcct atcgacgct gtccgagatt aaggggtga ttgtccaccg gctagagggg    6360
gtctcgtaca acataggctc tcaagagtgg tataccactg tgcccaagta tgttgcaacc    6420
caagggtacc ttatctcgaa ttttgatgag tcatcgtgta ctttcatgcc agaggggact    6480
gtgtgcagcc aaaatgcctt gtacccgatg agtcctctgc tccaagaatg cctccggggg    6540
```

```
tacaccaagt cctgtgctcg tacactcgta tccgggtctt ttgggaaccg gttcatttta    6600
tcacaaggga acctaatagc caattgtgca tcaatccttt gcaagtgtta cacaacagga    6660
acgatcatta atcaagaccc tgacaagatc ctaacataca ttgctgccga tcactgcccg    6720
gtagtcgagg tgaacggcgt gaccatccaa gtcgggagca ggaggtatcc agacgctgtg    6780
tacttgcaca gaattgacct cggtcctccc atatcattgg agaggttgga cgtagggaca    6840
aatctgggga atgcaattgc taagttggag gatgccaagg aattgttgga gtcatcggac    6900
cagatattga ggagtatgaa aggtttatcg agcactagca tagtctacat cctgattgca    6960
gtgtgtcttg gagggttgat agggatcccc gctttaatat gttgctgcag ggggcgttgt    7020
aacaaaaagg gagaacaagt tggtatgtca agaccaggcc taaagcctga tcttacggga    7080
acatcaaaat cctatgtaag gtcgctctga tcctctacaa ctcttgaaac acaaatgtcc    7140
cacaagtctc ctcttcgtca tcaagcaacc accgcaccca gcatcaagcc cacctgaaat    7200
tatctccggc ttccctctgg ccgaacaata tcggtagtta atcaaaactt agggtgcaag    7260
atcatccaca atgtcaccac aacgagaccg gataaatgcc ttctacaaag ataaccccca    7320
tcccaaggga agtaggatag tcattaacag agaacatctt atgattgata gaccttatgt    7380
tttgctggct gttctgtttg tcatgtttct gagcttgatc gggttgctag ccattgcagg    7440
cattagactt catcgggcag ccatctacac cgcagagatc cataaaagcc tcagcaccaa    7500
tctagatgta actaactcaa tcgagcatca ggtcaaggac gtgctgacac cactcttcaa    7560
aatcatcggt gatgaagtgg gcctgaggac acctcagaga ttcactgacc tagtgaaatt    7620
aatctctgac aagattaaat tccttaatcc ggatagggag tacgacttca gagatctcac    7680
ttggtgtatc aacccgccag agagaatcaa attggattat gatcaatact gtgcagatgt    7740
ggctgctgaa gagctcatga atgcattggt gaactcaact ctactggaga ccagaacaac    7800
caatcagttc ctagctgtct caaagggaaa ctgctcaggg cccactacaa tcagaggtca    7860
attctcaaac atgtcgctgt ccctgttaga cttgtattta ggtcgaggtt acaatgtgtc    7920
atctatagtc actatgacat cccagggaat gtatggggga acttacctag tggaaaagcc    7980
taatctgagc agcaaaaggt cagagttgtc acaactgagc atgtaccgag tgtttgaagt    8040
aggtgttatc agaaatccgg gtttgggggc tccggtgttc catatgacaa actatcttga    8100
gcaaccagtc agtaatgatc tcagcaactg tatggtggct ttgggggagc tcaaactcgc    8160
agccctttgt cacggggaag attctatcac aattccctat cagggatcag ggaaaggtgt    8220
cagcttccag ctcgtcaagc taggtgtctg gaaatcccca accgacatgc aatcctgggt    8280
ccccttatca acgatgatc cagtgataga caggctttac ctctcatctc acaggagtgt    8340
tatcgctgac aatcaagcaa aatgggctgt cccgacaaca cgaacagatg acaagttgcg    8400
aatggagaca tgcttccaac aggcgtgtaa gggtaaaatc caagcactct gcgagaatcc    8460
cgagtgggca ccattgaagg ataacaggat tccttcatac ggggtcttgt ctgttgatct    8520
gagtctgaca gttgagctta aaatcaaaat tgcttcggga ttcgggccat tgatcacaca    8580
cggttcaggg atggacctat acaaatccaa ccacaacaat gtgtattggc tgactatccc    8640
gccaatgaag aacctagcct taggtgtaat caacacattg gagtggatac cgagattcaa    8700
ggttagtccc tacctcttca ctgtcccaat taaggaagca ggcgaagact gccatgcccc    8760
aacataccta cctgcggagg tggatggtga tgtcaaactc agttccaatc tggtgattct    8820
acctggtcaa gatctccaat atgttttggc aacctacgat acttccaggg ttgaacatgc    8880 tgtggttat tacgtttaca gcccaagccg ctcatttttct tactttatc ctttaggtt    8940
```

```
gcctataaag ggggtcccca tcgaattaca agtggaatgc ttcacatggg accaaaaact    9000
ctggtgccgt cacttctgtg tgcttgcgga ctcagaatct ggtggacata tcactcactc    9060
tgggatggtg ggcatgggag tcagctgcac agtcacccgg aagatggaa ccaatcgcag     9120 atagggctgc tagtgaacca atcacatgat gtcacccaga catcaggcat acccactagt    9180
catccatcat tgttataaaa aacttaggaa ccaggtccac acagctcgag tcgcgcgtgc    9240
caccatggaa accccagcac agcttctctt cctcctgctg ctctggctcc cagataccac    9300
tggagagatt gtcctgacac agagcccagc tacactttcc ctgtctccgg gcgaaagagc    9360
aaccctctct tgcagggcta gccagtctgt cagctcttat ctcgcctggt atcagcagaa    9420
accaggccag gctcccagac tgctgatcta cgacgctagc aatcgcgcca ctggcatacc    9480
agcacgcttt tcagggtccg gcagtggtac cgacttcacc ctgaccatct cctcactgga    9540
acctgaggac tttgccgtgt attactgtca acagcggagt aactggccca cctttgggca    9600
gggcactaag gtggagatca aacgcggtgg tggtggatca ggtggaggcg aagtggagg     9660 tggcggatcc caggtgcaac tggtacagag cggcgcagaa gtgaagaaac ccgggtcctc    9720
agtgaaggtc agttgcaaga catccgggga caccttctca acgtatgcca ttagctgggt    9780
tagacaggct cctggtcaag gcttgagtg atgggaggt atcattccca tattcgggaa      9840
agcgcattat gcccagaagt tccaaggcag ggtcaccatc actgccgatg aatccacaag    9900
tactgcctac atggagttga gctccttgcg tagcgaggat actgcggtgt acttttgtgc    9960
acggaagttt cacttcgttt cagggagccc tttcgggatg gatgtttggg gacagggtac   10020
aacggtgaca gtatccagcg tcgacgaggc caaatcttgt gacaaaactc acacatgccc   10080
accgtgccca gcaccgaac tcctgggggg accgtcagtc ttcctcttcc ccccaaaacc     10140
caaggacacc ctcatgatct cccggacccc tgaggtcaca tgcgtggtgg tggacgtgag   10200
ccacgaagac cctgaggtca agttcaactg gtacgtggac ggcgtggagg tgcataatgc   10260
caagacaaag ccgcgggagg agcagtacaa cagcacgtac cgtgtggtca gcgtcctcac   10320
cgtcctgcac caggactggc tgaatggcaa ggagtacaag tgcaaggtct ccaacaaagc   10380
cctcccagcc cccatcgaga aaaccatctc caaagccaag gggcagcccc gagaaccaca   10440
ggtgtacacc ctgcccccat cccgggatga gctgaccaag aaccaggtca gcctgacctg   10500
cctggtcaaa ggcttctatc ccagcgacat cgccgtggag tgggagagca atgggcagcc   10560
ggagaacaac tacaagacca cgcctcccgt gctggactcc gacggctcct tcttcctcta   10620
cagcaagctc accgtggaca agagcaggtg gcagcagggg aacgtcttct catgctccgt   10680
gatgcatgag gctctgcaca accactacac gcagaagagc ctctccctgt ctccgggtaa   10740
agtcgacaat taataggcgc gcgttctagt gtgaaataga catcagaatt aagaaaaacg   10800
tagggtccaa gtggttcccc gttatggact cgctatctgt caaccagatc ttataccctg   10860
aagttcacct agatagcccg atagttacca ataagatagt agccatcctg gagtatgctc   10920
gagtccctca cgcttacagc ctggaggacc ctacactgtg tcagaacatc aagcaccgcc   10980
taaaaaacgg attttccaac caaatgatta taaacaatgt ggaagttggg aatgtcatca   11040
agtccaagct taggagttat ccggcccact ctcatattcc atatccaaat tgtaatcagg   11100
atttatttaa catagaagac aaagagtcaa cgaggaagat ccgtgaactc ctcaaaaagg   11160
ggaattcgct gtactccaaa gtcagtgata aggttttcca atgcttaagg gacactaact   11220
cacggcttgg cctaggctcc gaattgaggg aggacatcaa ggagaaagtt attaacttgg   11280
```

```
gagtttacat gcacagctcc cagtggtttg agccctttct gttttggttt acagtcaaga   11340
ctgagatgag gtcagtgatt aaatcacaaa cccatacttg cataggagg agacacacac    11400 ctgtattctt cactggtagt tcagttgagt tgctaatctc tcgtgacctt gttgctataa   11460
tcagtaaaga gtctcaacat gtatattacc tgacatttga actggttttg atgtattgtg   11520
atgtcataga ggggaggtta atgacagaga ccgctatgac tattgatgct aggtatacag   11580
agcttctagg aagagtcaga tacatgtgga aactgataga tggtttcttc cctgcactcg   11640
ggaatccaac ttatcaaatt gtagccatgc tggagcctct ttcacttgct tacctgcagc   11700
tgagggatat aacagtagaa ctcagaggtg ctttccttaa ccactgcttt actgaaatac   11760
atgatgttct tgaccaaaac gggttttctg atgaaggtac ttatcatgag ttaactgaag   11820
ctctagatta cattttcata actgatgaca tacatctgac aggggagatt ttctcatttt   11880
tcagaagttt cggccacccc agacttgaag cagtaacggc tgctgaaaat gttaggaaat   11940
acatgaatca gcctaaagtc attgtgtatg agactctgat gaaaggtcat gccatatttt   12000
gtggaatcat aatcaacggc tatcgtgaca ggcacggagg cagttggcca ccgctgaccc   12060 tcccctgca tgctgcagac acaatccgga atgctcaagc ttcaggtgaa gggttaacac    12120
atgagcagtg cgttgataac tggaaatctt ttgctggagt gaaatttggc tgctttatgc   12180
ctcttagcct ggatagtgat ctgacaatgt acctaaagga caaggcactt gctgctctcc   12240
aaagggaatg ggattcagtt tacccgaaag agttcctgcg ttacgaccct cccaagggaa   12300
ccgggtcacg gaggcttgta gatgttttcc ttaatgattc gagctttgac ccatatgatg   12360
tgataatgta tgttgtaagt ggagcttacc tccatgaccc tgagttcaac ctgtcttaca   12420
gcctgaaaga aaaggagatc aaggaaacag gtagacttt tgctaaaatg acttacaaaa    12480
tgagggcatg ccaagtgatt gctgaaaatc taatctcaaa cgggattggc aaatatttta   12540
aggacaatgg gatggccaag gatgagcacg atttgactaa ggcactccac actctagctg   12600
tctcaggagt ccccaaagat ctcaaagaaa gtcacagggg ggggccagtc ttaaaaacct   12660
actcccgaag cccagtccac acaagtacca ggaacgtgag agcagcaaaa gggtttatag   12720
ggttccctca gtaattcgg caggaccaag acactgatca tccggagaat atggaagctt    12780
acgagacagt cagtgcattt atcacgactg atctcaagaa gtactgcctt aattggagat   12840
atgagaccat cagcttgttt gcacagaggc taaatgagat ttacggattg ccctcatttt   12900
tccagtggct gcataagagg cttgagacct ctgtcctgta tgtaagtgac cctcattgcc   12960
cccccgacct tgacgcccat atcccgttat ataaagtccc caatgatcaa atcttcatta   13020
agtaccctat gggaggtata aagggtatt gtcagaagct gtggaccatc agcaccattc    13080
cctatctata cctggctgct tatgagagcg gagtaaggat tgcttcgtta gtgcaagggg   13140
acaatcagac catagccgta acaaaaaggg tacccagcac atggcccta aaccttaaga    13200 aacgggaagc tgctagagta actagagatt actttgtaat tcttaggcaa aggctacatg   13260
atattggcca tcacctcaag gcaaatgaga caattgtttc atcacatttt tttgtctatt   13320
caaaaggaat atattatgat gggctacttg tgtcccaatc actcaagagc atcgcaagat   13380
gtgtattctg gtcagagact atagttgatg aaacaagggc agcatgcagt aatattgcta   13440
caacaatggc taaaagcatc gagagaggtt atgaccgtta ccttgcatat ccctgaacg    13500 tcctaaaagt gatacagcaa attctgatct ctcttggctt cacaatcaat tcaaccatga   13560
cccgggatgt agtcataccc ctcctcacaa acaacgacct cttaataagg atggcactgt   13620
tgcccgctcc tattgggggg atgaattatc tgaatatgag caggctgttt gtcagaaaca   13680
```

```
tcggtgatcc agtaacatca tcaattgctg atctcaagag aatgattctc gcctcactaa   13740
tgcctgaaga gaccctccat caagtaatga cacaacaacc gggggactct tcattcctag   13800
actgggctag cgaccccttac tcagcaaatc ttgtatgtgt ccagagcatc actagactcc   13860
tcaagaacat aactgcaagg tttgtcctga tccatagtcc aaacccaatg ttaaaaggat   13920
tattccatga tgacagtaaa gaagaggacg agggactggc ggcattcctc atggacaggc   13980
atattatagt acctagggca gctcatgaaa tcctggatca tagtgtcaca ggggcaagag   14040
agtctattgc aggcatgctg gataccacaa aaggcttgat tcgagccagc atgaggaagg   14100
gggggttaac ctctcgagtg ataaccagat tgtccaatta tgactatgaa caattcagag   14160
cagggatggt gctattgaca ggaagaaaga gaaatgtcct cattgacaaa gagtcatgtt   14220
cagtgcagct ggcgagagct ctaagaagcc atatgtgggc gaggctagct cgaggacggc   14280
ctatttacgg ccttgaggtc cctgatgtac tagaatctat gcgaggccac cttattcggc   14340
gtcatgagac atgtgtcatc tgcgagtgtg gatcagtcaa ctacgatgg ttttttgtcc    14400 cctcgggttg ccaactggat gatattgaca aggaaacatc atccttgaga gtcccatata   14460
ttggttctac cactgatgag agaacagaca tgaagcttgc cttcgtaaga gccccaagtc   14520
gatccttgcg atctgctgtt agaatagcaa cagtgtactc atgggcttac ggtgatgatg   14580
atagctcttg gaacgaagcc tggttgttgg ctaggcaaag ggccaatgtg agcctggagg   14640
agctaagggt gatcactccc atctcaactt cgactaattt agcgcatagg ttgagggatc   14700
gtagcactca agtgaaatac tcaggtacat cccttgtccg agtggcgagg tataccacaa   14760
tctccaacga caatctctca tttgtcatat cagataagaa ggttgatact aactttatat   14820
accaacaagg aatgcttcta gggttgggtg ttttagaaac attgtttcga ctcgagaaag   14880
ataccggatc atctaacacg gtattacatc ttcacgtcga aacagattgt tgcgtgatcc   14940
cgatgataga tcatcccagg atacccagct cccgcaagct agagctgagg gcagagctat   15000
gtaccaaccc attgatatat gataatgcac ctttaattga cagagatgca acaaggctat   15060
acacccagag ccataggagg caccttgtgg aatttgttac atggtccaca ccccaactat   15120
atcacatttt agctaagtcc acagcactat ctatgattga cctggtaaca aaatttgaga   15180
aggaccatat gaatgaaatt tcagctctca tagggggatga cgatatcaat agtttcataa   15240
ctgagtttct gctcatagag ccaagattat tcactatcta cttgggccag tgtgcggcca   15300
tcaattgggc atttgatgta cattatcata gaccatcagg gaaatatcag atgggtgagc   15360
tgttgtcatc gttcctttct agaatgagca aaggagtgtt taaggtgctt gtcaatgctc   15420
taagccaccc aaagatctac aagaaattct ggcattgtgg tattatagag cctatccatg   15480
gtccttcact tgatgctcaa aacttgcaca caactgtgtg caacatggtt tacacatgct   15540
atatgaccta cctcgacctg ttgttgaatg aagagttaga agagttcaca tttctcttgt   15600
gtgaaagcga cgaggatgta gtaccggaca gattcgacaa catccaggca aaacactat    15660 gtgttctggc agatttgtac tgtcaaccag ggacctgccc accaattcga ggtctaagac   15720
cggtagagaa atgtgcagtt ctaaccgacc atatcaaggc agaggctatg ttatctccag   15780
caggatcttc gtggaacata aatccaatta ttgtagacca ttactcatgc tctctgactt   15840
atctccggcg aggatcgatc aaacagataa gattgagagt tgatccagga ttcatttttcg   15900 acgccctcgc tgaggtaaat gtcagtcagc caaagatcgg cagcaacaac atctcaaata   15960
tgagcatcaa ggctttcaga ccccccacacg atgatgttgc aaaattgctc aaagatatca   16020
```

| | |
|---|---:|
| acacaagcaa gcacaatctt cccatttcag ggggcaatct cgccaattat gaaatccatg | 16080 |
| ctttccgcag aatcgggttg aactcatctg cttgctacaa agctgttgag atatcaacat | 16140 |
| taattaggag atgccttgag ccaggggagg acggcttgtt cttgggtgag ggatcgggtt | 16200 |
| ctatgttgat cacttataaa gagatactta aactaaacaa gtgcttctat aatagtgggg | 16260 |
| tttccgccaa ttctagatct ggtcaaaggg aattagcacc ctatccctcc gaagttggcc | 16320 |
| ttgtcgaaca cagaatggga gtaggtaata ttgtcaaagt gctctttaac gggaggcccg | 16380 |
| aagtcacgtg ggtaggcagt gtagattgct tcaatttcat agttagtaat atccctacct | 16440 |
| ctagtgtggg gtttatccat tcagatatag agaccttgcc tgacaaagat actatagaga | 16500 |
| agctagagga attggcagcc atcttatcga tggctctgct cctgggcaaa ataggatcaa | 16560 |
| tactggtgat taagcttatg cctttcagcg gggattttgt tcagggattt ataagttatg | 16620 |
| tagggtctca ttatagagaa gtgaaccttg tataccctag atacagcaac ttcatctcta | 16680 |
| ctgaatctta tttggttatg acagatctca aggctaaccg gctaatgaat cctgaaaaga | 16740 |
| ttaagcagca gataattgaa tcatctgtga ggacttcacc tggacttata ggtcacatcc | 16800 |
| tatccattaa gcaactaagc tgcatacaag caattgtggg agacgcagtt agtagaggtg | 16860 |
| atatcaatcc tactctgaaa aaacttacac ctatagagca ggtgctgatc aattgcgggt | 16920 |
| tggcaattaa cggacctaag ctgtgcaaag aattgatcca ccatgatgtt gcctcagggc | 16980 |
| aagatggatt gcttaattct atactcatcc tctacaggga gttggcaaga ttcaaagaca | 17040 |
| accaaagaag tcaacaaggg atgttccacg cttaccccgt attggtaagt agcaggcaac | 17100 |
| gagaacttat atctaggatc acccgcaaat tctgggggca cattcttctt tactccggga | 17160 |
| acaaaaagtt gataaataag tttatccaga atctcaagtc cggctatctg atactagact | 17220 |
| tacaccagaa tatcttcgtt aagaatctat ccaagtcaga gaaacagatt attatgacgg | 17280 |
| ggggtttgaa acgtgagtgg gttttttaagg taacagtcaa ggagaccaaa gaatggtata | 17340 |
| agttagtcgg atacagtgcc ctgattaagg actaattggt tgaactccgg aaccctaatc | 17400 |
| ctgccctagg tggttaggca ttatttgcaa tatattaaag aaaactttga aaatacgaag | 17460 |
| tttctattcc cagctttgtc tggt | 17484 |

<210> SEQ ID NO 8
<211> LENGTH: 18006
<212> TYPE: DNA
<213> ORGANISM: Artificial
<220> FEATURE:
<223> OTHER INFORMATION: MeV Schwarz virus genome encoding cDNA for
      human GM-CSF and encoding cDNA for secretable (human) antibody
      anti-human CTLA-4

<400> SEQUENCE: 8

| | |
|---|---:|
| accaaacaaa gttgggtaag gatagttcaa tcaatgatca tcttctagtg cacttaggat | 60 |
| tcaagatcct attatcaggg acaagagcag gattagggat atctcgaggc gcgtgccacc | 120 |
| atgtggctcc agtctctgct gcttctggga acagttgcct gcagcattag tgccccagct | 180 |
| cgttctccct caccaagcac acaaccctgg gaacacgtca atgccataca ggaggcacga | 240 |
| aggctgctca atctgtcacg ggatactgcc gctgagatga acgagacagt ggaggtgatt | 300 |
| agcgagatgt tcgatctcca ggagcctact tgcctgcaaa ctcgccttga gctgtacaaa | 360 |
| cagggcttga gaggttccct taccaagctg aaagggcctt tgacgatgat ggcgagtcac | 420 |
| tataagcagc attgtccacc cacacccgaa acctcctgtg caaccagat catcaccttc | 480 |
| gaatccttca aagagaacct gaaggacttt ctgctcgtaa tcccgtttga ctgctgggaa | 540 |

```
cctgtgcagg aatgataggc gcgccatcca tcattgttat aaaaaactta ggattcaaga    600
tcctattatc agggacaaga gcaggattag ggatatccga gatggccaca cttttaagga    660
gcttagcatt gttcaaaaga aacaaggaca aaccacccat tacatcagga tccggtggag    720
ccatcagagg aatcaaacac attattatag taccaatccc tggagattcc tcaattacca    780
ctcgatccag acttctggac cggttggtga ggttaattgg aaacccggat gtgagcgggc    840
ccaaactaac aggggcacta ataggtatat tatccttatt tgtggagtct ccaggtcaat    900
tgattcagag gatcaccgat gaccctgacg ttagcataag gctgttagag gttgtccaga    960
gtgaccagtc acaatctggc cttaccttcg catcaagagg taccaacatg gaggatgagg   1020
cggaccaata cttttcacat gatgatccaa ttagtagtga tcaatccagg ttcggatggt   1080 tcggaacaa ggaaatctca gatattgaag tgcaagaccc tgagggattc aacatgattc   1140
tgggtaccat cctagcccaa atttgggtct tgctcgcaaa ggcggttacg gccccagaca   1200
cggcagctga ttcggagcta agaaggtgga taaagtacac ccaacaaaga agggtagttg   1260
gtgaatttag attggagaga aaatggttgg atgtggtgag gaacaggatt gccgaggacc   1320
tctccttacg ccgattcatg gtcgctctaa tcctggatat caagagaaca cccgaaaaca   1380
aacccaggat tgctgaaatg atatgtgaca ttgatacata tatcgtagag gcaggattag   1440
ccagttttat cctgactatt aagtttggga tagaaactat gtatcctgct cttgactgc    1500 atgaatttgc tggtgagtta tccacacttg agtccttgat gaacctttac cagcaaatgg   1560
gggaaactgc accctacatg gtaatcctgg agaactcaat tcagaacaag ttcagtgcag   1620
gatcataccc tctgctctgg agctatgcca tgggagtagg agtggaactt gaaaactcca   1680
tgggaggttt gaactttggc cgatcttact ttgatccagc atattttaga ttagggcaag   1740
agatggtaag gaggtcagct ggaaaggtca gttccacatt ggcatctgaa ctcggtatca   1800
ctgccgagga tgcaaggctt gtttcagaga ttgcaatgca tactactgag gacaagatca   1860
gtagagcggt tggacccaga caagcccaag tatcatttct acacggtgat caaagtgaga   1920
atgagctacc gagattgggg ggcaaggaag ataggagggt caaacagagt cgaggagaag   1980
ccagggagag ctacagagaa accgggccca gcagagcaag tgatgcgaga gctgcccatc   2040
ttccaaccgg cacaccccta gacattgaca ctgcaacgga gtccagccaa gatccgcagg   2100
acagtcgaag gtcagctgac gccctgctta ggctgcaagc catggcagga atctcggaag   2160
aacaaggctc agacacggac acccctatag tgtacaatga cagaaatctt ctagactagg   2220
tgcgagaggc cgagggccag aacaacatcc gcctaccatc catcattgtt ataaaaaact   2280
taggaaccag gtccacacag ccgccagccc atcaaccatc cactcccacg attggagcca   2340
atggcagaag agcaggcacg ccatgtcaaa aacggactgg aatgcatccg ggctctcaag   2400
gccgagccca tcggctcact ggccatcgag gaagctatgg cagcatggtc agaaatatca   2460
gacaacccag acaggagcg agccaccttgc agggaagaga aggcaggcag ttcgggtctc   2520
agcaaaccat gcctctcagc aattggatca actgaaggcg gtgcacctcg catccgcggt   2580
cagggacctg gagagagcga tgacgacgct gaaactttgg gaatcccccc aagaatctc    2640 caggcatcaa gcactgggtt acagtgttat tacgtttatg atcacagcgg tgaagcggtt   2700
aagggaatcc aagatgctga ctctatcatg gttcaatcag gccttgatgg tgatagcacc   2760
ctctcaggag gagacaatga atctgaaaac agcgatgtgg atattggcga acctgatacc   2820
gagggatatg ctatcactga ccggggatct gctcccatct ctatgggggtt cagggcttct   2880
```

-continued

```
gatgttgaaa ctgcagaagg aggggagatc cacgagctcc tgagactcca atccagaggc    2940
aacaactttc cgaagcttgg gaaaactctc aatgttcctc cgcccccgga ccccggtagg    3000
gccagcactt ccgggacacc cattaaaaag ggcacagacg cgagattagc ctcatttgga    3060
acggagatcg cgtctttatt gacaggtggt gcaacccaat gtgctcgaaa gtcaccctcg    3120
gaaccatcag ggccaggtgc acctgcgggg aatgtccccg agtgtgtgag caatgccgca    3180
ctgatacagg agtggacacc cgaatctggt accacaatct ccccgagatc ccagaataat    3240
gaagaagggg gagactatta tgatgatgag ctgttctctg atgtccaaga tattaaaaca    3300
gccttggcca aaatacacga ggataatcag aagataatct ccaagctaga atcactgctg    3360
ttattgaagg gagaagttga gtcaattaag aagcagatca acaggcaaaa tatcagcata    3420
tccaccctgg aaggacacct ctcaagcatc atgatcgcca ttcctggact tgggaaggat    3480
cccaacgacc ccactgcaga tgtcgaaatc aatcccgact gaaacccat cataggcaga     3540
gattcaggcc gagcactggc cgaagttctc aagaaacccg ttgccagccg acaactccaa    3600
ggaatgacaa atgacggac cagttccaga ggacagctgc tgaaggaatt tcagctaaag     3660
ccgatcggga aaaagatgag ctcagccgtc gggtttgttc ctgacaccgg ccctgcatca    3720
cgcagtgtaa tccgctccat tataaaatcc agccggctag aggaggatcg gaagcgttac    3780
ctgatgactc tccttgatga tatcaaagga gccaatgatc ttgccaagtt ccaccagatg    3840
ctgatgaaga taataatgaa gtagctacag ctcaacttac ctgccaaccc catgccagtc    3900
gacccaacta gtacaaccta atccattat aaaaaactta ggagcaaagt gattgcctcc     3960
caaggtccac aatgacagag acctacgact tcgacaagtc ggcatgggac atcaaagggt    4020
cgatcgctcc gatacaaccc accacctaca gtgatggcag gctggtgccc caggtcagag    4080
tcatagatcc tggtctaggc gacaggaagg atgaatgctt tatgtacatg tttctgctgg    4140
gggttgttga ggacagcgat tccctagggc ctccaatcgg gcgagcattt gggttcctgc    4200
ccttaggtgt tggcagatcc acagcaaagc ccgaaaaact cctcaaagag gccactgagc    4260
ttgacatagt tgttagacgt acagcagggc tcaatgaaaa actggtgttc tacaacaaca    4320
ccccactaac tctcctcaca ccttggagaa aggtcctaac aacagggagt gtcttcaacg    4380
caaaccaagt gtgcaatgcg gttaatctga taccgctcga taccccgcag aggttccgtg    4440
ttgtttatat gagcatcacc cgtctttcgg ataacgggta ttacaccgtt cctagaagaa    4500
tgctggaatt cagatcggtc aatgcagtgg ccttcaacct gctggtgacc cttaggattg    4560
acaaggcgat aggccctggg aagatcatcg acaatacaga gcaacttcct gaggcaacat    4620
ttatggtcca catcgggaac ttcaggagaa agaagagtga agtctactct gccgattatt    4680
gcaaaatgaa aatcgaaaag atgggcctgg ttttttgcact tggtgggata ggggcacca    4740
gtcttcacat tagaagcaca ggcaaaatga gcaagactct ccatgcacaa ctcgggttca    4800
agaagacctt atgttacccg ctgatggata tcaatgaaga ccttaatcga ttactctgga    4860
ggagcagatg caagatagta agaatccagg cagttttgca gccatcagtt cctcaagaat    4920
tccgcattta cgacgacgtg atcataaatg atgaccaagg actattcaaa gttctgtaga    4980
ccgtagtgcc cagcaatgcc cgaaaacgac cccctcaca atgacagcca gaaggcccgg     5040
acaaaaaagc cccctccgaa agactccacg gaccaagcga gaggccagcc agcagccgac    5100
ggcaagcgcg aacaccaggc ggccccagca cagaacagcc ctgacacaag gccaccacca    5160
gccaccccaa tctgcatcct cctcgtggga ccccgagga ccaaccccca aggctgcccc     5220
cgatccaaac caccaaccgc atccccacca ccccgggaa agaaacccc agcaattgga      5280
```

```
aggcccctcc ccctcttcct caacacaaga actccacaac cgaaccgcac aagcgaccga   5340
ggtgacccaa ccgcaggcat ccgactccct agacagatcc tctctcccg gcaaactaaa    5400 caaaacttag ggccaaggaa catacacacc caacagaacc cagaccccgg cccacggcgc   5460
cgcgccccca accccgaca accagaggga gccccaacc aatcccgccg gctccccgg      5520 tgcccacagg cagggacacc aaccccgaa cagacccagc acccaaccat cgacaatcca    5580
agacgggggg gccccccaa aaaaggccc caggggccg acagccagca ccgcgaggaa      5640
gcccacccac cccacacacg accacggcaa ccaaaccaga acccagacca ccctgggcca   5700
ccagctccca gactcggcca tcaccccgca gaaaggaaag gccacaaccc gcgcaccca    5760 gccccgatcc ggcggggagc cacccaaccc gaaccagcac ccaagagcga tccccgaagg   5820 accccgaac cgcaaaggac atcagtatcc cacagcctct ccaagtcccc cggtctcctc    5880
ctcttctcga agggaccaaa agatcaatcc accacacccg acgacactca actccccacc   5940
cctaaaggag acaccgggaa tcccagaatc aagactcatc caatgtccat catgggtctc   6000
aaggtgaacg tctctgccat attcatggca gtactgttaa ctctccaaac acccaccggt   6060
caaatccatt ggggcaatct ctctaagata ggggtggtag gaataggaag tgcaagctac   6120
aaagttatga ctcgttccag ccatcaatca ttagtcataa aattaatgcc caatataact   6180
ctcctcaata actgcacgag ggtagagatt gcagaataca ggagactact gagaacagtt   6240
ttggaaccaa ttagagatgc acttaatgca atgacccaga atataagacc ggttcagagt   6300
gtagcttcaa gtaggagaca caagagattt gcgggagtag tcctggcagg tgcggcccta   6360
ggcgttgcca cagctgctca gataacagcc ggcattgcac ttcaccagtc catgctgaac   6420
tctcaagcca tcgacaatct gagagcgagc ctggaaacta ctaatcaggc aattgagaca   6480
atcagacaag cagggcagga tgatatattg gctgttcagg gtgtccaaga ctacatcaat   6540
aatgagctga taccgtctat gaaccaacta tcttgtgatt taatcggcca gaagctcggg   6600
ctcaaattgc tcagatacta tacagaaatc ctgtcattat ttggccccag tttacgggac   6660
cccatatctg cggagatatc tatccaggct ttgagctatg cgcttggagg agacatcaat   6720
aaggtgttag aaaagctcgg atacagtgga ggtgatttac tgggcatctt agagagcgga   6780
ggaataaagg cccggataac tcacgtcgac acagagtcct acttcattgt cctcagtata   6840
gcctatccga cgctgtccga gattaagggg gtgattgtcc accggctaga gggggtctcg   6900
tacaacatag gctctcaaga gtggtatacc actgtgccca gtatgttgc aacccaaggg    6960 taccttatct cgaattttga tgagtcatcg tgtactttca tgccagaggg gactgtgtgc   7020
agccaaaatg ccttgtaccc gatgagtcct ctgctccaag aatgcctccg ggggtacacc   7080
aagtcctgtg ctcgtacact cgtatccggg tcttttggga accggttcat tttatcacaa   7140
gggaacctaa tagccaattg tgcatcaatc ctttgcaagt gttacacaac aggaacgatc   7200
attaatcaag accctgacaa gatcctaaca tacattgctg ccgatcactg cccggtagtc   7260
gaggtgaacg gcgtgaccat ccaagtcggg agcaggaggt atccagacgc tgtgtacttg   7320
cacagaattg acctcggtcc tcccatatca ttggagaggt tggacgtagg gacaaatctg   7380
gggaatgcaa ttgctaagtt ggaggatgcc aaggaattgt tggagtcatc ggaccagata   7440
ttgaggagta tgaaaggttt atcgagcact agcatagtct acatcctgat tgcagtgtgt   7500
cttggagggt tgatagggat cccgctttta atatgttgct gcaggggggcg ttgtaacaaa   7560 aagggagaac aagttggtat gtcaagacca ggcctaaagc ctgatcttac gggaacatca   7620
```

```
aaatcctatg taaggtcgct ctgatcctct acaactcttg aaacacaaat gtcccacaag    7680
tctcctcttc gtcatcaagc aaccaccgca cccagcatca agcccacctg aaattatctc    7740
cggcttccct ctggccgaac aatatcggta gttaatcaaa acttagggtg caagatcatc    7800
cacaatgtca ccacaacgag accggataaa tgccttctac aaagataacc cccatcccaa    7860
gggaagtagg atagtcatta acagagaaca tcttatgatt gatagacctt atgttttgct    7920
ggctgttctg tttgtcatgt ttctgagctt gatcgggttg ctagccattg caggcattag    7980
acttcatcgg gcagccatct acaccgcaga gatccataaa agcctcagca ccaatctaga    8040
tgtaactaac tcaatcgagc atcaggtcaa ggacgtgctg acaccactct tcaaaatcat    8100
cggtgatgaa gtgggcctga ggacacctca gagattcact gacctagtga aattaatctc    8160
tgacaagatt aaattcctta atccggatag ggagtacgac ttcagagatc tcacttggtg    8220
tatcaacccg ccagagagaa tcaaattgga ttatgatcaa tactgtgcag atgtggctgc    8280
tgaagagctc atgaatgcat tggtgaactc aactctactg gagaccagaa caaccaatca    8340
gttcctagct gtctcaaagg gaaactgctc agggcccact acaatcagag gtcaattctc    8400
aaacatgtcg ctgtccctgt tagacttgta tttaggtcga ggttacaatg tgtcatctat    8460
agtcactatg acatcccagg gaatgtatgg gggaacttac ctagtggaaa agcctaatct    8520
gagcagcaaa aggtcagagt tgtcacaact gagcatgtac cgagtgtttg aagtaggtgt    8580
tatcagaaat ccgggtttgg gggctccggt gttccatatg acaaactatc ttgagcaacc    8640
agtcagtaat gatctcagca actgtatggt ggctttgggg gagctcaaac tcgcagccct    8700
ttgtcacggg gaagattcta tcacaattcc ctatcaggga tcaggaaagg gtgtcagctt    8760
ccagctcgtc aagctaggtg tctggaaatc cccaaccgac atgcaatcct gggtcccctt    8820
atcaacggat gatccagtga tagacaggct ttacctctca tctcacagag gtgttatcgc    8880
tgacaatcaa gcaaatgggc tgtcccgac aacacgaaca gatgacaagt gcgaatggaa    8940
gacatgcttc caacaggcgt gtaagggtaa atccaagca ctctgcgaga atcccgagtg    9000
ggcaccattg aaggataaca ggattccttc atacgggtc ttgtctgttg atctgagtct    9060
gacagttgag cttaaaatca aaattgcttc gggattcggg ccattgatca cacacggttc    9120
agggatggac ctatacaaat ccaaccacaa caatgtgtat tggctgacta tcccgccaat    9180
gaagaaccta gccttaggtg taatcaacac attggagtgg ataccgagat tcaaggttag    9240
tccctacctc ttcactgtcc caattaagga agcaggcgaa gactgccatg ccccaacata    9300
cctacctgcg gaggtggatg gtgatgtcaa actcagttcc aatctggtga ttctacctgg    9360
tcaagatctc caatatgttt tggcaaccta cgatacttcc agggttgaac atgctgtggt    9420
ttattacgtt tacagcccaa gccgctcatt ttcttacttt tatccttta ggttgcctat    9480 aaaggggtc cccatcgaat tacaagtgga atgcttcaca tgggaccaaa aactctggtg    9540
ccgtcacttc tgtgtgcttg cggactcaga atctggtgga catatcactc actctgggat    9600
ggtgggcatg ggagtcagct gcacagtcac ccgggaagat ggaaccaatc gcagataggg    9660
ctgctagtga accaatcaca tgatgtcacc cagacatcag gcatacccac tagtcatcca    9720
tcattgttat aaaaaactta ggaaccaggt ccacacagct cgagtcgcgc gtgccaccat    9780
ggaaacccca gcacagcttc tcttcctcct gctgctctgg ctcccagata ccactggaga    9840
gattgtgctg acgcaatccc ctgggactct ctcccttttcc cctggcgaac gggctacact    9900
gtcctgcaga gcttcacaga gcgttgggtc cagctatctc gcctggtacc agcagaaacc    9960
aggccaagca ccacgcctgc tcatctatgg tgcctttagc agagccactg gcatacccga    10020
```

```
taggttcagc ggctcaggca gcggtacaga cttcacgctg accattagcc ggctggaacc   10080
cgaggatttc gcagtgtact attgccagca gtatgggagc tctccgtgga catttggcca   10140
agggacaaag gtggagatta agcgcggtgg tggtggatca ggtggaggcg aagtggagg    10200
tggcggatcc caggtacagc tggtcgagtc tggtggcggc gtagtgcaac ccggaagaag   10260
tttgcgactg tcatgcgcag cttctgggtt taccttcagc tcctatacaa tgcactgggt   10320
caggcaggct ccagggaaag gcctggagtg ggtcaccttc atctcttacg acgggaacaa   10380
caagtactac gcggattcag tgaaaggacg gtttaccatc tcccgcgaca attccaagaa   10440
taccctgtat ctccagatga acagcttgag agccgaagat accgccatct actactgtgc   10500
caggactgga tggcttgggc cttttgacta ctggggccag ggtactctgg tgactgttag   10560
ttcagtcgac gaggccaaat cttgtgacaa aactcacaca tgcccaccgt gcccagcacc   10620
cgaactcctg ggggaccgt cagtcttcct cttcccccca aaacccaagg acaccctcat    10680
gatctcccgg acccctgagg tcacatgcgt ggtggtggac gtgagccacg aagaccctga   10740
ggtcaagttc aactggtacg tggacggcgt ggaggtgcat aatgccaaga caaagccgcg   10800
ggaggagcag tacaacagca cgtaccgtgt ggtcagcgtc ctcaccgtcc tgcaccagga   10860
ctggctgaat ggcaaggagt acaagtgcaa ggtctccaac aaagcccctcc cagcccccat  10920
cgagaaaacc atctccaaag ccaaggggca gccccgagaa ccacaggtgt acaccctgcc   10980
cccatcccgg gatgagctga ccaagaacca ggtcagcctg acctgcctgg tcaaaggctt   11040
ctatcccagc gacatcgccg tggagtggga gagcaatggg cagccggaga caactacaa    11100
gaccacgcct cccgtgctgg actccgacgg ctccttcttc ctctacagca agctcaccgt   11160
ggacaagagc aggtggcagc aggggaacgt cttctcatgc tccgtgatgc atgaggctct   11220
gcacaaccac tacacgcaga agagcctctc cctgtctccg ggtaaagtcg acaattaggc   11280
gcgcgttcta gtgtgaaata gacatcagaa ttaagaaaaa cgtagggtcc aagtggttcc   11340
ccgttatgga ctcgctatct gtcaaccaga tcttataccc tgaagttcac ctagatagcc   11400
cgatagttac caataagata gtagccatcc tggagtatgc tcgagtccct cacgcttaca   11460
gcctggagga ccctacactg tgtcagaaca tcaagcaccg cctaaaaaac ggattttcca   11520
accaaatgat tataaacaat gtggaagttg gaatgtcat caagtccaag cttaggagtt    11580
atccggccca ctctcatatt ccatatccaa attgtaatca ggatttattt aacatagaag   11640
acaaagagtc aacgaggaag atccgtgaac tcctcaaaaa ggggaattcg ctgtactcca   11700
aagtcagtga taaggttttc caatgcttaa gggacactaa ctcacggctt ggcctaggct   11760
ccgaattgag ggaggacatc aaggagaaag ttattaactt gggagtttac atgcacagct   11820
cccagtggtt tgagcccttt ctgttttggt ttacagtcaa gactgagatg aggtcagtga   11880
ttaaatcaca aacccatact tgccatagga ggagacacac acctgtattc ttcactggta   11940
gttcagttga gttgctaatc tctcgtgacc ttgttgctat aatcagtaaa gagtctcaac   12000
atgtatatta cctgacattt gaactggttt tgatgtattg tgatgtcata gagggaggt    12060
taatgacaga gaccgctatg actattgatg ctaggtatac agagcttcta ggaagagtca   12120
gatacatgtg gaaactgata gatggtttct tccctgcact cggaatcca acttatcaaa    12180
ttgtagccat gctggagcct ctttcacttg cttacctgca gctgagggat ataacagtag   12240
aactcagagg tgctttcctt aaccactgct ttactgaaat acatgatgtt cttgaccaaa   12300
acggtttttc tgatgaaggt acttatcatg agttaactga agctctagat tacatttttca  12360
```

```
taactgatga catacatctg acaggggaga ttttctcatt tttcagaagt ttcggccacc    12420
ccagacttga agcagtaacg gctgctgaaa atgttaggaa atacatgaat cagcctaaag    12480
tcattgtgta tgagactctg atgaaaggtc atgccatatt ttgtggaatc ataatcaacg    12540
gctatcgtga caggcacgga ggcagttggc caccgctgac cctcccccctg catgctgcag   12600 acacaatccg gaatgctcaa gcttcaggtg aagggttaac acatgagcag tgcgttgata    12660
actggaaatc ttttgctgga gtgaaatttg gctgctttat gcctcttagc ctggatagtg    12720
atctgacaat gtacctaaag gacaaggcac ttgctgctct ccaaagggaa tgggattcag    12780
tttacccgaa agagttcctg cgttacgacc ctcccaaggg aaccgggtca cggaggcttg    12840
tagatgtttt ccttaatgat tcgagctttg acccatatga tgtgataatg tatgttgtaa    12900
gtggagctta cctccatgac cctgagttca acctgtctta cagcctgaaa gaaaaggaga    12960
tcaaggaaac aggtagactt tttgctaaaa tgacttacaa aatgagggca tgccaagtga    13020
ttgctgaaaa tctaatctca aacgggattg gcaaatattt taaggacaat gggatggcca    13080
aggatgagca cgatttgact aaggcactcc acactctagc tgtctcagga gtccccaaag    13140
atctcaaaga aagtcacagg ggggggccag tcttaaaaac ctactcccga agcccagtcc    13200
acacaagtac caggaacgtg agagcagcaa aagggtttat agggttccct caagtaattc    13260
ggcaggacca agacactgat catccggaga atatggaagc ttacgagaca gtcagtgcat    13320
ttatcacgac tgatctcaag aagtactgcc ttaattggag atatgagacc atcagcttgt    13380
ttgcacagag gctaaatgag atttacggat tgccctcatt tttccagtgg ctgcataaga    13440
ggcttgagac ctctgtcctg tatgtaagtg accctcattg ccccccccgac cttgacgccc    13500 atatcccgtt atataaagtc cccaatgatc aaatcttcat taagtaccct atgggaggta    13560
tagaagggta ttgtcagaag ctgtggacca tcagcaccat tccctatcta tacctggctg    13620
cttatgagag cggagtaagg attgcttcgt tagtgcaagg ggacaatcag accatagccg    13680
taacaaaaag ggtacccagc acatggccct acaaccttaa gaaacgggaa gctgctagag    13740
taactagaga ttactttgta attcttaggc aaaggctaca tgatattggc catcacctca    13800
aggcaaatga gacaattgtt tcatcacatt tttttgtcta ttcaaaagga atatattatg    13860
atgggctact tgtgtcccaa tcactcaaga gcatcgcaag atgtgtattc tggtcagaga    13920
ctatagttga tgaaacaagg gcagcatgca gtaatattgc tacaacaatg gctaaaagca    13980
tcgagagagg ttatgaccgt taccttgcat attccctgaa cgtcctaaaa gtgatacagc    14040
aaattctgat ctctcttggc ttcacaatca attcaaccat gacccgggat gtagtcatac    14100
ccctcctcac aaacaacgac ctcttaataa ggatggcact gttgcccgct cctattgggg    14160
ggatgaatta tctgaatatg agcaggctgt ttgtcagaaa catcggtgat ccagtaacat    14220
catcaattgc tgatctcaag agaatgattc tcgcctcact aatgcctgaa gagaccctcc    14280
atcaagtaat gacacaacaa ccgggggact cttcattcct agactgggct agcgacccct    14340
actcagcaaa tcttgtatgt gtccagagca tcactagact cctcaagaac ataactgcaa    14400 ggttttgtcct gatccatagt ccaaacccaa tgttaaaagg attattccat gatgacagta    14460
aagaagagga cgagggactg gcggcattcc tcatggacag gcatattata gtacctaggg    14520
cagctcatga atcctggat catagtgtca caggggcaag agagtctatt gcaggcatgc    14580
tggataccac aaaaggcttg attcgagcca gcatgaggaa gggggggtta acctctcgag    14640
tgataaccga attgtccaat tatgactatg aacaattcag agcagggatg gtgctattga    14700
caggaagaaa gagaaatgtc ctcattgaca aagagtcatg ttcagtgcag ctggcagagag   14760
```

```
ctctaagaag ccatatgtgg gcgaggctag ctcgaggacg gcctatttac ggccttgagg   14820
tccctgatgt actagaatct atgcgaggcc accttattcg gcgtcatgag acatgtgtca   14880
tctgcgagtg tggatcagtc aactacggat ggttttttgt cccctcgggt tgccaactgg   14940
atgatattga caaggaaaca tcatccttga gagtcccata tattggttct accactgatg   15000
agagaacaga catgaagctt gccttcgtaa gagccccaag tcgatccttg cgatctgctg   15060
ttagaatagc aacagtgtac tcatgggctt acggtgatga tgatagctct tggaacgaag   15120
cctggttgtt ggctaggcaa agggccaatg tgagcctgga ggagctaagg gtgatcactc   15180
ccatctcaac ttcgactaat ttagcgcata ggttgaggga tcgtagcact caagtgaaat   15240
actcaggtac atcccttgtc cgagtggcga ggtataccac aatctccaac gacaatctct   15300
catttgtcat atcagataag aaggttgata ctaactttat ataccaacaa ggaatgcttc   15360
tagggttggg tgttttagaa acattgtttc gactcgagaa agataccgga tcatctaaca   15420
cggtattaca tcttcacgtc gaaacagatt gttgcgtgat cccgatgata gatcatccca   15480
ggatacccag ctcccgcaag ctagagctga gggcagagct atgtaccaac ccattgatat   15540
atgataatgc acctttaatt gacagagatg caacaaggct atacacccag agccatagga   15600
ggcaccttgt ggaatttgtt acatggtcca cacccccaact atatcacatt ttagctaagt   15660
```

```
tgcctttcag cggggatttt gttcagggat ttataagtta tgtagggtct cattatagag  17160
aagtgaacct tgtataccct agatacagca acttcatctc tactgaatct tatttggtta  17220
tgacagatct caaggctaac cggctaatga atcctgaaaa gattaagcag cagataattg  17280
aatcatctgt gaggacttca cctggactta taggtcacat cctatccatt aagcaactaa  17340
gctgcataca agcaattgtg ggagacgcag ttagtagagg tgatatcaat cctactctga  17400
aaaaacttac acctatagag caggtgctga tcaattgcgg gttggcaatt aacggaccta  17460
agctgtgcaa agaattgatc caccatgatg ttgcctcagg gcaagatgga ttgcttaatt  17520
ctatactcat cctctacagg gagttggcaa gattcaaaga caaccaaaga agtcaacaag  17580
ggatgttcca cgcttacccc gtattggtaa gtagcaggca acgagaactt atatctagga  17640
tcacccgcaa attctggggg cacattcttc tttactccgg gaacaaaaag ttgataaata  17700
agtttatcca gaatctcaag tccggctatc tgatactaga cttacaccag aatatcttcg  17760
ttaagaatct atccaagtca gagaaacaga ttattatgac ggggggtttg aaacgtgagt  17820
gggtttttaa ggtaacagtc aaggagacca aagaatggta taagttagtc ggatacagtg  17880
ccctgattaa ggactaattg gttgaactcc ggaaccctaa tcctgcccta ggtggttagg  17940
cattatttgc aatatattaa agaaaacttt gaaaatacga agtttctatt cccagctttg  18000
tctggt                                                             18006
```

<210> SEQ ID NO 9
<211> LENGTH: 19062
<212> TYPE: DNA
<213> ORGANISM: Artificial
<220> FEATURE:
<223> OTHER INFORMATION: MeV Schwarz virus genome encoding cDNA for secretable (human) antibody anti-human PD-L1 and encoding cDNA for secretable (human) antibody anti-human CTLA-4

<400> SEQUENCE: 9

```
accaaacaaa gttgggtaag gatagttcaa tcaatgatca tcttctagtg cacttaggat     60
tcaagatcct attatcaggg acaagagcag gattagggat atccgagatg gccacacttt    120
taaggagctt agcattgttc aaaagaaaca aggacaaacc acccattaca tcaggatccg    180
gtggagccat cagaggaatc aaacacatta ttatagtacc aatccctgga gattcctcaa    240
ttaccactcg atccagactt ctggaccggt tggtgaggtt aattggaaac ccggatgtga    300
gcgggcccaa actaacaggg gcactaatag gtatattatc cttatttgtg gagtctccag    360
gtcaattgat tcagaggatc accgatgacc ctgacgttag cataaggctg ttagaggttg    420
tccagagtga ccagtcacaa tctggcctta ccttcgcatc aagaggtacc aacatggagg    480
atgaggcgga ccaatacttt tcacatgatg atccaattag tagtgatcaa tccaggttcg    540
gatggttcgg gaacaaggaa atctcagata ttgaagtgca agaccctgag ggattcaaca    600
tgattctggg taccatccta gcccaaattt gggtcttgct cgcaaaggcg gttacggccc    660
cagacacggc agctgattcg gagctaagaa ggtggataaa gtacacccaa caaagaaggg    720
tagttggtga atttagattg gagagaaaat ggttggatgt ggtgaggaac aggattgccg    780
aggacctctc cttacgccga ttcatggtcg ctctaatcct ggatatcaag agaacacccg    840
gaaacaaacc caggattgct gaaatgatat gtgacattga tacatatatc gtagaggcag    900
gattagccag ttttatcctg actattaagt ttgggataga aactatgtat cctgctcttg    960
gactgcatga atttgctggt gagttatcca cacttgagtc cttgatgaac ctttaccagc   1020 aaatgggga aactgcaccc tacatggtaa tcctggagaa ctcaattcag aacaagttca   1080
```

```
gtgcaggatc ataccctctg ctctggagct atgccatggg agtaggagtg gaacttgaaa    1140
actccatggg aggtttgaac tttggccgat cttactttga tccagcatat tttagattag    1200
ggcaagagat ggtaaggagg tcagctggaa aggtcagttc cacattggca tctgaactcg    1260
gtatcactgc cgaggatgca aggcttgttt cagagattgc aatgcatact actgaggaca    1320
agatcagtag agcggttgga cccagacaag cccaagtatc atttctacac ggtgatcaaa    1380
gtgagaatga gctaccgaga ttgggggggca aggaagatag gagggtcaaa cagagtcgag    1440
gagaagccag ggagagctac agagaaaccg gcccagcag agcaagtgat gcgagagctg      1500
cccatcttcc aaccggcaca cccctagaca ttgacactgc aacggagtcc agccaagatc    1560
cgcaggacag tcgaaggtca gctgacgccc tgcttaggct gcaagccatg gcaggaatct    1620
cggaagaaca aggctcagac acggacaccc ctatagtgta caatgacaga aatcttctag    1680
actaggtgcg agaggccgag ggccagaaca acatccgcct accatccatc attgttataa    1740
aaaacttagg aaccaggtcc acacagccgc cagcccatca accatccact cccacgattg    1800
gagccaatgg cagaagagca ggcacgccat gtcaaaaacg gactggaatg catccgggct    1860
ctcaaggccg agcccatcgg ctcactggcc atcgaggaag ctatggcagc atggtcagaa    1920
atatcagaca acccaggaca ggagcgagcc acctgcaggg aagagaaggc aggcagttcg    1980
ggtctcagca aaccatgcct ctcagcaatt ggatcaactg aaggcggtgc acctcgcatc    2040
cgcggtcagg gacctggaga gagcgatgac gacgctgaaa ctttgggaat cccccaaga     2100 aatctccagg catcaagcac tgggttacag tgttattacg tttatgatca cagcggtgaa    2160
gcggttaagg gaatccaaga tgctgactct atcatggttc aatcaggcct tgatggtgat    2220
agcaccctct caggaggaga caatgaatct gaaaacagcg atgtggatat tggcgaacct    2280
gataccgagg gatatgctat cactgaccgg ggatctgctc ccatctctat ggggttcagg    2340
gcttctgatg ttgaaactgc agaaggaggg gagatccacg agctcctgag actccaatcc    2400
agaggcaaca actttccgaa gcttgggaaa actctcaatg ttcctccgcc cccggacccc    2460
ggtagggcca gcacttccgg gacacccatt aaaaagggca cagacgcgag attagcctca    2520
tttggaacgg agatcgcgtc tttattgaca ggtggtgcaa cccaatgtgc tcgaaagtca    2580
ccctcggaac catcagggcc aggtgcacct gcggggaatg tccccgagtg tgtgagcaat    2640
gccgcactga tacaggagtg gacacccgaa tctggtacca caatctcccc gagatcccag    2700
aataatgaag aagggggaga ctattatgat gatgagctgt tctctgatgt ccaagatatt    2760
aaaacagcct tggccaaaat acacgaggat aatcagaaga taatctccaa gctagaatca    2820
ctgctgttat tgaagggaga agttgagtca attaagaagc agatcaacag gcaaaatatc    2880
agcatatcca ccctgaagg acacctctca agcatcatga tcgccattcc tggacttggg    2940
aaggatccca acgaccccac tgcagatgtc gaaatcaatc ccgacttgaa acccatcata    3000
ggcagagatt caggccgagc actggccgaa gttctcaaga acccgttgc cagccgacaa      3060 ctccaaggaa tgacaaatgg acggaccagt tccagaggac agctgctgaa ggaatttcag    3120
ctaaagccga tcgggaaaaa gatgagctca gccgtcgggt tgttcctga caccggccct     3180 gcatcacgca gtgtaatccg ctccattata aaatccagcc ggctagagga ggatcggaag    3240
cgttacctga tgactctcct tgatgatatc aaaggagcca atgatcttgc caagttccac    3300
cagatgctga tgaagataat aatgaagtag ctacagctca acttacctgc aacccccatg    3360
ccagtcgacc caactagcaa cctaaatcca ttataaaaaa cttaggaacc aggtccacac    3420
```

```
agctcgagtc gcgcgtgcca ccatggaaac cccagcacag cttctcttcc tcctgctgct    3480
ctggctccca gataccactg gagagattgt cctgacacag agcccagcta cactttccct    3540
gtctccgggc gaaagagcaa ccctctcttg cagggctagc cagtctgtca gctcttatct    3600
cgcctggtat cagcagaaac caggccaggc tcccagactg ctgatctacg acgctagcaa    3660
tcgcgccact ggcataccag cacgcttttc agggtccggc agtggtaccg acttcaccct    3720
gaccatctcc tcactggaac ctgaggactt tgccgtgtat tactgtcaac agcggagtaa    3780
ctggcccacc tttgggcagg gcactaaggt ggagatcaaa cgcggtggtg gtggatcagg    3840
tggaggcgga agtggaggtg gcggatccca ggtgcaactg gtacagagcg gcgcagaagt    3900
gaagaaaccc gggtcctcag tgaaggtcag ttgcaagaca tccggggaca ccttctcaac    3960
gtatgccatt agctgggtta cacaggctcc tggtcaaggg cttgagtgga tgggaggtat    4020
cattcccata ttcgggaaag cgcattatgc ccagaagttc caaggcaggg tcaccatcac    4080
tgccgatgaa tccacaagta ctgcctacat ggagttgagc tccttgcgta gcgaggatac    4140
tgcggtgtac ttttgtgcac ggaagtttca cttcgtttca gggagccctt tcgggatgga    4200
tgtttgggga cagggtacaa cggtgacagt atccagcgtc gacgaggcca aatcttgtga    4260
caaaactcac acatgcccac cgtgcccagc acccgaactc ctgggaggac cgtcagtctt    4320
cctcttcccc ccaaaaccca aggacaccct catgatctcc cggacccctg aggtcacatg    4380
cgtggtggtg gacgtgagcc acgaagaccc tgaggtcaag ttcaactggt acgtggacgg    4440
cgtggaggtg cataatgcca agacaaagcc gcgggaggag cagtacaaca gcacgtaccg    4500
tgtggtcagc gtcctcaccg tcctgcacca ggactggctg aatggcaagg agtacaagtg    4560
caaggtctcc aacaaagccc tcccagcccc catcgagaaa accatctcca aagccaaggg    4620 gcagcccega gaaccacagg tgtacaccct gcccccatcc cgggatgagc tgaccaagaa    4680
ccaggtcagc ctgacctgcc tggtcaaagg cttctatccc agcgacatcg ccgtggagtg    4740
ggagagcaat gggcagccgg agaacaacta caagaccacg cctcccgtgc tggactccga    4800
cggctccttc ttcctctaca gcaagctcac cgtggacaag agcaggtggc agcagggggaa    4860 cgtcttctca tgctccgtga tgcatgaggc tctgcacaac cactacacgc agaagagcct    4920
ctccctgtct ccgggtaaag tcgacaatta ataggcgcgc gtgctagtac aacctaaatc    4980
cattataaaa aacttaggag caaagtgatt gcctcccaag gtccacaatg acagagacct    5040
acgacttcga caagtcggca tgggacatca aagggtcgat cgctccgata caacccacca    5100
cctacagtga tggcaggctg gtgccccagg tcagagtcat agatcctggt ctaggcgaca    5160
ggaaggatga atgctttatg tacatgtttc tgctggggt tgttgaggac agcgattccc    5220
tagggcctcc aatcgggcga gcatttgggt tcctgcccett aggtgttggc agatccacag    5280
caaagcccga aaaactcctc aaagaggcca ctgagcttga catagttgtt agacgtacag    5340
cagggctcaa tgaaaaactg gtgttctaca caacaccccc actaactctc ctcacacctt    5400
ggagaaaggt cctaacaaca gggagtgtct tcaacgcaaa ccaagtgtgc aatgcggtta    5460 atctgataccc gctcgatacc ccgcagaggt tccgtgttgt ttatatgagc atcacccgtc    5520
tttcggataa cggtattac accgttccta gaagaatgct ggaattcaga tcggtcaatg    5580
cagtggcctt caacctgctg gtgacccta ggattgacaa ggcgataggc cctgggaaga    5640
tcatcgacaa tacagagcaa cttcctgagg caacatttat ggtccacatc gggaacttca    5700
ggagaaagaa gagtgaagtc tactctgccg attattgcaa aatgaaaatc gaaaagatgg    5760
gcctggtttt tgcacttggt gggataggg gcaccagtct tcacattaga agcacaggca    5820
```

```
aaatgagcaa gactctccat gcacaactcg ggttcaagaa gaccttatgt tacccgctga    5880
tggatatcaa tgaagacctt aatcgattac tctggaggag cagatgcaag atagtaagaa    5940
tccaggcagt tttgcagcca tcagttcctc aagaattccg catttacgac gacgtgatca    6000
taaatgatga ccaaggacta ttcaaagttc tgtagaccgt agtgcccagc aatgcccgaa    6060
aacgaccccc ctcacaatga cagccagaag gcccggacaa aaagcccccc tccgaaagac    6120
tccacggacc aagcgagagg ccagccagca gccgacggca agcgcgaaca ccaggcggcc    6180
ccagcacaga acagccctga cacaaggcca ccaccagcca ccccaatctg catcctcctc    6240
gtgggacccc cgaggaccaa cccccaaggc tgcccccgat ccaaccacc aaccgcatcc     6300 ccaccacccc cgggaaagaa accccagca attggaaggc cctcccccct cttcctcaac     6360
acaagaactc cacaaccgaa ccgcacaagc gaccgaggtg acccaaccgc aggcatccga    6420
ctccctagac agatcctctc tccccggcaa actaaacaaa acttagggcc aaggaacata    6480
cacacccaac agaacccaga cccccggccca cggcgccgcg cccccaaccc ccgacaacca   6540
gagggagccc ccaaccaatc ccgccggctc ccccggtgcc cacaggcagg gacaccaacc    6600
cccgaacaga cccagcaccc aaccatcgac aatccaagac gggggggccc cccaaaaaaa    6660
aggcccccag gggccgacag ccagccaccgc gaggaagccc acccacccca cacacgacca   6720
cggcaaccaa accagaaccc agaccaccct gggccaccag ctcccagact cggccatcac    6780
cccgcagaaa ggaaaggcca caacccgcgc accccagccc cgatccggcg gggagccacc    6840
caacccgaac cagcacccaa gagcgatccc cgaaggaccc ccgaaccgca aaggacatca    6900
gtatcccaca gcctctccaa gtcccccggt ctcctcctct tctcgaaggg accaaaagat    6960
caatccacca cacccgacga cactcaactc cccaccccta aaggagacac cgggaatccc    7020
agaatcaaga ctcatccaat gtccatcatg ggtctcaagg tgaacgtctc tgccatattc    7080
atggcagtac tgttaactct ccaaacaccc accggtcaaa tccattgggg caatctctct    7140
aagatagggg tggtaggaat aggaagtgca agctacaaag ttatgactcg ttccagccat    7200
caatcattag tcataaaatt aatgcccaat ataactctcc tcaataactg cacgagggta    7260
gagattgcag aatacaggag actactgaga acagttttgg aaccaattag agatgcactt    7320
aatgcaatga cccagaatat aagaccggtt cagagtgtag cttcaagtag gagacacaag    7380
agatttgcgg gagtagtcct ggcaggtgcg gccctaggcg ttgccacagc tgctcagata    7440
acagccggca ttgcacttca ccagtccatg ctgaactctc aagccatcga caatctgaga    7500
gcgagcctgg aaactactaa tcaggcaatt gagacaatca gacaagcagg caggagatg    7560 atattggctg ttcagggtgt ccaagactac atcaataatg agctgatacc gtctatgaac    7620
caactatctt gtgatttaat cggcagaag ctcgggctca aattgctcag atactataca    7680
gaaatcctgt cattatttgg ccccagttta cgggacccca tatctgcgga gatatctatc    7740
caggctttga gctatgcgct tggaggagac atcaataagg tgttagaaaa gctcggatac    7800
agtggaggtg atttactggg catcttagag agcggaggaa taaaggcccg gataactcac    7860
gtcgacacag agtcctactt cattgtcctc agtatagcct atccgacgct gtccgagatt    7920
aagggggtga ttgtccaccg gctagagggg gtctcgtaca acataggctc tcaagagtgg    7980
tataccactg tgcccaagta tgttgcaacc caagggtacc ttatctcgaa ttttgatgag    8040
tcatcgtgta ctttcatgcc agaggggact gtgtgcagcc aaaatgcctt gtacccgatg    8100
agtcctctgc tccaagaatg cctccggggg tacaccaagt cctgtgctcg tacactcgta    8160
```

```
tccgggtctt ttgggaaccg gttcatttta tcacaaggga acctaatagc caattgtgca    8220
tcaatccttt gcaagtgtta cacaacagga acgatcatta atcaagaccc tgacaagatc    8280
ctaacataca ttgctgccga tcactgcccg gtagtcgagg tgaacggcgt gaccatccaa    8340
gtcgggagca ggaggtatcc agacgctgtg tacttgcaca gaattgacct cggtcctccc    8400
atatcattgg agaggttgga cgtagggaca aatctgggga atgcaattgc taagttggag    8460
gatgccaagg aattgttgga gtcatcggac cagatattga ggagtatgaa aggtttatcg    8520
agcactagca tagtctacat cctgattgca gtgtgtcttg gagggttgat agggatcccc    8580
gctttaatat gttgctgcag ggggcgttgt aacaaaaagg gagaacaagt tggtatgtca    8640
agaccaggcc taaagcctga tcttacggga acatcaaaat cctatgtaag gtcgctctga    8700
tcctctacaa ctcttgaaac acaaatgtcc cacaagtctc ctcttcgtca tcaagcaacc    8760
accgcaccca gcatcaagcc cacctgaaat tatctccggc ttccctctgg ccgaacaata    8820
tcggtagtta atcaaaactt agggtgcaag atcatccaca atgtcaccac aacgagaccg    8880
gataaatgcc ttctacaaag ataaccccca tcccaaggga agtaggatag tcattaacag    8940
agaacatctt atgattgata gaccttatgt tttgctggct gttctgtttg tcatgtttct    9000
gagcttgatc gggttgctag ccattgcagg cattagactt catcgggcag ccatctacac    9060
cgcagagatc cataaaagcc tcagcaccaa tctagatgta actaactcaa tcgagcatca    9120
ggtcaaggac gtgctgacac cactcttcaa aatcatcggt gatgaagtgg gcctgaggac    9180
acctcagaga ttcactgacc tagtgaaatt aatctctgac aagattaaat tccttaatcc    9240
ggatagggag tacgacttca gagatctcac ttggtgtatc aacccgccag agagaatcaa    9300
attggattat gatcaatact gtgcagatgt ggctgctgaa gagctcatga atgcattggt    9360
gaactcaact ctactggaga ccagaacaac caatcagttc ctagctgtct caaagggaaa    9420
ctgctcaggg cccactacaa tcagaggtca attctcaaac atgtcgctgt ccctgttaga    9480
cttgtattta ggtcgaggtt acaatgtgtc atctatagtc actatgacat cccagggaat    9540
gtatggggga acttacctag tggaaaagcc taatctgagc agcaaaaggt cagagttgtc    9600
acaactgagc atgtaccgag tgtttgaagt aggtgttatc agaaatccgg gtttgggggc    9660
tccggtgttc catatgacaa actatcttga gcaaccagtc agtaatgatc tcagcaactg    9720
tatggtggct ttgggggagc tcaaactcgc agccctttgt cacggggaag attctatcac    9780
aattccctat cagggatcag ggaaaggtgt cagcttccag ctcgtcaagc taggtgtctg    9840
gaaatcccca accgacatgc aatcctgggt ccccttatca acggatgatc cagtgataga    9900
caggctttac ctctcatctc acagaggtgt tatcgctgac aatcaagcaa aatgggctgt    9960
cccgacaaca cgaacagatg acaagttgcg aatggagaca tgcttccaac aggcgtgtaa    10020
gggtaaaatc caagcactct gcgagaatcc cgagtgggca ccattgaagg ataacaggat    10080
tccttcatac ggggtcttgt ctgttgatct gagtctgaca gttgagctta aaatcaaaat    10140
tgcttcggga ttcgggccat tgatcacaca cggttcaggg atggacctat acaaatccaa    10200
ccacaacaat gtgtattggc tgactatccc gccaatgaag aacctagcct taggtgtaat    10260
caacacattg gagtggatac cgagattcaa ggttagtccc tacctcttca ctgtcccaat    10320
taaggaagca ggcgaagact gccatgcccc aacatacctg cctgcggagg tggatggtga    10380
tgtcaaactc agttccaatc tggtgattct acctggtcaa gatctccaat atgttttggc    10440
aacctacgat acttccaggg ttgaacatgc tgtggtttat tacgtttaca gcccaagccg    10500 ctcatttttct tactttatc cttttaggtt gcctataaag ggggtcccca tcgaattaca    10560
```

```
agtggaatgc ttcacatggg accaaaaact ctggtgccgt cacttctgtg tgcttgcgga    10620
ctcagaatct ggtggacata tcactcactc tgggatggtg ggcatgggag tcagctgcac    10680
agtcacccgg gaagatggaa ccaatcgcag atagggctgc tagtgaacca atcacatgat    10740
gtcacccaga catcaggcat acccactagt catccatcat tgttataaaa aacttaggaa    10800
ccaggtccac acagctcgag tcgcgcgtgc caccatggaa ccccagcac agcttctctt     10860 cctcctgctg ctctggctcc cagataccac tggagagatt gtgctgacgc aatcccctgg    10920
gactctctcc cttttccctg gcgaacgggc tacactgtcc tgcagagctt cacagagcgt    10980
tgggtccagc tatctcgcct ggtaccagca gaaaccaggc caagcaccac gcctgctcat    11040
ctatggtgcc tttagcagag ccactggcat acccgatagg ttcagcggct caggcagcgg    11100
tacagacttc acgctgacca ttagccggct ggaacccgag gatttcgcag tgtactattg    11160
ccagcagtat gggagctctc cgtggacatt tggccaaggg acaaaggtgg agattaagcg    11220
cggtggtggt ggatcaggtg gaggcggaag tggaggtggc ggatcccagg tacagctggt    11280
cgagtctggt ggcggcgtag tgcaacccgg aagaagtttg cgactgtcat gcgcagcttc    11340
tgggtttacc ttcagctcct atacaatgca ctgggtcagg caggctccag ggaaaggcct    11400
ggagtgggtc accttcatct cttacgacgg gaacaacaag tactacgcgg attcagtgaa    11460
aggacggttt accatctccc gcgacaattc caagaatacc ctgtatctcc agatgaacag    11520
cttgagagcc gaagataccg ccatctacta ctgtgccagg actggatggc ttgggccttt    11580
tgactactgg ggccagggta ctctggtgac tgttagttca gtcgacgagg ccaaatcttg    11640
tgacaaaact cacacatgcc caccgtgccc agcacccgaa ctcctggggg gaccgtcagt    11700
cttcctcttc cccccaaaac ccaaggacac cctcatgatc tcccggaccc ctgaggtcac    11760
atgcgtggtg gtggacgtga gccacgaaga cctgaggtc aagttcaact ggtacgtgga     11820
cggcgtggag gtgcataatg ccaagacaaa gccgcgggag gagcagtaca acagcacgta    11880
ccgtgtggtc agcgtcctca ccgtcctgca ccaggactgg ctgaatggca aggagtacaa    11940
gtgcaaggtc tccaacaaag cccteccagc ccccatcgag aaaaccatct ccaaagccaa    12000
ggggcagccc cgagaaccac aggtgtacac cctgcccccA tcccgggatg agctgaccaa    12060
gaaccaggtc agcctgacct gcctggtcaa aggcttctat cccagcgaca tcgccgtgga    12120
gtgggagagc aatgggcagc cggagaacaa ctacaagacc acgcctcccg tgctggactc    12180
cgacggctcc ttcttcctct acagcaagct caccgtggac aagagcaggt ggcagcaggg    12240
gaacgtcttc tcatgctccg tgatgcatga ggctctgcac aaccactaca cgcagaagag    12300
cctctccctg tctccgggta aagtcgacaa ttaggcgcgc gttctagtgt gaaatagaca    12360
tcagaattaa gaaaaacgta gggtccaagt ggttccccgt tatggactcg ctatctgtca    12420
accagatctt ataccctgaa gttcacctag atagcccgat agttaccaat aagatagtag    12480
ccatcctgga gtatgctcga gtccctcacg cttacagcct ggaggaccct acactgtgtc    12540
agaacatcaa gcaccgccta aaaaacggat tttccaacca aatgattata acaatgtgg     12600 aagttgggaa tgtcatcaag tccaagctta ggagttatcc ggcccactct catattccat    12660
atccaaattg taatcaggat ttatttaaca tagaagacaa agagtcaacg aggaagatcc    12720
gtgaactcct caaaaagggg aattcgctgt actccaaagt cagtgataag gttttccaat    12780
gcttaaggga cactaactca cggcttggcc taggctccga attgagggag gacatcaagg    12840
agaaagttat taacttggga gtttacatgc acagctccca gtggtttgag ccctttctgt    12900
```

```
tttggtttac agtcaagact gagatgaggt cagtgattaa atcacaaacc catacttgcc    12960
ataggaggag acacacacct gtattcttca ctggtagttc agttgagttg ctaatctctc    13020
gtgaccttgt tgctataatc agtaaagagt ctcaacatgt atattacctg acatttgaac    13080
tggttttgat gtattgtgat gtcatagagg ggaggttaat gacagagacc gctatgacta    13140
ttgatgctag gtatacagag cttctaggaa gagtcagata catgtggaaa ctgatagatg    13200
gtttcttccc tgcactcggg aatccaactt atcaaattgt agccatgctg gagcctcttt    13260
cacttgctta cctgcagctg agggatataa cagtagaact cagaggtgct ttccttaacc    13320
actgctttac tgaaatacat gatgttcttg accaaaacgg ttttctgat gaaggtactt    13380 atcatgagtt aactgaagct ctagattaca ttttcataac tgatgacata catctgacag    13440
gggagatttt ctcattttc agaagtttcg gccacccccag acttgaagca gtaacggctg    13500
ctgaaaatgt taggaaatac atgaatcagc ctaaagtcat tgtgtatgag actctgatga    13560
aaggtcatgc catattttgt ggaatcataa tcaacggcta tcgtgacagg cacggaggca    13620
gttggccacc gctgaccctc cccctgcatg ctgcagacac aatccggaat gctcaagctt    13680
caggtgaagg gttaacacat gagcagtgcg ttgataactg gaaatctttt gctggagtga    13740
aatttggctg ctttatgcct cttagcctgg atagtgatct gacaatgtac ctaaaggaca    13800
aggcacttgc tgctctccaa agggaatggg attcagttta cccgaaagag ttcctgcgtt    13860
acgaccctcc caagggaacc gggtcacgga ggcttgtaga tgttttcctt aatgattcga    13920
gctttgaccc atatgatgtg ataatgtatg ttgtaagtgg agcttacctc catgaccctg    13980
agttcaacct gtcttacagc ctgaaagaaa aggagatcaa ggaaacaggt agactttttg    14040
ctaaaatgac ttacaaaatg agggcatgcc aagtgattgc tgaaaatcta atctcaaacg    14100
ggattggcaa atattttaag gacaatggga tggccaagga tgagcacgat ttgactaagg    14160
cactccacac tctagctgtc tcaggagtcc ccaaagatct caaagaaagt cacaggggg    14220 ggccagtctt aaaaacctac tcccgaagcc cagtccacac aagtaccagg aacgtgagag    14280
cagcaaaagg gtttataggg ttccctcaag taattcggca ggaccaagac actgatcatc    14340
cggagaatat ggaagcttac gagacagtca gtgcatttat cacgactgat ctcaagaagt    14400
actgccttaa ttggagatat gagaccatca gcttgtttgc acagaggcta aatgagattt    14460
acggattgcc ctcattttc cagtggctgc ataagaggct tgagacctct gtcctgtatg    14520
taagtgaccc tcattgcccc cccgaccttg acgcccatat cccgttatat aaagtcccca    14580
atgatcaaat cttcattaag taccctatgg gaggtatag agggtattgt cagaagctgt    14640
ggaccatcag caccattccc tatctatacc tggctgctta tgagagcgga gtaaggattg    14700
cttcgttagt gcaaggggac aatcagacca tagccgtaac aaaaagggta cccagcacat    14760
ggccctacaa ccttaagaaa cgggaagctg ctagagtaac tagagattac tttgtaattc    14820
ttaggcaaag gctacatgat attggccatc acctcaaggc aaatgagaca attgtttcat    14880
cacatttttt tgtctattca aaaggaatat attatgatgg gctacttgtg tcccaatcac    14940
tcaagagcat cgcaagatgt gtattctggt cagagactat agttgatgaa acaagggcag    15000
catgcagtaa tattgctaca acaatggcta aaagcatcga gagaggttat gaccgttacc    15060
ttgcatattc cctgaacgtc ctaaaagtga tacagcaaat tctgatctct cttggcttca    15120
caatcaattc aaccatgacc cgggatgtag tcatacccct cctcacaaac aacgacctct    15180
taataaggat ggcactgttg cccgctccta ttggggggat gaattatctg aatatgagca    15240
ggctgtttgt cagaaacatc ggtgatccag taacatcatc aattgctgat ctcaagagaa    15300
```

```
tgattctcgc ctcactaatg cctgaagaga ccctccatca agtaatgaca caacaaccgg    15360
gggactcttc attcctagac tgggctagcg acccttactc agcaaatctt gtatgtgtcc    15420
agagcatcac tagactcctc aagaacataa ctgcaaggtt tgtcctgatc catagtccaa    15480
acccaatgtt aaaaggatta ttccatgatg acagtaaaga gaggacgag ggactggcgg     15540 cattcctcat ggacaggcat attatagtac ctagggcagc tcatgaaatc ctggatcata    15600
gtgtcacagg ggcaagagag tctattgcag gcatgctgga taccacaaaa ggcttgattc    15660
gagccagcat gaggaagggg gggttaacct ctcgagtgat aaccagattg tccaattatg    15720
actatgaaca attcagagca gggatggtgc tattgacagg aagaaagaga atgtcctca    15780 ttgacaaaga gtcatgttca gtgcagctgg cgagagctct aagaagccat atgtgggcga    15840
ggctagctcg aggacggcct atttacggcc ttgaggtccc tgatgtacta gaatctatgc    15900
gaggccacct tattcggcgt catgagacat gtgtcatctg cgagtgtgga tcagtcaact    15960
acggatggtt ttttgtcccc tcgggttgcc aactggatga tattgacaag gaaacatcat    16020
ccttgagagt cccatatatt ggttctacca ctgatgagag aacagacatg aagcttgcct    16080
tcgtaagagc cccaagtcga tccttgcgat ctgctgttag aatagcaaca gtgtactcat    16140
gggcttacgg tgatgatgat agctcttgga acgaagcctg gttgttggct aggcaaaggg    16200
ccaatgtgag cctggaggag ctaagggtga tcactcccat ctcaacttcg actaatttag    16260
cgcataggtt gagggatcgt agcactcaag tgaaatactc aggtacatcc cttgtccgag    16320
tggcgaggta taccacaatc tccaacgaca atctctcatt tgtcatatca gataagaagg    16380
ttgatactaa ctttatatac caacaaggaa tgcttctagg gttgggtgtt ttagaaacat    16440
tgtttcgact cgagaaagat accggatcat ctaacacggt attacatctt cacgtcgaaa    16500
cagattgttg cgtgatcccg atgatagatc atcccaggat acccagctcc cgcaagctag    16560
agctgagggc agagctatgt accaacccat tgatatatga taatgcacct ttaattgaca    16620
gagatgcaac aaggctatac acccagagcc ataggaggca ccttgtggaa tttgttacat    16680
ggtccacacc ccaactatat cacatttag ctaagtccac agcactatct atgattgacc     16740
tggtaacaaa atttgagaag gaccatatga atgaaatttc agctctcata ggggatgacg    16800
atatcaatag tttcataact gagtttctgc tcatagagcc aagattattc actatctact    16860
tgggccagtg tgcggccatc aattgggcat ttgatgtaca ttatcataga ccatcaggga    16920
aatatcagat gggtgagctg ttgtcatcgt tcctttctag aatgagcaaa ggagtgttta    16980
aggtgcttgt caatgctcta agccacccaa agatctacaa gaaattctgg cattgtggta    17040
ttatagagcc tatccatggt ccttcacttg atgctcaaaa cttgcacaca actgtgtgca    17100
acatggttta cacatgctat atgacctacc tcgacctgtt gttgaatgaa gagttagaag    17160
agttcacatt tctcttgtgt gaaagcgacg aggatgtagt accggacaga ttcgacaaca    17220
tccaggcaaa acacttatgt gttctggcag atttgtactg tcaaccaggg acctgcccac    17280
caattcgagg tctaagaccg gtagagaaat gtgcagttct aaccgaccat atcaaggcag    17340
aggctatgtt atctccagca ggatcttcgt ggaacataaa tccaattatt gtagaccatt    17400
actcatgctc tctgacttat ctccggcgag gatcgatcaa acagataaga ttgagagttg    17460
atccaggatt catttttcgac gccctcgctg aggtaaatgt cagtcagcca aagatcggca    17520
gcaacaacat ctcaaatatg agcatcaagg ctttcagacc cccacacgat gatgttgcaa    17580
aattgctcaa agatatcaac acaagcaagc acaatcttcc catttcaggg ggcaatctcg    17640
```

```
ccaattatga aatccatgct ttccgcagaa tcgggttgaa ctcatctgct tgctacaaag  17700
ctgttgagat atcaacatta attaggagat gccttgagcc aggggaggac ggcttgttct  17760
tgggtgaggg atcgggttct atgttgatca cttataaaga gatacttaaa ctaaacaagt  17820
gcttctataa tagtggggtt tccgccaatt ctagatctgg tcaaagggaa ttagcaccct  17880
atccctccga agttggcctt gtcgaacaca gaatgggagt aggtaatatt gtcaaagtgc  17940
tctttaacgg gaggcccgaa gtcacgtggg taggcagtgt agattgcttc aatttcatag  18000
ttagtaatat ccctacctct agtgtggggt ttatccattc agatatagag accttgcctg  18060
acaaagatac tatagagaag ctagaggaat tggcagccat cttatcgatg gctctgctcc  18120
tgggcaaaat aggatcaata ctggtgatta agcttatgcc tttcagcggg gattttgttc  18180
agggatttat aagttatgta gggtctcatt atagagaagt gaaccttgta taccctagat  18240
acagcaactt catctctact gaatcttatt tggttatgac agatctcaag gctaaccggc  18300
taatgaatcc tgaaaagatt aagcagcaga taattgaatc atctgtgagg acttcacctg  18360
gacttatagg tcacatccta tccattaagc aactaagctg catacaagca attgtgggag  18420
acgcagttag tagaggtgat atcaatccta ctctgaaaaa acttacacct atagagcagg  18480
tgctgatcaa ttgcgggttg gcaattaacg gacctaagct gtgcaaagaa ttgatccacc  18540
atgatgttgc ctcagggcaa gatggattgc ttaattctat actcatcctc tacagggagt  18600
tggcaagatt caaagacaac caaagaagtc aacaagggat gttccacgct taccccgtat  18660
tggtaagtag caggcaacga gaacttatat ctaggatcac ccgcaaattc tggggggcaca  18720 ttcttcttta ctccgggaac aaaaagttga taaataagtt tatccagaat ctcaagtccg  18780
gctatctgat actagactta caccagaata tcttcgttaa gaatctatcc aagtcagaga  18840
aacagattat tatgacgggg ggtttgaaac gtgagtgggt ttttaaggta acagtcaagg  18900
agaccaaaga atggtataag ttagtcggat acagtgccct gattaaggac taattggttg  18960
aactccggaa ccctaatcct gccctaggtg gttaggcatt atttgcaata tattaaagaa  19020
aactttgaaa atacgaagtt tctattccca gctttgtctg gt                    19062
```